(12) United States Patent
Garry et al.

(10) Patent No.: US 10,897,880 B2
(45) Date of Patent: Jan. 26, 2021

(54) HUMANIZED HEART MUSCLE

(71) Applicant: Regents of the University of Minnesota, Minneapolis, MN (US)

(72) Inventors: Daniel J. Garry, Eagan, MN (US); Mary G. Garry, Eagan, MN (US); Naoko Koyano, Shoreview, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 216 days.

(21) Appl. No.: 15/739,066

(22) PCT Filed: Jun. 30, 2016

(86) PCT No.: PCT/US2016/040431
§ 371 (c)(1),
(2) Date: Dec. 21, 2017

(87) PCT Pub. No.: WO2017/004388
PCT Pub. Date: Jan. 5, 2017

(65) Prior Publication Data
US 2018/0177165 A1  Jun. 28, 2018

Related U.S. Application Data

(60) Provisional application No. 62/187,040, filed on Jun. 30, 2015.

(51) Int. Cl.
*A01K 67/00* (2006.01)
*A01K 67/027* (2006.01)
*C12N 15/85* (2006.01)

(52) U.S. Cl.
CPC ...... *A01K 67/0271* (2013.01); *A01K 67/0276* (2013.01); *C12N 15/8509* (2013.01); *A01K 2217/00* (2013.01); *A01K 2217/15* (2013.01); *A01K 2227/108* (2013.01); *A01K 2267/025* (2013.01)

(58) Field of Classification Search
CPC ............ A01K 67/0271; A01K 67/0276; A01K 2227/108
See application file for complete search history.

(56) References Cited

U.S. PATENT DOCUMENTS

| | | |
|---|---|---|
| 5,994,619 A | 11/1999 | Stice et al. |
| 8,685,737 B2 | 4/2014 | Serber et al. |
| 2005/0125853 A1 | 6/2005 | Parekh |
| 2006/0008451 A1 | 1/2006 | Cibelli et al. |
| 2006/0191029 A1 | 8/2006 | Gavin et al. |
| 2009/0288177 A1 | 11/2009 | Habu et al. |
| 2010/0107263 A1 | 4/2010 | Kerr et al. |
| 2010/0122360 A1 | 5/2010 | Nakauchi et al. |
| 2011/0277047 A1 | 11/2011 | Bruggemann |
| 2012/0207744 A1 | 8/2012 | Mendlein et al. |
| 2014/0115728 A1 | 4/2014 | Tector |
| 2014/0186414 A1 | 7/2014 | Ingber et al. |
| 2015/0168125 A1 | 6/2015 | Arieli et al. |
| 2016/0029604 A1 | 2/2016 | Fahrenkrug et al. |
| 2018/0037620 A1 | 2/2018 | Garry et al. |
| 2018/0177166 A1 | 6/2018 | Garry et al. |

FOREIGN PATENT DOCUMENTS

| | | |
|---|---|---|
| CN | 108024522 A | 5/2018 |
| CN | 108125943 A | 6/2018 |
| CN | 108472318 A | 8/2018 |
| EP | 2258166 A1 | 12/2010 |
| GB | 2475656 | 5/2011 |
| JP | 2010515737 A | 5/2010 |
| JP | 2014533491 A | 12/2014 |
| JP | 2018-506984 A | 3/2018 |
| JP | 2018522553 | 8/2018 |
| JP | 2018523999 | 8/2018 |
| WO | WO-2004004447 A2 | 11/2004 |
| WO | WO-2008/102602 A1 | 8/2008 |
| WO | WO-2015168125 A1 | 11/2015 |
| WO | WO-2016/141234 A1 | 9/2016 |
| WO | WO-2017/004367 A1 | 1/2017 |
| WO | WO-2017004388 A1 | 1/2017 |
| WO | 2017075276 | 5/2017 |

OTHER PUBLICATIONS

Zhou et al. Biochemical and Biophysical Research Communications 375:450-453, 2008 (Year: 2008).*
Yao et al. Scientific Reports 4:6926, DIO:10.1038/srep06926. pp. 1-8, 2014 (Year: 2014).*
Cui et al. Scientific Reports 5:10482. DIO:10.1038/srep10482. pp. 1-11, May 2015 (Year: 2015).*
Wu et al. PNAS www.pnas.org/cgi/doi/10.1073/pnas.1421587112. E1530-E1539, Mar. 2015 (Year: 2015).*

(Continued)

*Primary Examiner* — Marcia S Noble
(74) *Attorney, Agent, or Firm* — Schwegman Lundberg & Woessner, P.A.

(57) ABSTRACT

Described herein is a method for producing a chimeric non-human animal expressing a human NKX2-5, HANDII, TBX5 gene or a combination thereof gene comprising: a) generating a NKX2-5, HANDII, TBX5 or combination thereof null non-human animal cell, wherein both copies of the non-human NKX2-5, HANDII, TBX5 gene or combination thereof carry a mutation that prevents production of functional NKX2-5, HANDII, TBX5 protein or combination thereof in said non-human animal; b) creating a NKX2-5, HANDII, TBX5 or combination thereof null non-human blastocyst by somatic cell nuclear transfer comprising fusing a nucleus from said NKX2-5, HANDII, TBX5 or combination thereof null non-human animal cell of a) into an enucleated non-human oocyte and activating said oocyte to divide so as to form an NKX2-5, HANDII, TBX5 or combination thereof null non-human blastocyst; c) introducing human stem cells into the NKX2-5, HANDII, TBX5 or combination null non-human blastocyst of b); and d) implanting said blastocyst from c) into a pseudopregnant surrogate non-human animal to generate a chimeric non-human animal expressing human NKX2-5, HANDII, TBX5 or combination thereof.

2 Claims, 15 Drawing Sheets

Specification includes a Sequence Listing.

(56) References Cited

OTHER PUBLICATIONS

"European Application Serial No. 16818785.4, Extended European Search Report dated Jan. 24, 2019", 7 pgs.
"Australian Application Serial No. 2016288196, First Statement of Proposed Amendments filed Jan. 31, 2018", 12 pgs.
"Canadian Application Serial No. 2,991,053, Voluntary Amendment filed Oct. 18, 2018", 13 pgs.
"U.S. Appl. No. 15/554,585, Final Office Action dated Aug. 2, 2019", 28 pgs.
"Egyptian Application Serial No. PCT 1471/2017, Office Action dated Aug. 22, 2019", (w/ English Summary), 4 pgs.
"European Application Serial No. 16818785.4, Response filed Aug. 9, 2019 to Extended European Search Report dated Jan. 24, 2019", 6 pgs.
"International Application Serial No. PCT/US2016/040431, International Search Report dated Oct. 26, 2016", 4 pgs.
"International Application Serial No. PCT/US2016/040431, Written Opinion dated Oct. 26, 2016", 7 pgs.
Niu, Yuyu, et al., "Generation of Gene-Modified Cynomolgus Monkey via Cas9/RNA-Mediated Gene Targeting in One-Cell Embryos", Cell 156, (Feb. 2014), 836-843.
Rashid, Tamir, et al., "Revisiting the Flight of Icarus: Making Human Organs from PSCs with Large Animal Chimeras", Cell Stem Cell 15, (Oct. 2014), 406-409.
"U.S. Appl. No. 15/554,585, Non Final Office Action dated Nov. 7, 2018", 19 pgs.
Kataoka, Hiroshi, "Etv2 ER71 induces vascular mesoderm from Flk1+PDGFR alpha+ primitive mesoderm", Blood, 18(26), (2011), 6975-6986.
"European Application Serial No. 16818799.5, Extended European Search Report dated Feb. 28, 2019", 10 pgs.
Nagashima, Hiroshi, et al., "Growing human organs in pigs—A dream or reality?", Theriogenology, 86(1), (2016), 422-426.
Rasmussen, Tara L., et al., "Etv2 rescues Flk1 mutant embryoid bodies", Genesis, 51(7), (2013), 471-480.
Wu, Jun, et al., "Interspecies Chimerism with Mammalian Pluripotent Stem Cells", Cell, 168(3), (2017), 473-486 (30 pgs.).
U.S. Appl. No. 15/554,585, Response filed Feb. 3, 2020 to Final Office Action dated Aug. 2, 2019, 11 pgs.
U.S. Appl. No. 15/739,042, Restriction Requirement dated Jan. 8, 2020, 10 pgs.
Canadian Application Serial No. 2,978,457, Voluntary Amendment filed Oct. 19, 2018, 10 pgs.
European Application Serial No. 16759528.9, Communication Pursuant to Article 94(3) EPC dated Nov. 22, 2019, 6 pgs.
European Application Serial No. 16759528.9, Response filed Jun. 5, 2019 to Communication dated Apr. 8, 2019 and to the Supplemental European Search Report, 11 pgs.
Japan Approves First Human-Animal Embryo Experiments, Retrieved from the Internet: URL:<https://www.nature.com/articles/d41586-019-02275-3> [retrieved on Nov. 19, 2019], (Jul. 26, 2019).
Japanese Application Serial No. 2017-546061, Notification of Reasons for Refusal dated Jan. 15, 2020, (w/ English Translation), 12 pgs.
New Zealand Patent Application Serial No. 735956, Voluntary Amendment filed Oct. 31, 2017, 45 pgs.
Lillico, Simon G., et al., "Live pigs produced from genome edited zygotes", Scientific Reports, 3: 2847, (2013), 1-4.
Rudnicki, Michael A., et al., "MyoD or Myf-5 is required for the formation of skeletal muscle", Cell 75(7), (1993), 1351-1359.
Zhou, Xiaoqing, et al., "Generation of CRISPR/Cas9-mediated gene-targeted pigs via somatic cell nuclear transfer", Cell. Mol. Life Sci., 72, (2015), 1175-1184.
"Colombian Application Serial No. NC2018/0000859, Response filed Jun. 13, 2018 to Office Action dated Feb. 21, 2018", (w/ English Translation of Claims), 14 pgs.
"European Application Serial No. 16759528.9, Extended European Search Report dated Aug. 8, 2018", 8 pgs.
"European Application Serial No. 16818785.4, Response filed May 21, 2018 to Office Action dated Feb. 16, 2018", 5 pgs.

"European Application Serial No. 16818799.5, Response filed May 21, 2018 to Office Action dated Feb. 16, 2018", 5 pgs.
"Singaporean Patent Application No. 11201707151Y, Search Report and Written Opinion dated Sep. 10, 2018", 16 pgs.
Elcheva, Irina, et al., "Direct induction of hematoendothelial programs in human pluripotent stem cells by transcriptional regulators", Nature Communications, 5: 4372, (2014), 1-11.
Koyano-Nakagawa, N., et al., "Feedback Mechanisms Regulate Ets Variant 2 (Etv2) Gene Expression and Hematoendothelial Lineages", J. Biol. Chem., 290(40), (2015), 28107-28119.
Lammerts Van Bueren, Kelly, et al., "Regulation of endothelial and hematopoietic development by the ETS transcription factor Etv2", Current Opinion in Hematology, 19(3), (Mayrch 2012), 199-205.
Morita, Rimpei, et al., "ETS transcription factor ETV2 directly converts human fibroblasts into functional endothelial cells", Proc. Natl. Acad. Sci. USA, 112(1), (Dec. 24, 2014), 160-165.
Swaminathan, Preethi, "Human Stem Cell Complementation in PITX3 Null Porcine Blastocysts: Lens Development", [Online]. Retrieved from the Internet: <https://conservancy.unm.edu/bitstream/handle/11299/185108/Swami nathan_umn_0130M_15713.pdf>, (Dec. 2014), 57 pages.
Wu, Jun, et al., "An alternative pluripotent state confers interspecies chimaeric competency", Nature, vol. 521, (2015), 23 pgs.
"U.S. Appl. No. 15/554,585, Response filed May 7, 2019 to Non Final Office Action dated Nov. 7, 2018", 18 pgs.
"Directive 98/44/EC of the European Parliament and of the Council of Jul. 6, 1998", Official Journal of the European Communities, (1998), 9 pgs.
"European Application Serial No. 16860825.5, Supplementary European Search Report dated Apr. 9, 2019", 12 pgs.
"European Application Serial No. 16860830.5, Supplementarry Partial European Search Report dated Apr. 16, 2019", 13 pgs.
Bouchard, Maxime, et al., "Nephric lineage specification by Pax2 and Pax8", Genes & Development, 16(22), (2002), 2958-2970.
Goto, Teppei, et al., "Generation of pluripotent stem cell-derived mouse kidneys in Sall1-targeted anephric rats", Nature Communications, 10, Article No. 451, (2019), 1-9.
Liu, Yunying, et al., "Generation of functional organs from stem cells", Cell Regeneration, 2:1, (2013), 1-6.
Wang, Xianlong, et al., "Efficient CRISPR/Cas9-mediated biallelic gene disruption and site-specific knockin after rapid selection of highly active sgRNAs in pigs", Scientific Reports, 5: 13348, (2015), 1-11.
"Singaporean Patent Application No. 11201707151Y, Response Filed Jan. 7, 2019 to Search Report and Written Opinion dated Sep. 10, 2018", w English Claims, 42 pgs.
"U.S. Appl. No. 15/554,585, Preliminary Amendment filed Aug. 30, 2017", 7 pgs.
"U.S. Appl. No. 15/554,585, Supplemental Preliminary Amendment filed Sep. 12, 2017", 3 pgs.
"U.S. Appl. No. 15/739,042, Preliminary Amendment filed Dec. 21, 2017", 9 pgs.
"Colombian Application Serial No. NC2018/0000859, Office Action dated Feb. 21, 2018", (w/ English Translation), 6 pgs.
"International Application Serial No. PCT/US16/20768, International Search Report dated Jul. 22, 2016", 3 pgs.
"International Application Serial No. PCT/US16/20768, Written Opinion dated Jul. 22, 2016", 4 pgs.
"International Application Serial No. PCT/US2016/020768, International Preliminary Report on Patentability dated Sep. 14, 2017", 6 pgs.
"International Application Serial No. PCT/US2016/040378, International Preliminary Report on Patentability dated Jan. 11, 2018", 9 pgs.
"International Application Serial No. PCT/US2016/040378, International Search Report dated Oct. 26, 2016", 4 pgs.
"International Application Serial No. PCT/US2016/040378, Written Opinion dated Oct. 26, 2016", 7 pgs.
"International Application Serial No. PCT/US2016/040431, International Preliminary Report on Patentability dated Jan. 11, 2018", 9 pgs.
"Japanese Application Serial No. 2017-546061, Written Amendment filed Dec. 1, 2017", (w/ English Translation of Amended Claims), 11 pgs.
"Vietnamese Application Serial No. 1-2017-03882, Office Action dated Dec. 4, 2017", (w/ English Translation), 2 pgs.

(56) References Cited

OTHER PUBLICATIONS

"Vietnamese Application Serial No. 1-2017-03882, Response filed Jan. 4, 2018 to Office Action dated Dec. 4, 2017", (w English Translation of Amended Claims), 9 pgs.

Beaucage, S., et al., "Deoxynucleoside Phosphoramidites—A New Class of Key Intermediate for Deoxypolynucleotide Synthesis", Tetrahedron Letters, 22, (1981), 1859-1862.

Berkes, C. A., et al., "MyoD and the transcriptional control of myogenesis", Seminars in Cell & Developmental Biology, 16, (2005), 585-595.

Bodmer, R., "The gene tinman is required for specification of the heart and visceral muscles in *Drosophila*", Development, 118(3), (1993), 719-729.

Bort, R., et al., "Hex homeobox gene controls the transition of the endoderm to a pseudostratified, cell emergent epithelium for liver bud development", Developmental Biology, 290(1), (2006), 44-56.

Bowlin, K. M., et al., "Kbtbd5 is regulated by MyoD and restricted to the myogenic lineage", Differentiation, 86, (2013), 184-191.

Bruneau, B. G., et al., "A Murine Model of Holt-Oram Syndrome Defines Roles of the T-Box Transcription Factor Tbx5 in Cardiogenesis and Disease", Cell, 106(6), (Sep. 2001), 709-721.

Caprioli, A., et al., "Nkx2-5 Represses Gata1 Gene Expression and Modulates the Cellular Fate of Cardiac Progenitors During Embryogenesis", Circulation, 123(15), (2011), 1633-1641.

Carlson, D. F., et al., "Efficient TALEN-mediated gene knockout in liverstock", Proc. Natl. Acad. Sci., 109(43), (2012), 17382-17387.

Ferdous, A., "Nkx2-5 transactivates the Ets-related protein 71 gene and specifies an endothelial/endocardial fate in the developing embryo", Proc. Natl. Acad. Sci. USA, 106(3), (2009), 814-819.

Garry, D. J., et al., "A Common Progenitor at the Heart of Development", Cell, 127(6), (2006), 1101-1104.

Garry, D. J., et al., "Cardiac Regeneration—Self-Service at the Pump", Circulation Research, 95, (2004), 852-854.

Grefte S., Kuijpers Mar, et al., "Myogenic capacity of muscle progenitor cells from head and limb muscles", Eur. J. Oral Sci., 120(1), (2012), 38-45.

Hiroi, Y., "Tbx5 associates with Nkx2-5 and synergistically promotes cardiomyocyte differentiation", Nat Genet., 28(3), (2001), 276-280.

Jansen, Katie M., et al., "Molecular Control of Mammalian Myoblast Fusion", Methods in Molecular Biology, vol. 475—Cell Fusion: Overviews and Methods, (Feb. 2008), 115-133.

Kassar-Duchossoy, L., et al., "Mrf4 determines skeletal muscle identity in Myf5:Myod double-mutant mice", Nature, 4317007), (2004), 466-471.

King, T. J., et al., "Embryo development and establishment of pregnancy after embryo transfer in pigs: Coping with limitations in the availability of viable embryos", Reproduction, 123(4), (2002), 507-515.

Kobayashi, Toshihiro, et al., "Generation of Rat Pancreas in Mouse by Interspecific Blastocyst Injection of Pluripotent Stem Cells", Cell, 142(5), (2010), 787-799.

Koyano-Nakagawa, Naoko, et al., "Etv2 is expressed in the yolk sac hematopoietic and endothelial progenitors and regulates Lmo2 gene expression", Stem Cells, 30(8), (2012), 1611-1623.

Kure-Bayashi, S., et al., "Successful implantation of in vitro-matured, electo-activated oocytes in the pig", Theriogenology, 53(5), (2000), 1105-1119.

Latif, S., et al., "Transcriptional Pathways Direct Cardiac Development and Regeneration", Trends Cardiovasc Med., 16(7), (2006), 234-240.

Lewis, F. C., et al., "Porcine Sketal Muscke-Derived Multipotent PW1$^{pos}$/Pax7$^{neg}$ Interstitial cells: Isolation, Characterization, and Long-Term Culture", Stem Cells Transl Med, 3(6), (2014), 702-712.

Lyons, I., et al., "Myogenic and morphogenetic defects in the heart tubes of murine embryos lacking the homeo box gene Nkx2-5", Genes & Development, 9(13), (1995), 1654-1666.

Matsunari, Hitomi, et al., "Blastocyst complementation generates exogenic pancreas in vivo in apancreatic cloned pigs", Proc. Natl. Acad. Sci., 110(12), (2013), 4557-4562.

Matteucci, M. D., et al., "Synthesis of Deoxyoligonucleotides on a Polymer Support", J. Am. Chem. Soc., 103, (1981), 3185-3191.

Mckarney, Lesley A., et al., "Myogenesis in Cultures of Uniparental Mouse Embryonic Stem Cells: Differing Patterns of Expression of Myogenic Regulatory Factors", Int. J. Dev. Biol., 41, (1997), 485-490.

Nakano, Kazuaki, et al., "Generating Porcine Chimeras Using Inner Cell Mass Cells and Parthenogenetic Preimplantation Embryos", PLoS One, 8(4): e61900, (Apr. 2013), 1-10.

Pasut, A., et al., "Chapter 3—Isolation of Muscle Stem Cells by Fluorescence Activated Cell Sorting Cytometry", DiMario, J. X., (ed.), Myogenesis: Methods Mol Biol., vol. 798, (2012), 53-64.

Rasmussen, T. L., et al., "Getting to the Heart of Myocardial Stem Cells and Cell Therapy", Circulation, 123, (2011), 1771-1779.

Rasmussen, T. L., et al., "Abstract 15450: Ets Related Protein 71 Regulates Cardiac Morphogenesis", Circulation, 122: A15450, (2010), 2 pgs.

Rasmussen, T. L., et al., "Abstract 17036: Flk1 Mediated Activation of ER71 and Specification of Cardiovascular Lineages", Circulation, 124: A17036, (2011), 2 pgs.

Rasmussen, T. L., et al., "ER71 directs mesodermal fate decisions during embryogenesis", Development 138, (2011), 4801-4812.

Rasmussen, T. L., et al., "VEGF/Flk1 Signaling Cascade Transactivates Etv2 Gene Expression", PLoS One, 7(11): e50103, (Nov. 2012), 1-12.

Sabourin, L. A., et al., "The molecular regulation of myogenesis", Clin. Genet., 57, (2000), 16-25.

Shi, X., et al., "Cooperative interaction of Etv2 and Gata2 regulates the development of endothelial and hematopoietic lineages", Developmental Biology, 389(2), (2014), 208-218.

Shi, X., et al., "Muscle stem cells in development, regeneration, and disease", Genes & Development 20, (2006), 1692-1708.

Shi, Xiaozhong, et al., "The Transcription Factor Mesp1 Interacts with cAMP-responsive Element Binding Protein 1 (Creb1) and Coactivates Ets Variant 2 (Etv2) Gene Expression", The Journal of Biological Chemistry, 290(15), (Feb. 18, 2015), 9614-9625.

Srivastava, D., et al., "Regulation of cardiac mesodermal and neural crest development by the bHLH transcription factor", Nat Gen., 16(2), (1997), 154-160.

Takeda, Kumiko, "Microinjection of serum-starved mitochondria derived from somatic cells affects parthenogenetic development of bovine and murine oocytes", Mitochondrion, 10(2), (Mar. 2010), 137-142.

Tan, Wenfang, et al., "Efficient nonmeiotic allele introgression in livestock using custom endonucleases", Proc. Natl. Acad. Sci., 110(41), (2013), 16526-16531.

Tapscott, Stephen J., et al., "The circuitry of a master switch: Myod and the regulation of skeletal muscle gene transcription", Development, 132(12), (2005), 2685-2695.

Te Pas, M. F., et al., "Biochemical pathways analysis of microarry results: regulation of myogenesis in pigs", BMC Dev. Bio., 7: 66, (2007), 1-15.

Usui, Jo-Ichi, et al., "Generation of Kidney from Pluripotent Stem Cells via Blastocyst Complementation", The American Journal of Pathology, 180(6), (Jun. 2012), 2417-2426.

Wang, Haoyl, et al., "One-Step Generation of Mice Carrying Mutations in Multiple Genes by CRISPR/Cas-Mediated Genome Engineering", Cell, 153, (2013), 910-918.

Wareing, S., et al., "The Flkl-Cre-Mediated Deletion of ETV2 Defines Its Narrow Temporal Requirement During Embryonic Hematopoietic Development", Stem Cells, vol. 30, (Jun. 18, 2012), 1521-1531.

Woolf, A. D., et al., "Burden of major musculoskeletal conditions", Bulletin of the World Health Organization, 81(9), (2003), 646-656.

Wu, J., et al., "Generation of human organs in pigs via interspecies blastocyst complementation", Reprod Dom Anim 51(Suppl. 2), (2016), 18-24.

Yamagishi, H., "The combinatorial activities of Nkx2.5 and dHAND are essential for cardiac ventricle formation", Developmental Biology, 239(2), (2001), 190-203.

Zhu, J., "In Vitro and In Vivo Developmental Competence of Ovuated and In Vitro Matured Porcine Oocytes Activated by Electrical Activation", Cloning Stem Cells, 5(4), (2003), 355-365.

(56) References Cited

OTHER PUBLICATIONS

"Japanese Application Serial No. 2017-568252, Notification of Reasons for Rejection dated Jun. 29, 2020", 12 pgs.

"Application Serial No. 15/554,585, Non Final Office Action dated Jun. 1, 2020", 36 pgs.

"Application Serial No. 15/739,042, Non Final Office Action dated Apr. 1, 2020", 27 pgs.

"Application Serial No. 15/739,042, Response filed Mar. 9, 2020 to Restriction Requirement dated Jan. 8, 2020", 11 pgs.

"Application Serial No. 15/739,042, Response filed Jun. 12, 2020 to Non Final Office Action dated Apr. 1, 2020", 12 pgs.

"European Application Serial No. 16759528.9, Response filed Mar. 20, 2020 to Communication Pursuant to Article 94(3) EPC dated Nov. 22, 2019", 25 pgs.

"European Application Serial No. 16818799.5, Communication Pursuant to Article 94(3) EPC dated Jun. 12, 2020", 5 pgs.

"Japanese Application Serial No. 2017-568279, Notification of Reasons for Rejection dated Apr. 6, 2020", w/ English Translation, 8 pgs.

Kassar-Duchossoy, L., et al., "Mrf4 Determines Skeletal Muscle Identity in Myf5:Myod Double-Mutant Mice", Nature, 431, (2004), 466-471.

Matsunari, Hitomi, et al., "Blastocyst complementation generates exogenic pancreas in vivo in apancreatic cloned pigs", Proc. Natl. Acad, Sci., USA, 110(12), (May 30, 2018), 4557-4562.

Ott, M.-O., et al., "Early Expression of the Myogenic Regulatory Gene, myf-5, in Precursor Cells of Skeletal Muscle in the Mouse Embryo", Development, 111(4), (1991), 1097-1107.

Valdez, M. Renee, et al., "Failure of Myf5 to Support Myogenic Differentiation without Myogenin, MyoD, and MRF4", Developmental Biology, 219(2), (2000), 287-298.

"U.S. Appl. No. 15/739,042, Notice of Allowance dated Aug. 19, 2020", 10 pgs.

"European Application Serial No. 16818785.4, Communication Pursuant to Article 94(3) EPC dated Aug. 20, 2020", 4 pgs.

"Chinese Application Serial No. 201680024200.8, Office Action dated Jun. 15, 2020", 9 pgs.

\* cited by examiner

| Nkx 2.5 6kb ENHANCER | Hsp68 | EYFP |
*Fig. 5A*
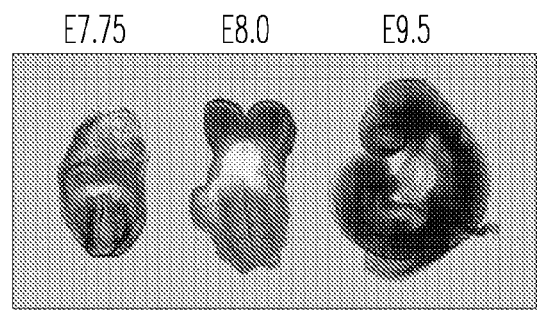
*Fig. 5B*
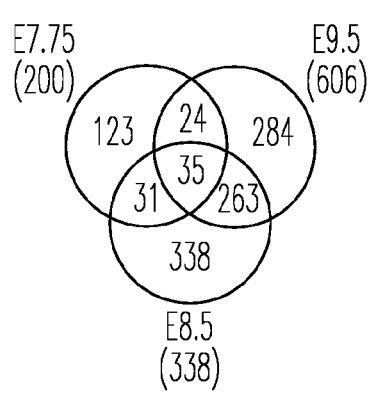
*Fig. 5C*
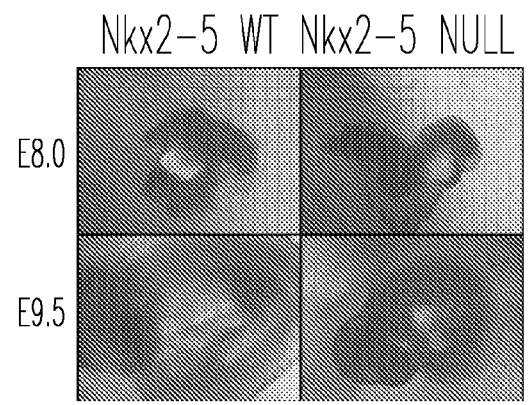
*Fig. 5D*

SEQUENCE LISTING

```
<160> NUMBER OF SEQ ID NOS: 15

<210> SEQ ID NO 1
<211> LENGTH: 1725
<212> TYPE: DNA
<213> ORGANISM: Sus scrofa
```

```
<400> SEQUENCE: 1 gtcccctcc tccggcctgg tcccgcctct cctgcccctt gcgccccgca ttacctgccg    60
cctggccaca tcccgagctg aaggcgggt gcgcgggcgc gcagcgggca ccatgcaggg   120
aggctgccag ggaccgtggg cagcgccgct ctctgccgcc cacctggcgc tgtgagacgc   180
gcgctgccac catgttcccc agccccgcgc tcacgcccac gccgttctcg gtcaaagaca   240
tcttgaacct ggagcaacag cagcgcagcc tggccgccgg gagctctccc gcgcgcttgg   300
aggccaccct ggcgcccgcc tcctgcatgc tggccgcctt caagcccgag cctacgcgg    360 ggccggaggc cgcagcgccc ggcctctccg agctgcgcgc cgagctgggc cccgcgccct   420
caccagccaa gtgcgcgccc tccttctcag ccgccccgc cttctacccg cgtgcctatg    480
gcgaccccga ccccgccaag gaccctcgag ccgataagaa aggtgaggag gaaacacaag   540
cttcttctct gcctctctgt tccccccgc agagctgtgc gcgctgcaga aggcggtgga    600
gctggagaag ccagaggcgg acagcgccga gagacctcgg gcgcgacgac gaaggaagcc   660
gcgcgtgctc ttttcgcagg cacaggtcta cgagctggag cgacgcttca gcagcagcg    720 gtacctgtcg gctcccgagc gtgaccagtt ggccagcgtg ctgaagctca cgtccacgca   780
ggtcaagatc tggttccaga accggcgcta caagtgcaag cggcaacggc aggaccagac   840
tctggagcta gtggggctgc ccccgccccc gccgccgccg gcccgcagga tcgcggtgcc   900
agtgctggtc gcgcgatggca agccttgcct cggggactcc gcgccctacg cgccagccta   960
cggcgtgggc ctcaacgcct acggctataa cgcctacccc gcctaccgg gttacggtgg    1020 cgcggcctgc agccctggct acagctgcac cgctgcgtac ccagccgggc cgcccccggc   1080
gcagtcggct acggccgccg ccaataacaa cttcgtgaac ttcggcgtcg gggacttaaa   1140
cgcggtgcag agcccgggga ttccgcaggg caactcggga gtgtccacgc tgcacggtat   1200
ccgagcctgg tagggaaggg gcctgtctgg ggcacctcta agagggggca ctaactatcg   1260
gggagaggga gggctcccga tacgatcctg agtccctcag atgtcacatt gactcccacg   1320
gaggcctcgg agcttttttcc gtccggtgcg cctttatccc cacgcgcggg agagttcgtg   1380
gcagaggtta cgcagcttgg ggtgagtgat cccgcagccc ggtgccttag ccgtcgcccc   1440
gggagtgccc tccaagcgcc cacgggcatc cccaatcggc tgacaccggc cagttgggac   1500
cgggagcccg agcccaggcg tgccaggctt aagatgggc cgccttttccc cgatcctggg    1560 cccggtgccc ggggccttg ctgccttgcc gctgccctcc ccacacccgt atttatgttt    1620
ttacttgttt ctgtaagaaa tgagaatctc cttcccatta aagagagtgc gctgatccgc   1680
ctgtgtgctt ctttcagctt gctgtgcttc agaaactgaa atttt               1725

<210> SEQ ID NO 2
<211> LENGTH: 972
<212> TYPE: DNA
<213> ORGANISM: Sus scrofa

<400> SEQUENCE: 2
atgttcccca gccccgcgct cacgcccacg ccgttctcgg tcaaagacat cttgaacctg     60
gagcaacagc agcgcagcct ggccgccggg agctctccg cgcgcttgga ggccaccctg    120
gcgcccgcct cctgcatgct ggccgccttc aagcccgagg cctacgcggg gccggaggcc    180
gcagcgcccg gcctctccga gctgcgcgcc gagctgggcc ccgcgccctc accagccaag    240
tgcgcgcccc ccttctcagc cgccccgcc ttctacccgc gtgcctatgg cgaccccgac     300
cccgccaagg accctcgagc cgataagaaa gagctgtgcg cgctgcagaa ggcggtggag    360
```

-continued

```
ctggagaagc cagaggcgga cagcgccgag agacctcggg cgcgacgacg aaggaagccg      420
cgcgtgctct tttcgcaggc acaggtctac gagctggagc gacgcttcaa gcagcagcgg      480
tacctgtcgg ctcccgagcg tgaccagttg gccagcgtgc tgaagctcac gtccacgcag      540
gtcaagatct ggttccagaa ccggcgctac aagtgcaagc ggcaacggca ggaccagact      600
ctggagctag tggggctgcc cccgcccccg ccgccgccgg cccgcaggat cgcggtgcca      660
gtgctggtgc gcgatggcaa gccttgcctc ggggactccg cgccctacgc gccagcctac      720
ggcgtgggcc tcaacgccta cggctataac gcctaccccg cctacccggg ttacggtggc      780
gcggcctgca gccctggcta cagctgcacc gctgcgtacc cagccgggcc gccccggcg       840 cagtcggcta cggccgccgc caataacaac ttcgtgaact tcggcgtcgg ggacttaaac      900
gcggtgcaga gcccggggat tccgcagggc aactcgggag tgtccacgct gcacggtatc      960
cgagcctggt ag                                                         972
```

<210> SEQ ID NO 3
<211> LENGTH: 323
<212> TYPE: PRT
<213> ORGANISM: Sus scrofa

<400> SEQUENCE: 3

```
Met Phe Pro Ser Pro Ala Leu Thr Pro Thr Pro Phe Ser Val Lys Asp
1               5                   10                  15

Ile Leu Asn Leu Glu Gln Gln Gln Arg Ser Leu Ala Ala Gly Glu Leu
            20                  25                  30

Ser Ala Arg Leu Glu Ala Thr Leu Ala Pro Ala Ser Cys Met Leu Ala
        35                  40                  45

Ala Phe Lys Pro Glu Ala Tyr Ala Gly Pro Glu Ala Ala Pro Gly
    50                  55                  60

Leu Ser Glu Leu Arg Ala Glu Leu Gly Pro Ala Pro Ser Pro Ala Lys
65                  70                  75                  80

Cys Ala Pro Ser Phe Ser Ala Ala Pro Ala Phe Tyr Pro Arg Ala Tyr
                85                  90                  95

Gly Asp Pro Asp Pro Ala Lys Asp Pro Arg Ala Asp Lys Lys Glu Leu
            100                 105                 110

Cys Ala Leu Gln Lys Ala Val Glu Leu Glu Lys Pro Glu Ala Asp Ser
        115                 120                 125

Ala Glu Arg Pro Arg Ala Arg Arg Arg Lys Pro Val Leu Phe
    130                 135                 140

Ser Gln Ala Gln Val Tyr Glu Leu Glu Arg Arg Phe Lys Gln Gln Arg
145                 150                 155                 160

Tyr Leu Ser Ala Pro Glu Arg Asp Gln Leu Ala Ser Val Leu Lys Leu
                165                 170                 175

Thr Ser Thr Gln Val Lys Ile Trp Phe Gln Asn Arg Arg Tyr Lys Cys
            180                 185                 190

Lys Arg Gln Arg Gln Asp Gln Thr Leu Glu Leu Val Gly Leu Pro Pro
        195                 200                 205

Pro Pro Pro Pro Ala Arg Arg Ile Ala Val Pro Val Leu Val Arg
    210                 215                 220

Asp Gly Lys Pro Cys Leu Gly Asp Ser Ala Pro Tyr Ala Pro Ala Tyr
225                 230                 235                 240

Gly Val Gly Leu Asn Ala Tyr Gly Tyr Asn Ala Tyr Pro Ala Tyr Pro
                245                 250                 255
```

```
Gly Tyr Gly Gly Ala Ala Cys Ser Pro Gly Tyr Ser Cys Thr Ala Ala
            260                 265                 270

Tyr Pro Ala Gly Pro Pro Ala Gln Ser Ala Thr Ala Ala Ala Asn
        275                 280                 285

Asn Asn Phe Val Asn Phe Gly Val Gly Asp Leu Asn Ala Val Gln Ser
    290                 295                 300

Pro Gly Ile Pro Gln Gly Asn Ser Gly Val Ser Thr Leu His Gly Ile
305                 310                 315                 320

Arg Ala Trp

<210> SEQ ID NO 4
<211> LENGTH: 1458
<212> TYPE: DNA
<213> ORGANISM: Sus scrofa

<400> SEQUENCE: 4
atggagatct tgctgggaaa atccgcttgc tcccctcacg gcgtccagtc ccggagaaca      60
gccgccgccg ccgtcaccca ggagccccca cggccgctgc gcaacagccc tccaagcccc    120
agccgccgcc ttcgcggagc acgagaggag agcggaacac gttactcgct gctaaagtca    180
cattccagga ccaaaacaac aacaaccaaa aatttcatta aaacaataag cgcccaagaa    240
cccagatcag gctggttggg ggaagagatc ggccaccccg agatgtcgcc ccccgactac    300
agcatggccc tgtcctacag tccggagtac gccagcggtg ccgccagcct ggaccactcc    360
cattacgggg gggtgccgcc gggcgccggg ccccgggcc tggggggggcc gcgcccggtg    420 aagcgccggg gcacagccaa ccgcaaggag cggcgcagga ctcagagcat caacagcgcc    480
ttcgccgagc tgcgcgagtg tatccccaat gtgcccgccg acaccaaact ctccaagatc    540
aagacgctgc gcctggccac cagctacatc gcctacctca tggacctgct ggccaaggac    600
gaccagaacg gcgaggcgga ggcctttaag gcggaaatca agaagacaga tgtgaaagaa    660
gagaaaagga gaaggagct gaatgaaatc ttgaaaagca cagtgagcag caacgacaag    720
aaaaccaaag gccggacggg ctggccgcag catgtctggg ccctggagct caagcagtga    780 ggtgagaaa aggaggtgg aggtggtgga agaggaggag gagagcgcga gccaggccct    840
ggagccggat gcagacccag gactccgggg cgagctctgc gcactccgct ctgaggactt    900
cctgcatttg gatcatccgg tttatttatg tgcaatgtgc ctccctctct ttgcccccct    960
ttgaggcatc cgctccccac caccccctcc aaaaaagtgg atatttgaag aaaagcattc   1020
catattttaa tatgaagagg acactcccgc gtggtaaggg atcccgtcgt cgtcttgtag   1080
attctctgtt tgtgaatgtt tcctcttggc tgtgtagaca ccagcgttgc tccctcccca   1140
cctatccagc cccttacaga taaagacagc tgataatagt gtatttgtga agtgtatctt   1200
taatacctgg cctttggata taaatattcc tggggattat aaagttttat ttcaaagcag   1260
aaaacggggc cgctaacatt tccgttgggg tcggtatcta gtgctgccgt ttcatctgtg   1320
tggttcccta tttgaagatg tttccaacag ctccttgttt tgtgcacttc cgtcctctaa   1380
aactaagtgg aatttaatta atattgaagg tgtaaacgtt gtaagtaatc aataaaccac   1440
tgtgtgtttt ttttttttt                                                 1458

<210> SEQ ID NO 5
<211> LENGTH: 259
<212> TYPE: PRT
<213> ORGANISM: Sus scrofa
```

```
<400> SEQUENCE: 5

Met Glu Ile Leu Leu Gly Lys Ser Ala Cys Ser Pro His Gly Val Gln
1               5                   10                  15

Ser Arg Arg Thr Ala Ala Ala Val Thr Gln Glu Pro Pro Arg Pro
            20                  25                  30

Leu Arg Asn Ser Pro Pro Ser Pro Ser Arg Arg Leu Arg Gly Ala Arg
            35                  40                  45

Glu Glu Ser Gly Thr Arg Tyr Ser Leu Leu Lys Ser His Ser Arg Thr
50                  55                  60

Lys Thr Thr Thr Thr Lys Asn Phe Ile Lys Thr Ile Ser Ala Gln Glu
65                  70                  75                  80

Pro Arg Ser Gly Trp Leu Gly Glu Glu Ile Gly His Pro Glu Met Ser
                85                  90                  95

Pro Pro Asp Tyr Ser Met Ala Leu Ser Tyr Ser Pro Glu Tyr Ala Ser
            100                 105                 110

Gly Ala Ala Ser Leu Asp His Ser His Tyr Gly Gly Val Pro Pro Gly
            115                 120                 125

Ala Gly Pro Pro Gly Leu Gly Gly Pro Arg Pro Val Lys Arg Arg Gly
            130                 135                 140

Thr Ala Asn Arg Lys Glu Arg Arg Arg Thr Gln Ser Ile Asn Ser Ala
145                 150                 155                 160

Phe Ala Glu Leu Arg Glu Cys Ile Pro Asn Val Pro Ala Asp Thr Lys
                165                 170                 175

Leu Ser Lys Ile Lys Thr Leu Arg Leu Ala Thr Ser Tyr Ile Ala Tyr
            180                 185                 190

Leu Met Asp Leu Leu Ala Lys Asp Asp Gln Asn Gly Glu Ala Glu Ala
            195                 200                 205

Phe Lys Ala Glu Ile Lys Lys Thr Asp Val Lys Glu Glu Lys Arg Lys
            210                 215                 220

Lys Glu Leu Asn Glu Ile Leu Lys Ser Thr Val Ser Ser Asn Asp Lys
225                 230                 235                 240

Lys Thr Lys Gly Arg Thr Gly Trp Pro Gln His Val Trp Ala Leu Glu
                245                 250                 255

Leu Lys Gln

<210> SEQ ID NO 6
<211> LENGTH: 176
<212> TYPE: PRT
<213> ORGANISM: Sus scrofa

<400> SEQUENCE: 6

Gly Trp Leu Gly Glu Glu Ile Gly His Pro Glu Met Ser Pro Pro Asp
1               5                   10                  15

Tyr Ser Met Ala Leu Ser Tyr Ser Pro Glu Tyr Ala Ser Gly Ala Ala
            20                  25                  30

Ser Leu Asp His Ser His Tyr Gly Gly Val Pro Pro Gly Ala Gly Pro
            35                  40                  45

Pro Gly Leu Gly Gly Pro Arg Pro Val Lys Arg Arg Gly Thr Ala Asn
            50                  55                  60

Arg Lys Glu Arg Arg Arg Thr Gln Ser Ile Asn Ser Ala Phe Ala Glu
65                  70                  75                  80

Leu Arg Glu Cys Ile Pro Asn Val Pro Ala Asp Thr Lys Leu Ser Lys
                85                  90                  95
```

```
Ile Lys Thr Leu Arg Leu Ala Thr Ser Tyr Ile Ala Tyr Leu Met Asp
        100                 105                 110

Leu Leu Ala Lys Asp Asp Gln Asn Gly Glu Ala Glu Ala Phe Lys Ala
    115                 120                 125

Glu Ile Lys Lys Thr Asp Val Lys Glu Glu Lys Arg Lys Lys Glu Leu
    130                 135                 140

Asn Glu Ile Leu Lys Ser Thr Val Ser Ser Asn Asp Lys Lys Thr Lys
145                 150                 155                 160

Gly Arg Thr Gly Trp Pro Gln His Val Trp Ala Leu Glu Leu Lys Gln
                165                 170                 175

<210> SEQ ID NO 7
<211> LENGTH: 2139
<212> TYPE: DNA
<213> ORGANISM: Sus scrofa

<400> SEQUENCE: 7
```

| | | | | |
|---|---|---|---|---|
| actagagttt | tcactcgcag | ctccaggcgg | ggtggcctcc | tccatcctcc acccctcaa | 60 |
| cccctgcacc | gggtacagag | ctctcttctg | gcaagtttct | ccccgagaga aagaggaag | 120 |
| ggagagcagg | acccagagcg | gtcacagggc | cctgggctca | ccatggccga cggagacgag | 180 |
| ggctttggcc | tggctcacac | accctggaa | ccagattcaa | aggatctacc ctgtgactca | 240 |
| aaacccgaga | gtgggctagg | ggccccagc | aagtcccgt | cgtccccgca ggccgccttc | 300 |
| acccagcagg | gcatggaagg | gatcaaggtg | ttctccatg | aaagagaact gtggctgaaa | 360 |
| tttcacgaag | tgggcacaga | aatgatcata | accaaggctg | gcaggcggat gtttcccagt | 420 |
| tacaaagtga | aggtgactgg | ccttaatccc | aaaaccaagt | acattctcct tatggacatc | 480 |
| gttcctgccg | atgaccacag | atacaagttc | gccgataata | aatggtctgt gacaggcaaa | 540 |
| gcggagcctg | ccatgccggg | ccgcctctac | gtgcacccgg | actcgccggc cactggagcg | 600 |
| cattggatgc | ggcagctcgt | ctccttccag | aaactcaagc | tcaccaacaa ccacctggac | 660 |
| ccgtttgggc | acattattct | aaattccatg | cacaaatacc | agcccagatt acacatcgtg | 720 |
| aaagcggacg | aaaataatgg | atttggctca | aaaaatactg | cattctgtac ccacgtcttt | 780 |
| cctgagacag | cgtttattgc | agtgacttcc | taccagaacc | acaagatcac caattaaag | 840 |
| atcgagaata | tccctttgc | caaggattc | cggggcagcg | atgacatgga actgcacagg | 900 |
| atgtcaagga | tgcaaagtaa | agaatatccc | gtggttccca | ggagcacagt gagacagaaa | 960 |
| gtggcctcca | accacagtcc | cttcagcagt | gagcctcgtg | ctctctccac ctcatccaac | 1020 |
| ttggggtccc | agtatcagtg | tgagaatggt | gtgtccggcc | cctcccagga cctcctgccc | 1080 |
| ccacctaacc | cgtacccact | tccccaggag | cacagccaaa | tttaccattg caccaagagg | 1140 |
| aaagatgaag | aatgttccac | cacagagcat | ccctataaga | agccctacat ggagacgtca | 1200 |
| cccagtgaag | aggacccctt | ctaccgagcc | ggctaccccc | agcagcaggg tctgggtgcc | 1260 |
| tcctaccgga | cagagtcagc | ccagcggcag | gcctgcatgt | acgccagctc cgcaccgccc | 1320 |
| agtgagccgg | tgcccagcct | ggaggacatt | agctgcaaca | cgtggcccag catgccttcc | 1380 |
| tacagcagct | gcacagtcac | caccgtgcag | cccatggaca | ggctacccta ccagcacttc | 1440 |
| tctgctcact | tcacctcggg | gccctggtc | ccccggctgg | ctggcatggc caaccacggc | 1500 |
| tccccgcagt | tgggggaggg | aatgttccag | caccagacct | ccgtggccca ccagcctgtg | 1560 |
| gtcaggcagt | gtgggcctca | gactggcctc | cagtcccgg | gcagccttca agcgtccgag | 1620 |
| ttcctgtact | ctcatggcgt | gccaaggacc | ctgtccccgc | atcagtacca ctctgctgtg | 1680 |

-continued

```
cacggggtcg gcatggttcc agagtggagt gacaacagct aaagcgaggc ctgctccttc    1740
actgacgttt ccagagggag gggagagagg gagagagaca gtcgcagaga gaacccccaag   1800 aacgagatgt cgcatttcac tccatgttca cgtctgcact tgagaagccc accctggaca   1860
ctgatgtaat cagtagcttg aaaccacaat tcaaaaaatg tgactttgtt ttgtctcaaa   1920
acttaaaaaa tcgacaagag gcgatgagtc ccaaccccc ctaccccgcc cccaccatcc    1980
accaccacca cagtcatcaa ctggccacat tcacacgacc tccagatgcc ctccgggatt   2040
ccttcttttg gtctccagaa agtcttgcct catggagtgt tttatcccaa aacatagatg   2100
gagtcattcc ctgtcttggt gttactgttg acattgtta                          2139
```

<210> SEQ ID NO 8
<211> LENGTH: 520
<212> TYPE: PRT
<213> ORGANISM: Sus scrofa

<400> SEQUENCE: 8

```
Met Ala Asp Gly Asp Glu Gly Phe Gly Leu Ala His Thr Pro Leu Glu
1               5                   10                  15

Pro Asp Ser Lys Asp Leu Pro Cys Asp Ser Lys Pro Glu Ser Gly Leu
            20                  25                  30

Gly Ala Pro Ser Lys Ser Pro Ser Pro Gln Ala Ala Phe Thr Gln
        35                  40                  45

Gln Gly Met Glu Gly Ile Lys Val Phe Leu His Glu Arg Glu Leu Trp
    50                  55                  60

Leu Lys Phe His Glu Val Gly Thr Glu Met Ile Ile Thr Lys Ala Gly
65                  70                  75                  80

Arg Arg Met Phe Pro Ser Tyr Lys Val Lys Val Thr Gly Leu Asn Pro
                85                  90                  95

Lys Thr Lys Tyr Ile Leu Leu Met Asp Ile Val Pro Ala Asp Asp His
            100                 105                 110

Arg Tyr Lys Phe Ala Asp Asn Lys Trp Ser Val Thr Gly Lys Ala Glu
        115                 120                 125

Pro Ala Met Pro Gly Arg Leu Tyr Val His Pro Asp Ser Pro Ala Thr
    130                 135                 140

Gly Ala His Trp Met Arg Gln Leu Val Ser Phe Gln Lys Leu Lys Leu
145                 150                 155                 160

Thr Asn Asn His Leu Asp Pro Phe Gly His Ile Ile Leu Asn Ser Met
                165                 170                 175

His Lys Tyr Gln Pro Arg Leu His Ile Val Lys Ala Asp Glu Asn Asn
            180                 185                 190

Gly Phe Gly Ser Lys Asn Thr Ala Phe Cys Thr His Val Phe Pro Glu
        195                 200                 205

Thr Ala Phe Ile Ala Val Thr Ser Tyr Gln Asn His Lys Ile Thr Gln
    210                 215                 220

Leu Lys Ile Glu Asn Asn Pro Phe Ala Lys Gly Phe Arg Gly Ser Asp
225                 230                 235                 240

Asp Met Glu Leu His Arg Met Ser Arg Met Gln Ser Lys Glu Tyr Pro
                245                 250                 255

Val Val Pro Arg Ser Thr Val Arg Gln Lys Val Ala Ser Asn His Ser
            260                 265                 270

Pro Phe Ser Ser Glu Pro Arg Ala Leu Ser Thr Ser Ser Asn Leu Gly
        275                 280                 285
```

Ser Gln Tyr Gln Cys Glu Asn Gly Val Ser Gly Pro Ser Gln Asp Leu
    290                 295                 300

Leu Pro Pro Asn Pro Tyr Pro Leu Pro Gln Glu His Ser Gln Ile
305                 310                 315                 320

Tyr His Cys Thr Lys Arg Lys Ala Asp Glu Glu Cys Ser Thr Thr Glu
                325                 330                 335

His Pro Tyr Lys Lys Pro Tyr Met Glu Thr Ser Pro Ser Glu Glu Asp
                340                 345                 350

Pro Phe Tyr Arg Ala Gly Tyr Pro Gln Gln Gln Gly Leu Gly Ala Ser
                355                 360                 365

Tyr Arg Thr Glu Ser Ala Gln Arg Gln Ala Cys Met Tyr Ala Ser Ser
370                 375                 380

Ala Pro Pro Ser Glu Pro Val Pro Ser Leu Glu Asp Ile Ser Cys Asn
385                 390                 395                 400

Thr Trp Pro Ser Met Pro Ser Tyr Ser Ser Cys Thr Val Thr Thr Val
                405                 410                 415

Gln Pro Met Asp Arg Leu Pro Tyr Gln His Phe Ser Ala His Phe Thr
                420                 425                 430

Ser Gly Pro Leu Val Pro Arg Leu Ala Gly Met Ala Asn His Gly Ser
                435                 440                 445

Pro Gln Leu Gly Glu Gly Met Phe Gln His Gln Thr Ser Val Ala His
450                 455                 460

Gln Pro Val Val Arg Gln Cys Gly Pro Gln Thr Gly Leu Gln Ser Pro
465                 470                 475                 480

Gly Ser Leu Gln Ala Ser Glu Phe Leu Tyr Ser His Gly Val Pro Arg
                485                 490                 495

Thr Leu Ser Pro His Gln Tyr His Ser Ala Val His Gly Val Gly Met
                500                 505                 510

Val Pro Glu Trp Ser Asp Asn Ser
                515                 520

<210> SEQ ID NO 9
<211> LENGTH: 519
<212> TYPE: PRT
<213> ORGANISM: Sus scrofa

<400> SEQUENCE: 9

Met Ala Asp Gly Asp Glu Gly Phe Gly Leu Ala His Thr Pro Leu Glu
1               5                   10                  15

Pro Asp Ser Lys Asp Leu Pro Cys Asp Ser Lys Pro Glu Ser Gly Leu
                20                  25                  30

Gly Ala Pro Ser Lys Ser Pro Ser Ser Pro Gln Ala Ala Phe Thr Gln
                35                  40                  45

Gln Gly Met Glu Gly Ile Lys Val Phe Leu His Glu Arg Glu Leu Trp
    50                  55                  60

Leu Lys Phe His Glu Val Gly Thr Glu Met Ile Ile Thr Lys Ala Gly
65                  70                  75                  80

Arg Arg Met Phe Pro Ser Tyr Lys Val Lys Val Thr Gly Leu Asn Pro
                85                  90                  95

Lys Thr Lys Tyr Ile Leu Leu Met Asp Ile Val Pro Ala Asp Asp His
                100                 105                 110

Arg Tyr Lys Phe Ala Asp Asn Lys Trp Ser Val Thr Gly Lys Ala Glu
            115                 120                 125

Pro Ala Met Pro Gly Arg Leu Tyr Val His Pro Asp Ser Pro Ala Thr
130                 135                 140

```
Gly Ala His Trp Met Arg Gln Leu Val Ser Phe Gln Lys Leu Lys Leu
145                 150                 155                 160

Thr Asn Asn His Leu Asp Pro Phe Gly His Ile Ile Leu Asn Ser Met
            165                 170                 175

His Lys Tyr Gln Pro Arg Leu His Ile Val Lys Ala Asp Glu Asn Asn
        180                 185                 190

Gly Phe Gly Ser Lys Asn Thr Ala Phe Cys Thr His Val Phe Pro Glu
    195                 200                 205

Thr Ala Phe Ile Ala Val Thr Ser Tyr Gln Asn His Lys Ile Thr Gln
210                 215                 220

Leu Lys Ile Glu Asn Asn Pro Phe Ala Lys Gly Phe Arg Gly Ser Asp
225                 230                 235                 240

Asp Met Glu Leu His Arg Met Ser Arg Met Gln Ser Lys Glu Tyr Pro
            245                 250                 255

Val Val Pro Arg Ser Thr Val Arg Gln Lys Val Ala Ser Asn His Ser
        260                 265                 270

Pro Phe Ser Ser Glu Pro Arg Ala Leu Ser Thr Ser Ser Asn Leu Gly
    275                 280                 285

Ser Gln Tyr Gln Cys Glu Asn Gly Val Ser Gly Pro Ser Gln Asp Leu
290                 295                 300

Leu Pro Pro Asn Pro Tyr Pro Leu Pro Gln His Ser Gln Ile
305                 310                 315                 320

Tyr His Cys Thr Lys Arg Lys Asp Glu Glu Cys Ser Thr Thr Glu His
            325                 330                 335

Pro Tyr Lys Lys Pro Tyr Met Glu Thr Ser Pro Ser Glu Glu Asp Pro
        340                 345                 350

Phe Tyr Arg Ala Gly Tyr Pro Gln Gln Gln Gly Leu Gly Ala Ser Tyr
    355                 360                 365

Arg Thr Glu Ser Ala Gln Arg Gln Ala Cys Met Tyr Ala Ser Ser Ala
370                 375                 380

Pro Pro Ser Glu Pro Val Pro Ser Leu Glu Asp Ile Ser Cys Asn Thr
385                 390                 395                 400

Trp Pro Ser Met Pro Ser Tyr Ser Ser Cys Thr Val Thr Thr Val Gln
            405                 410                 415

Pro Met Asp Arg Leu Pro Tyr Gln His Phe Ser Ala His Phe Thr Ser
        420                 425                 430

Gly Pro Leu Val Pro Arg Leu Ala Gly Met Ala Asn His Gly Ser Pro
    435                 440                 445

Gln Leu Gly Glu Gly Met Phe Gln His Gln Thr Ser Val Ala His Gln
450                 455                 460

Pro Val Val Arg Gln Cys Gly Pro Gln Thr Gly Leu Gln Ser Pro Gly
465                 470                 475                 480

Ser Leu Gln Ala Ser Glu Phe Leu Tyr Ser His Gly Val Pro Arg Thr
            485                 490                 495

Leu Ser Pro His Gln Tyr His Ser Ala Val His Gly Val Gly Met Val
        500                 505                 510

Pro Glu Trp Ser Asp Asn Ser
        515
```

<210> SEQ ID NO 10
<211> LENGTH: 324
<212> TYPE: PRT
<213> ORGANISM: Homo sapiens

<400> SEQUENCE: 10

```
Met Phe Pro Ser Pro Ala Leu Thr Pro Thr Pro Phe Ser Val Lys Asp
1               5                   10                  15

Ile Leu Asn Leu Glu Gln Gln Gln Arg Ser Leu Ala Ala Ala Gly Glu
            20                  25                  30

Leu Ser Ala Arg Leu Glu Ala Thr Leu Ala Pro Ser Ser Cys Met Leu
        35                  40                  45

Ala Ala Phe Lys Pro Glu Ala Tyr Ala Gly Pro Glu Ala Ala Ala Pro
    50                  55                  60

Gly Leu Pro Glu Leu Arg Ala Glu Leu Gly Arg Ala Pro Ser Pro Ala
65                  70                  75                  80

Lys Cys Ala Ser Ala Phe Pro Ala Ala Pro Ala Phe Tyr Pro Arg Ala
                85                  90                  95

Tyr Ser Asp Pro Asp Pro Ala Lys Asp Pro Arg Ala Glu Lys Lys Glu
            100                 105                 110

Leu Cys Ala Leu Gln Lys Ala Val Glu Leu Glu Lys Thr Glu Ala Asp
        115                 120                 125

Asn Ala Glu Arg Pro Arg Ala Arg Arg Arg Lys Pro Arg Val Leu
130                 135                 140

Phe Ser Gln Ala Gln Val Tyr Glu Leu Glu Arg Arg Phe Lys Gln Gln
145                 150                 155                 160

Arg Tyr Leu Ser Ala Pro Glu Arg Asp Gln Leu Ala Ser Val Leu Lys
                165                 170                 175

Leu Thr Ser Thr Gln Val Lys Ile Trp Phe Gln Asn Arg Arg Tyr Lys
            180                 185                 190

Cys Lys Arg Gln Arg Gln Asp Gln Thr Leu Glu Leu Val Gly Leu Pro
        195                 200                 205

Pro Pro Pro Pro Pro Ala Arg Ile Ala Val Pro Val Leu Val
210                 215                 220

Arg Asp Gly Lys Pro Cys Leu Gly Asp Ser Ala Pro Tyr Ala Pro Ala
225                 230                 235                 240

Tyr Gly Val Gly Leu Asn Pro Tyr Gly Tyr Asn Ala Tyr Pro Ala Tyr
                245                 250                 255

Pro Gly Tyr Gly Gly Ala Ala Cys Ser Pro Gly Tyr Ser Cys Thr Ala
            260                 265                 270

Ala Tyr Pro Ala Gly Pro Ser Pro Ala Gln Pro Ala Thr Ala Ala Ala
        275                 280                 285

Asn Asn Asn Phe Val Asn Phe Gly Val Gly Asp Leu Asn Ala Val Gln
290                 295                 300

Ser Pro Gly Ile Pro Gln Ser Asn Ser Gly Val Ser Thr Leu His Gly
305                 310                 315                 320

Ile Arg Ala Trp
```

<210> SEQ ID NO 11
<211> LENGTH: 1632
<212> TYPE: DNA
<213> ORGANISM: Homo sapiens

<400> SEQUENCE: 11

| | | | | |
|---|---|---|---|---|
| gacgggtgcg | cgggcgggcg | gcggcaccat | gcagggaagc | tgccaggggc | cgtgggcagc | 60 |
| gccgctttct | gccgcccacc | tggcgctgtg | agactggcgc | tgccaccatg | ttccccagcc | 120 |
| ctgctctcac | gccacgcccc | ttctcagtca | aagacatcct | aaacctggaa | cagcagcagc | 180 |
| gcagcctggc | tgccgccgga | gagctctctg | cccgcctgga | ggcgaccctg | gcgccctcct | 240 |

```
cctgcatgct ggccgccttc aagccagagg cctacgctgg gcccgaggcg gctgcgccgg      300
gcctcccaga gctgcgcgca gagctgggcc gcgcgccttc accggccaag tgtgcgtctg      360
cctttcccgc cgcccccgcc ttctatccac gtgcctacag cgaccccgac ccagccaagg      420
accctagagc cgaaaagaaa gagctgtgcg cgctgcagaa ggcggtggag ctggagaaga      480
cagaggcgga caacgcggag cggccccggg cgcgacggcg gaggaagccg cgcgtgctct      540
tctcgcaggc gcaggtctat gagctggagc ggcgcttcaa gcagcagcgg tacctgtcgg      600
cccccgaacg cgaccagctg ccagcgtgc tgaaactcac gtccacgcag gtcaagatct      660
ggttccagaa ccggcgctac aagtgcaagc ggcagcggca ggaccagact ctggagctgg      720
tggggctgcc cccgccgccg ccgccgcctg cccgcaggat cgcggtgcca gtgctggtgc      780
gcgatggcaa gccatgccta ggggactcgg cgccctacgc gcctgcctac ggcgtgggcc      840
tcaatcccta cggttataac gcctacccca cctatccggg ttacggcggc gcggcctgca      900
gccctggcta cagctgcact gccgcttacc ccgccgggcc ttccccagcg cagccggcca      960
ctgccgccgc caacaacaac ttcgtgaact tcggcgtcgg ggacttgaat gcggttcaga     1020
gccccgggat tccgcagagc aactcgggag tgtccacgct gcatggtatc cgagcctggt     1080
agggaaggga cccgcgtggc gcgaccctga ccgatcccac tcaacagct ccctgactct      1140
cggggggaga aggggctccc aacatgaccc tgagtcccct ggattttgca ttcactcctg     1200
cggagaccta ggaactttttt ctgtcccacg cgcgtttgtt cttgcgcacg ggagagtttg    1260
tggcggcgat tatgcagcgt gcaatgagtg atcctgcagc ctggtgtctt agctgtcccc    1320
ccaggagtgc cctccgagag tccatgggca ccccggttg gaactgggac tgagctcggg    1380
cacgcagggc ctgagatctg gccgcccatt ccgcgagcca gggccgggcg cccgggcctt    1440
tgctatctcg ccgtcgcccg cccacgcacc cacccgtatt tatgttttta cctattgctg    1500
taagaaatga cgatccccctt cccattaaag agagtgcgtt gaaaaaaaaa aaaaaaaaaa    1560
aaaaaaaaaa aaaaaaaaaa aaaaaaaaaa aaaaaaaaaa aaaaaaaaaa aaaaaaaaaa    1620
aaaaaaaaaa aa                                                         1632

<210> SEQ ID NO 12
<211> LENGTH: 2351
<212> TYPE: DNA
<213> ORGANISM: Homo sapiens

<400> SEQUENCE: 12
agctgtacat ggagatcttg ctgggaaaat ccgcttgctc ccctcacgtc gtccagccca       60
ggagaaccac cgccgtcacc ccggagcttc ctcggccacc gcgcagagcc ctccgagagc      120
ccgagccgcg gtcttcgagc tccaaggctc attcagggcc ccagatcctt gccccgaaag      180
gagaggatct gagaaaatgg atgcactgag acctctctga aaaccctccg agagagcgcg      240
agaggagcga ggacacgtta ctcgcagcta aaatcacatt taaggaccaa acaacaaca      300
accaaaaatt tcattaaaac aataagcgcc caagaaccca gatcgggctg gtgggggag      360
gggaagaggc gggaagggga gggtcgcacg gaggtagctt tgcagtgagc agtcgacccc     420
gccgcccccc ggcacagctg gaccggctcc tccagccgcg gctcagactc gcccctggat    480
tccgggttag cttcggtgcc aggaccgcgg cccgggcttg gattcccgag actccgcgta    540
ccagcctcgc gggagccccg gcacctttgt atgagcacga gaggattctg cctccgcgca    600
gcagcccggg aagcaggagc cgaagcgcgg gccgtgagc aaggcgggaa ccggaggcgg     660
cggcggcggc ggccaggggc gcacggtgcc aggaccagct cgccgcgccc catggggagc    720
```

-continued

```
cggcggccgc agcgctgctg aggcgggccc ggctggccag gcgggggggac ggggcccggg      780 ctgcagcagc ccctctgcg gctgccgggc gggcccgggc gccgggggc tgggggggtgg       840 ggggtggggg aggacgccga gcgctgaggc aggggcccgg gccgagggcg cggcggggct      900
gcgcgcacgc tggggcgcgt ggaggggcgc ggagggcgaa atgagtctgg taggtggttt      960
tccccaccac ccggtggtgc accacgaggg ctaccgtttt gccgccgccg ccgccgcagc     1020
tgccgccgcc gccgccagcc gctgcagcca tgaggagaac ccctacttcc atggctggct     1080
catcggccac cccgagatgt cgccccccga ctacagcatg gccctgtcct acagccccga     1140
gtatgccagc ggcgccgccg gcctggacca ctcccattac ggggggggtgc cgccgggcgc     1200 cgggcccccg ggcctggggg ggccgcgccc ggtgaagcgc cgaggcaccg ccaaccgcaa     1260
ggagcggcgc aggactcaga gcatcaacag cgccttcgcc gaactgcgcg agtgcatccc     1320
caacgtaccc gccgacacca aactctccaa aatcaagacc ctgcgcctgg ccaccagcta     1380
catcgcctac ctcatggacc tgctggccaa ggacgaccag aatggcgagg cggaggcctt     1440
caaggcagag atcaagaaga ccgacgtgaa agaggagaag aggaagaagg agctgaacga     1500
aatcttgaaa agcacagtga gcagcaacga caagaaaacc aaaggccgga cgggctggcc     1560
gcagcacgtc tgggccctgg agctcaagca gtgaggagga ggagaaggag gaggaggaga     1620
gcgcgagtga gcaggggcca aggcgccaga tgcagaccca ggactccgga aaagccgtcc     1680
gcgctccgct ctgaggactc cttgcatttg gaatcatccg gtttatttat gtgcaatttc     1740
cttcccctct cttttgacccc ctttgaggca tctgctcccc gtctcccct ccaaaaaaaa     1800 agtggatatt tgaagaaaag cattccatat tttaatacga agaggacact cccgtgtggt     1860
aagggatccc gtcgtctcat agattctgtg tgcgtgaatg ttccctcttg gctgtgtaga     1920
caccagcgtt gccccccgcc aacctactca accccttcca gataaagaca gtgggcacta     1980
gtgcgtttgt gaagtgtatc tttaatactt ggcctttgga tataaatatt cctgggtatt     2040 ataaagttttt atttcaaagc agaaaacagg gccgctaaca tttccgttgg ggtcggtatc     2100
tagtgctatc cattcatctg tggtcgttcc ctctttgaag atgtttccaa cagccacttg     2160
ttttgtgcac ttccgtcctc taaaactaaa tggaatttaa ttaatattga aggtgtaaac     2220
gttgtaagta ttcaataaac cactgtgttt tttttttaca aaaaccttaa tcttttaatg     2280
gctgatacct caaaagagtt ttgaaaacaa agctgttata cttgttttcg taatatttaa     2340
aatattcaga a                                                          2351
```

<210> SEQ ID NO 13
<211> LENGTH: 217
<212> TYPE: PRT
<213> ORGANISM: Homo sapiens

<400> SEQUENCE: 13

```
Met Ser Leu Val Gly Gly Phe Pro His Pro Val Val His Glu
1               5                   10                  15

Gly Tyr Pro Phe Ala Ala Ala Ala Ala Ala Ala Ala Ala Ala Ala
                20                  25                  30

Ser Arg Cys Ser His Glu Glu Asn Pro Tyr Phe His Gly Trp Leu Ile
            35                  40                  45

Gly His Pro Glu Met Ser Pro Pro Asp Tyr Ser Met Ala Leu Ser Tyr
        50                  55                  60

Ser Pro Glu Tyr Ala Ser Gly Ala Ala Gly Leu Asp His Ser His Tyr
65                  70                  75                  80
```

```
Gly Gly Val Pro Pro Gly Ala Gly Pro Pro Gly Leu Gly Gly Pro Arg
                 85                  90                  95

Pro Val Lys Arg Arg Gly Thr Ala Asn Arg Lys Glu Arg Arg Thr
            100                 105                 110

Gln Ser Ile Asn Ser Ala Phe Ala Glu Leu Arg Glu Cys Ile Pro Asn
        115                 120                 125

Val Pro Ala Asp Thr Lys Leu Ser Lys Ile Lys Thr Leu Arg Leu Ala
    130                 135                 140

Thr Ser Tyr Ile Ala Tyr Leu Met Asp Leu Leu Ala Lys Asp Asp Gln
145                 150                 155                 160

Asn Gly Glu Ala Glu Ala Phe Lys Ala Glu Ile Lys Lys Thr Asp Val
                165                 170                 175

Lys Glu Glu Lys Arg Lys Lys Glu Leu Asn Glu Ile Leu Lys Ser Thr
            180                 185                 190

Val Ser Ser Asn Asp Lys Lys Thr Lys Gly Arg Thr Gly Trp Pro Gln
        195                 200                 205

His Val Trp Ala Leu Glu Leu Lys Gln
    210                 215

<210> SEQ ID NO 14
<211> LENGTH: 3748
<212> TYPE: DNA
<213> ORGANISM: Homo sapiens

<400> SEQUENCE: 14
ttcagagaga gagagagagg gagagagagt gagagagact gactcttacc tcgaatccgg      60
gaactttaat cctgaaagct gcgctcagaa aggacttcga ccattcactg ggcttccaac     120
tttccctccc tgggggtgta aggaggagc gggggcactga gattatatgg ttgccggtgc     180
tcttggaggc tattttgtgt tctttggcgc ttgccaactg ggaagtattt agggagagca     240
agcgcacagc agaggaggtg tgtgttggag gtgggcagtc gccgcggagg ctccagcggt     300
aggtgcgccc tagtaggcag cagtagccgc tattctgggt aagcagtaaa ccccgcataa     360
accccggagc caccatgcct gctccccgc ctcaccgccg gcttccctgc taggagcagc     420
agaggatgtg gtaatgcac cggcttcacc gaacagagc agaaccttgc gcgggcacag     480
ggccctgggc gcaccatggc cgacgcagac gagggctttg gcctggcgca cacgcctctg     540
gagcctgacg caaagacct gccctgcgat tcgaaacccg agagcgcgct cggggccccc     600
agcaagtccc cgtcgtcccc gcaggccgcc ttcacccagc agggcatgga gggaatcaaa     660
gtgtttctcc atgaaagaga actgtggcta aaattccacg aagtgggcac ggaaatgatc     720
ataaccaagg ctggaaggcg gatgtttccc agttacaaag tgaaggtgac gggccttaat     780
cccaaaacga agtacattct tctcatggac attgtacctg ccgacgatca cagatacaaa     840
ttcgcagata taaatggtc tgtgacgggc aaagctgagc cgccatgcc tggccgcctg     900
tacgtgcacc cagactcccc cgccaccggg gcgcattgga tgaggcagct cgtctccttc     960
cagaaactca agctcaccaa caaccacctg gacccatttg gcatattat tctaaattcc    1020
atgcacaaat accagcctag attacacatc gtgaaagcgg atgaaaataa tggatttggc    1080
tcaaaaaata cagcgttctg cactcacgtc tttcctgaga ctgcgtttat agcagtgact    1140
tcctaccaga accacaagat cacgcaatta aagattgaga ataatccctt tgccaaagga    1200
tttcggggca gtgatgacat ggagctgcac agaatgtcaa gaatgcaaag taaagaatat    1260
cccgtggtcc ccaggagcac cgtgaggcaa aaagtggcct ccaaccacag tcctttcagc    1320
```

```
agcgagtctc gagctctctc cacctcatcc aatttggggt cccaatacca gtgtgagaat    1380
ggtgttttccg gcccctccca ggacctcctg cctccaccca acccataccc actgccccag   1440
gagcatagcc aaatttacca ttgtaccaag aggaaagagg aagaatgttc caccacagac    1500
catccctata agaagcccta catggagaca tcacccagtg aagaagattc cttctaccgc    1560
tctagctatc cacagcagca gggcctgggt gcctcctaca ggacagagtc ggcacagcgg    1620
caagcttgca tgtatgccag ctctgcgccc cccagcgagc ctgtgcccag cctagaggac    1680
atcagctgca acacgtggcc aagcatgcct tcctacagca gctgcaccgt caccaccgtg    1740
cagcccatgg acaggctacc ctaccagcac ttctccgctc acttcacctc ggggcccctg    1800
gtccctcggc tggctggcat ggccaaccat ggctccccac agctgggaga gggaatgttc    1860
cagcaccaga cctccgtggc ccaccagcct gtggtcaggc agtgtgggcc tcagactggc    1920
ctgcagtccc ctggcaccct tcagcccccct gagttcctct actctcatgg cgtgccaagg    1980
actctatccc ctcatcagta ccactctgtg cacggagttg gcatggtgcc agagtggagc    2040
gacaatagct aaagtgaggc ctgcttcaca acagacattt cctagagaaa gagagagaga    2100
gaggagaaag agagagaagg agagagacag tagccaagag aaccccacag acaagatttt    2160
tcatttcacc caatgttcac atctgcactc aaggtcgctg gatgctgatc taatcagtag    2220
cttgaaacca aattttaaa aatgtgactt tcttgttttg tctcaaaact taaaaaaaca    2280
aacacaaaaa gatgagtccc acccccacct accaccacac ccatcaacca gccacattca    2340
cgctactccc cagatctctt cccccattcc ttcttttggg ctctagaaag tcttgcctca    2400
ttgagtgttt ttccctagtg cgtagttgga gtctgtccct gtcttggtgt taatgttgac    2460
attgttatat aataaatgat aatatatttt tttctttcaa ttttcttaat gggacccagt    2520
cccttatttg gggggaggtc tgaggcaagt atatttcaaa atatgtactt gcgggattcc    2580
cttcaagtaa accatccctg aaacctaaat tcacgtttcc ccttgactaa gaaaagcacc    2640
tacctctgcc atgtgatgtt tctgaaaagc ctctgtatgt ccccatttgc tttggttttg    2700
tcctgccttc tccaatatca cgtgctcagt tttgcctcta cttacccatg gagtcaggat    2760
aacactgacg ctccctggca tcctatctta ctcagcccta ccatcttgcc agctctgtct    2820
ttccagctgt ctgtcgctaa aacgtggcct atagcttccc ttccggaaag cttgctttga    2880
aaaacttaaa aagcccccgt ttacatgtag gcaggactgt gataacagtg caagctctgt    2940
gttgacaaga gttgtggaca aaaagccaaa ataaatattc ttcctgatta aaaaaatttt    3000
ttttgaaaaa aacaaggcca gccccaacct tccaaacctc catcaccaac aacccaaact    3060
ggatgtcaag caaaatgcac aattcctaca gaagaggcaa gacacagtca ccaatgatat    3120
ctcgccaaag aaaccacgcc cacaccaatg ccgacacaaa actgtgttta ctgaaagccg    3180
aaaacagtat taaaaaaagt gtgtaagtaa agtgttatgg tagggttctt cagatgtaat    3240
attttactgg tactatttat ttataaatag gaattctaat taagtaataa catgaaatga    3300
aacccagcat aggagctggc caagagcttt taattttatt gatactcaaa accaagtttg    3360
tgttttttg tttttttttg tttttttcct ctttcgaatg tgctttgctt ttttttgatta    3420
aaaagaattt tttttttcctt tttataaac agaccctaat aaagagaaca gggtaagatg    3480
tgaggctgag tgtgtttaag tacgtgagag agtgtgagtg tgtttgtaag tgagtgtccc    3540
tatgcgatta tgtctcttta cgttgctaag ggggagggt gaggattaag tactcgtgcc    3600
ttatatttgt gtgccaatta atgcctaata aataccatgt gcttaaacaa gtaaaaaaaa    3660
```

-continued

```
aaaaaaaaaa aaaaaaaaaa aaaaaaaaaa aaaaaaaaaa aaaaaaaaaa aaaaaaaaaa      3720
aaaaaaaaaa aaaaaaaaaa aaaaaaaa                                         3748

<210> SEQ ID NO 15
<211> LENGTH: 518
<212> TYPE: PRT
<213> ORGANISM: Homo sapiens

<400> SEQUENCE: 15

Met Ala Asp Ala Asp Glu Gly Phe Gly Leu Ala His Thr Pro Leu Glu
1               5                   10                  15

Pro Asp Ala Lys Asp Leu Pro Cys Asp Ser Lys Pro Glu Ser Ala Leu
            20                  25                  30

Gly Ala Pro Ser Lys Ser Pro Ser Pro Gln Ala Ala Phe Thr Gln
        35                  40                  45

Gln Gly Met Glu Gly Ile Lys Val Phe Leu His Glu Arg Glu Leu Trp
    50                  55                  60

Leu Lys Phe His Glu Val Gly Thr Glu Met Ile Ile Thr Lys Ala Gly
65                  70                  75                  80

Arg Arg Met Phe Pro Ser Tyr Lys Val Lys Val Thr Gly Leu Asn Pro
                85                  90                  95

Lys Thr Lys Tyr Ile Leu Leu Met Asp Ile Val Pro Ala Asp Asp His
            100                 105                 110

Arg Tyr Lys Phe Ala Asp Asn Lys Trp Ser Val Thr Gly Lys Ala Glu
        115                 120                 125

Pro Ala Met Pro Gly Arg Leu Tyr Val His Pro Asp Ser Pro Ala Thr
    130                 135                 140

Gly Ala His Trp Met Arg Gln Leu Val Ser Phe Gln Lys Leu Lys Leu
145                 150                 155                 160

Thr Asn Asn His Leu Asp Pro Phe Gly His Ile Ile Leu Asn Ser Met
                165                 170                 175

His Lys Tyr Gln Pro Arg Leu His Ile Val Lys Ala Asp Glu Asn Asn
            180                 185                 190

Gly Phe Gly Ser Lys Asn Thr Ala Phe Cys Thr His Val Phe Pro Glu
        195                 200                 205

Thr Ala Phe Ile Ala Val Thr Ser Tyr Gln Asn His Lys Ile Thr Gln
    210                 215                 220

Leu Lys Ile Glu Asn Asn Pro Phe Ala Lys Gly Phe Arg Gly Ser Asp
225                 230                 235                 240

Asp Met Glu Leu His Arg Met Ser Arg Met Gln Ser Lys Glu Tyr Pro
                245                 250                 255

Val Val Pro Arg Ser Thr Val Arg Gln Lys Val Ala Ser Asn His Ser
            260                 265                 270

Pro Phe Ser Ser Glu Ser Arg Ala Leu Ser Thr Ser Ser Asn Leu Gly
        275                 280                 285

Ser Gln Tyr Gln Cys Glu Asn Gly Val Ser Gly Pro Ser Gln Asp Leu
    290                 295                 300

Leu Pro Pro Pro Asn Pro Tyr Pro Leu Pro Gln Glu His Ser Gln Ile
305                 310                 315                 320

Tyr His Cys Thr Lys Arg Lys Glu Glu Glu Cys Ser Thr Thr Asp His
                325                 330                 335

Pro Tyr Lys Lys Pro Tyr Met Glu Thr Ser Pro Ser Glu Glu Asp Ser
            340                 345                 350
```

```
Phe Tyr Arg Ser Ser Tyr Pro Gln Gln Gly Leu Gly Ala Ser Tyr
            355                 360             365

Arg Thr Glu Ser Ala Gln Arg Gln Ala Cys Met Tyr Ala Ser Ser Ala
    370             375             380

Pro Pro Ser Glu Pro Val Pro Ser Leu Glu Asp Ile Ser Cys Asn Thr
385             390             395             400

Trp Pro Ser Met Pro Ser Tyr Ser Ser Cys Thr Val Thr Thr Val Gln
            405             410             415

Pro Met Asp Arg Leu Pro Tyr Gln His Phe Ser Ala His Phe Thr Ser
            420             425             430

Gly Pro Leu Val Pro Arg Leu Ala Gly Met Ala Asn His Gly Ser Pro
            435             440             445

Gln Leu Gly Glu Gly Met Phe Gln His Gln Thr Ser Val Ala His Gln
    450             455             460

Pro Val Val Arg Gln Cys Gly Pro Gln Thr Gly Leu Gln Ser Pro Gly
465             470             475             480

Thr Leu Gln Pro Pro Glu Phe Leu Tyr Ser His Gly Val Pro Arg Thr
            485             490             495

Leu Ser Pro His Gln Tyr His Ser Val His Gly Val Gly Met Val Pro
            500             505             510

Glu Trp Ser Asp Asn Ser
            515
```

HUMANIZED HEART MUSCLE

CLAIM OF PRIORITY

This is a U.S. National Stage Filing under 35 U.S.C. § 371 of International Application No. PCT/US2016/040431, filed Jun. 30, 2016 and published as WO 2017/004388 on 5 Jan. 2017, which application claims the benefit of priority of U.S. Provisional Patent Application No. 62/187,040, filed 30 Jun. 2015, the benefit of priority of which is claimed hereby, and which is incorporated by reference herein in its entirety.

BACKGROUND OF THE INVENTION

Congenital heart disease (CHD) afflicts approximately 1% of all live births and has considerable morbidity and mortality (1-5). Cardiovascular disease in the number one cause of death worldwide and it has been the most common cause of death in the United States each year since 1900. Today, one in every three adults is living with cardiovascular disease. Finally, congenital heart defects are the most common form of birth defect in the general population and it contributes to advanced or end stage heart failure in the pediatric and adult population. Congenital Heart Disease and other cardiovascular diseases can progress to heart failure. The only cure for end stage heart failure is cardiac transplantation, but, due to the shortage of organs for transplantation, relatively few patients receive such lifesaving therapy. Patients that do receive a heart transplant, require medications to prevent rejection of the heart and these medications often have long term side effects that also limit survival

SUMMARY OF THE INVENTION

Described herein is the development of NKX2-5/HANDII/TBX5 knockout pigs or other animals, such as cow or goat, as hosts for production of personalized human/humanized cardiac muscle tissue/cardiac muscle cells for clinical applications.

NKX2-5/HANDII/TBX5 null porcine embryos have been generated using gene editing technologies and we have used human stem cells to produce human-animal chimeras. Performing multiplex gene edits for NKX2-5/HANDII/TBX5 provide a permissive niche for the repopulation of the heart using human cells with pluripotent capacity, to yield humanized cardiac cells and/or tissues (including organs, such as the heart).

One embodiment provides a non-human animal cell, morula or blastocyst wherein the genome carries a mutation in both alleles of the NKX2-5 gene. HANDII gene, TBX5 gene or a combination thereof such that the non-human animal cell, morula or blastocyst lacks functional NKX2-5 protein. HANDII protein, TBX5 protein or a combination thereof. In one embodiment, the mutation is a deletion of the NKX2-5 gene, HANDII gene, TBX5 gene or a combination thereof. In another embodiment, the non-human animal cell, morula or blastocyst is a porcine, bovine, equine or goat.

One embodiment provides a chimeric non-human animal morula or blastocyst expressing human NKX2-5, HANDII, TBX5 or a combination thereof and lacking expression of non-human animal NKX2-5, HANDII. TBX5 or a combination thereof. In one embodiment, the non-human animal produces humanized cardiac cells and/or tissue.

One embodiment provides a chimeric pig expressing exogenous pig NKX2-5, HANDII, TBX5 or a combination thereof and lacking expression of endogenous pig NKX2-5, HANDII, TBX5 or a combination thereof (a pig-pig chimera). In one embodiment, the non-human animal is a porcine, bovine, equine or goat.

One embodiment provides a method for producing a chimeric non-human animal expressing a human NKX2-5 gene, HANDII gene, TBX5 gene or a combination thereof comprising: a) generating a NKX2-5, HANDII. TBX5 or a combination thereof null non-human animal cell, wherein both copies of the non-human NKX2-5 gene, HANDII gene, TBX5 gene or a combination thereof gene carry a mutation that prevents production of functional NKX2-5 protein, HANDII protein, TBX5 protein or combination thereof; b) creating a NKX2-5. HANDII, TBX5 or a combination thereof null non-human morula or blastocyst by somatic cell nuclear transfer comprising fusing a nucleus from said NKX2-5, HANDI, TBX5 or a combination thereof null non-human cell of a) into an enucleated non-human oocyte and activating said oocyte to divide so as to form a NKX2-5, HANDII, TBX5 or a combination thereof null non-human morula or blastocyst; c) introducing human stem cells into the non-human NKX2-5, HANDII, TBX5 or a combination thereof null morula or blastocyst of b); and d) implanting said morula or blastocyst from c) into a pseudopregnant surrogate non-human animal to generate a chimeric non-human animal expressing human NKX2-5, HANDII, TBX5 or a combination thereof.

Another embodiment provides a method for producing a chimeric pig expressing an exogenous NKX2-5 gene, HANDII gene, TBX5 gene or a combination thereof comprising: a) generating a NKX2-5, HANDII, TBX5 or a combination thereof null pig cell, wherein both copies of the endogenous pig MYF5 gene. MYOD gene, MRF4 gene or a combination thereof gene carry a mutation that prevents production of functional endogenous pig MYF5 protein. MYOD protein, MRF4 protein or combination thereof; b) creating a NKX2-5, HANDII, TBX5 or a combination thereof null pig morula or blastocyst by somatic cell nuclear transfer comprising fusing a nucleus from said NKX2-5, HANDII, TBX5 or a combination thereof null pig cell of a) into an enucleated pig oocyte and activating said oocyte to divide so as to form a NKX2-5, HANDII, TBX5 or a combination thereof null pig morula or blastocyst; c) introducing pig stem cells into the pig NKX2-5, HANDII, TBX5 or a combination thereof null morula or blastocyst of b); and d) implanting said morula or blastocyst from c) into a pseudopregnant surrogate pig to generate a chimeric pig expressing exogenous pig NKX2-5, HANDII, TBX5 or a combination thereof.

Another embodiment provides a method of producing human or humanized cardiac cells in a non-human animal comprising: a) generating a NKX2-5, HANDII, TBX5 or a combination thereof null non-human cell, wherein both alleles of the non-human NKX2-5 gene, HANDII gene, TBX5 gene or a combination thereof carry a mutation that prevents production of functional the non-human NKX2-5 protein. HANDII protein, TBX5 protein or combination thereof; b) creating a NKX2-5, HANDII, TBX5 or a combination thereof null non-human morula or blastocyst by somatic cell nuclear transfer comprising fusing a nucleus from said MYF5, MYOD, MRF4 or a combination thereof null non-human cell of a) into an enucleated non-human animal oocyte and activating said oocyte to divide so as to form a NKX2-5, HANDII, TBX5 or a combination thereof null non-human animal morula or blastocyst; c) introducing human stem cells into the NKX2-5, HANDII, TBX5 or a combination thereof null non-human animal blastocyst or morula of b); and d) implanting said blastocyst or morula from c) into a pseudopregnant surrogate non-human animal so as to generate a non-human animal expressing human or humanized cardiac cells.

In one embodiment the non-human animal is a porcine, bovine, equine or goat. In another embodiment the human stem cell is a tissue specific stem cell, pluripotent stem cell, multipotent adult stem cell, induced pluripotent stem cell or umbilical cord blood stem cell (UCBSC). In another embodiment the induced pluripotent cell is formed from a fibroblast cell.

One embodiment provides a pig cell, morula or blastocyst wherein the genome carries a mutation in both alleles of the NKX2-5 gene, HANDII gene, TBX5 gene or a combination thereof such that the pig cell or blastocyst lacks functional NKX2-5 protein, HANDII protein, TBX5 protein or a combination thereof. In one embodiment, the mutation is a deletion of the NKX2-5 gene, HANDII gene, TBX5 gene or a combination thereof.

One embodiment provides a chimeric pig expressing human NKX2-5, HANDII. TBX5 or a combination thereof and lacking expression of pig NKX2-5, HANDII, TBX5 or a combination thereof. In one embodiment, the chimeric pig produces humanized cardiac cells and/or tissue.

One embodiment provides a method for producing a chimeric pig expressing a human NKX2-5 gene, HANDII gene, TBX5 gene or a combination thereof comprising: a) generating a NKX2-5, HANDII. TBX5 or a combination thereof null pig cell, wherein both copies of the pig NKX2-5 gene, HANDII gene, TBX5 gene or a combination thereof gene carry a mutation that prevents production of functional pig NKX2-5 protein, HANDII protein, TBX5 protein or combination thereof; b) creating a NKX2-5, HANDII, TBX5 or a combination thereof null pig morula or blastocyst by somatic cell nuclear transfer comprising fusing a nucleus from said NKX2-5, HANDI, TBX5 or a combination thereof null pig cell of a) into an enucleated pig oocyte and activating said oocyte to divide so as to form a NKX2-5, HANDII, TBX5 or a combination thereof null pig morula or blastocyst; c) introducing human stem cells into the pig NKX2-5, HANDII, TBX5 or a combination thereof null morula or blastocyst of b); and d) implanting said morula or blastocyst from c) into a pseudopregnant surrogate pig to generate a chimeric pig expressing human NKX2-5, HANDII, TBX5 or a combination thereof.

Another embodiment provides a method of producing humanized cardiac cells in pigs comprising: a) generating a NKX2-5, HANDII, TBX5 or a combination thereof null pig cell, wherein both alleles of the pig NKX2-5 gene, HANDII gene, TBX5 gene or a combination thereof carry a mutation that prevents production of functional pig NKX2-5 protein, HANDII protein, TBX5 protein or combination thereof; b) creating a NKX2-5, HANDII, TBX5 or a combination thereof null pig morula or blastocyst by somatic cell nuclear transfer comprising fusing a nucleus from said MYF5, MYOD, MRF4 or a combination thereof null pig cell of a) into an enucleated pig oocyte and activating said oocyte to divide so as to form a NKX2-5, HANDII, TBX5 or a combination thereof null pig morula or blastocyst; c) introducing human stem cells into the pig NKX2-5, HANDII, TBX5 or a combination thereof null blastocyst of b); and d) implanting said blastocyst from c) into a pseudopregnant surrogate pig so as to generate a pig expressing humanized cardiac cells. In one embodiment, the human stem cell is a human induced pluripotent stem cell, a human pluripotent stem cells or a human umbilical cord blood stem cell. In another embodiment, the human induced pluripotent cell is formed from a fibroblast cell.

It would be useful to make human or humanized tissues and organs personalized to each recipient's immune complex. As disclosed herein, it is possible to do so by using a large animal as a host and editing its genome to knock out or debilitate genes responsible for the growth and/or differentiation of a target organ and inoculating that animal at a blastocyst or zygote stage with donor stem cells to complement the missing genetic information for the growth and development of the organ. The result is a chimeric animal in which the complemented tissue (human/humanized organ) matches the genotype and phenotype of the donor. Such organs may be made in a single generation and the stem cell may be taken or generated from the patient's own body. As disclosed herein, it is possible to do so by simultaneously editing multiple genes in a cell (see, for example, WO 2015/168125, which is incorporated herein by reference). Multiple genes can be targeted for editing using targeted nucleases and homology directed repair (HDR) templates in vertebrate cells or embryos.

BRIEF DESCRIPTION OF THE DRAWINGS

FIGS. 5A-F demonstrate that Nkx2-5 governs networks in CPCs and is a factor for cardiogenesis. (A) A cardiac enhancer region of the Nkx2-5 gene was fused to the fluorescent reporter (EYFP) and used to generate transgenic mice. (B) The Nkx2-5 enhancer directs EYFP expression to the cardiac progenitor cell population in transgenic mouse embryos. (C) RNA was isolated from the sorted CPCs, amplified and gene expression was evaluated using Affymetrix array analysis. Results of Affymetrix array analysis of Nkx2-5-EYFP CPCs vs. the respective negative cell populations from single embryos (E7.75-E9.5) reveal increased gene expression associated with cardiac development and identifies HandII and Tbx5 as factors in the cardiac crescent. Identification of genes upregulated in Nkx2-5 null cardiac progenitor cells (CPCs). (D) EYFP is directed to the CPCs in the 6kbNkx2-5-EYFP: WT and 6kbNkx2-5-EYFP: Nkx2-5 null littermates at E8.0 and E9.5. (E) Venn diagram of array analysis for genes that were significantly upregulated in EYFP positive Nkx2-5 null (−/−) vs. WT (+/+) CPCs isolated at E8.0 and E9.5 stages. (F) Schematic which summarizes the results of the studies demonstrating the role of Nkx2-5 in the repression of blood formation, the promotion of the endothelial lineage (via Etv2) and the promotion of the cardiac lineage (by regulating Bnp, Anf, Mlc-2v and Cripto).

FIGS. 8A-H demonstrate that loss of porcine ETV2 recapitulated the mouse Etv2 mutant phenotype. Wild-type E18.0 pig embryo (A) and ETV2 knockout embryo (B) at the 24 somites stage. Insets show enlarged views of the allantois. Note an abnormal overall morphology with lack of vascular plexus formation in the mutant (inset). (C-H) Sections through the allantois (C, D), the heart level (E, F) and the trunk level (G, H) of the embryos shown in A and B. respectively, were stained for Tie2, an endothelial marker; Gata4, a cardiac lineage marker; and DAPI, a nuclear counterstain. The wild-type allantois was highly vascularized with Tie2 positive endothelial lining (C, arrows), whereas, the mutant lacked this cell population (D). The endocardium, cardinal veins (CV), and dorsal aortae (DA) are clearly visible in the wild-type embryo (E, G). In contrast, ETV2 null embryos completely lacked these structures although the heart progenitors and gut marked by Gata4 were present (F and H, respectively). Scale bars: 1000 μm (A, B), 200 μm (insets in A, B), 100 μm (C-H).

DETAILED DESCRIPTION OF THE INVENTION

Figure 1:
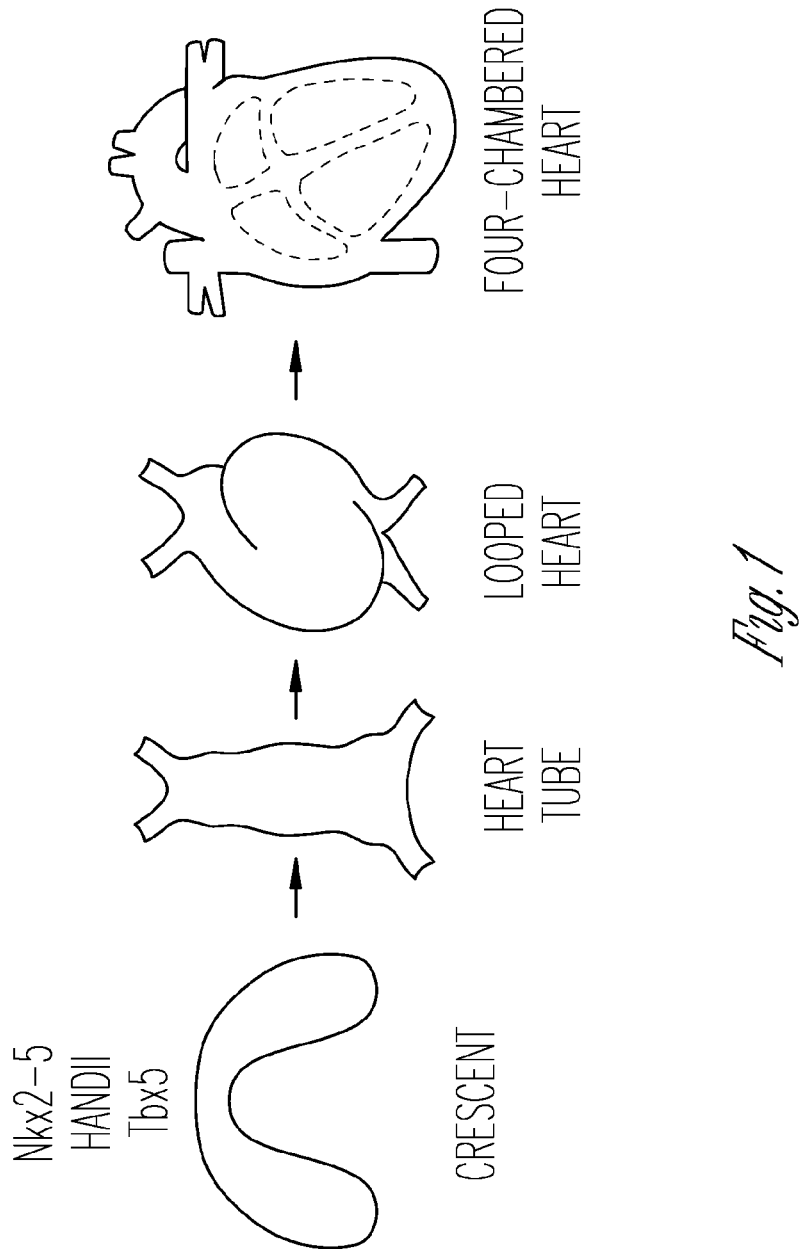
FIG. 1 depicts a schematic of cardiac morphogenesis in the mouse. (Left to right) Formation of the cardiac crescent (E7.5), linear heart tube (E8.5), looped heart (E9.5) and four-chambered heart (E10.5).

Cardiovascular disease is the number one cause of death in this country and across the world. Currently one in three adults are living with cardiovascular disease. Congenital heart defects are common and can progress to end stage heart failure. While heart transplantation is the only cure for end stage heart failure, relatively few patients receive this therapy due to limited availability of donor organs. In short, there is an inadequate supply of hearts to treat patients who need this curative therapy. Moreover, there are no relevant human models to test new devices, pharmacological or surgical therapies for congenital or heart failure diseases. Thirdly, there are no relevant human models to identify or examine factors that promote cardiac regeneration, which could eliminate the need for cardiac transplantation. Lastly, a source of personalized human tissues that can be generated using the patient's own stem cells is provided herein (thereby obviating ethical issues such as organ donation or use of human embryonic stem cells). Thus provided herein is the utilization of emerging technologies to revolutionize the field by engineering a humanized heart in a large animal model.

Presented herein are compositions and methods to generate a human organ (a heart)/humanized tissues in pigs, which will serve as an unlimited source of hearts/tissues for transplantation and provide a large animal model to study the regeneration of the human heart and/or the response of a human heart to experimental medications.

In particular, provided herein are compositions and methods to provide personalized heart tissue or a heart for millions of people that would benefit from such therapy. This strategy will revolutionize cardiovascular medicine and provide a cure for this devastating disease. Personalized heart valves, heart tissue, coronary arteries and entire hearts can be available for patients, which would obviate the use of immunosuppression agents. Moreover, provided herein is a platform for the generation of other tissues such as personalized blood, vasculature, muscle, bones and lungs.

Previously, transgenic and gene disruption mouse models were engineered to define networks that are necessary and sufficient for cardiogenesis. Roles for Nkx2-5 as a transcriptional activator of cardiac development, as a repressor of blood formation and as an activator of Etv2, a master endothelial/endocardial factor (5-21), have been demonstrated. Based on the data and other publications, it was believed that a mutant animal for Nkx2-5/Hand2/Tbx5 would completely lack a heart (22-26). Using state-of-the-art gene editing technologies, mutant porcine embryos were generated, which are lethal during early development and have perturbed or absent cardiovascular lineages. In addition to serving as a novel source of human tissues for the treatment of cardiovascular disease, the humanized pigs can also serve as a large animal model to study the regeneration of human lineages or response(s) to pharmacological agents and lead to improved therapies for cardiovascular diseases including congenital and heart failure diseases. The approach combines innovative and emerging technologies to decipher the networks and stem cell populations that govern cardiovascular lineages and produce human-specific tissues in a porcine host.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as Hawley's Condensed Chemical Dictionary 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

As used herein, the articles "a" and "an" refer to one or to more than one, i.e., to at least one, of the grammatical object of the article. By way of example, "an element" means one element or more than one element.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

As used herein, "or" should be understood to have the same meaning as "and/or" as defined above. For example, when separating a listing of items, "and/or" or "or" shall be interpreted as being inclusive, e.g., the inclusion of at least one, but also including more than one, of a number of items, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

As used herein, the terms "including", "includes", "having", "has", "with", or variants thereof, are intended to be inclusive similar to the term "comprising."

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to," "at least," "greater than," "less than," "more than," "or more," and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group.

Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "isolated" refers to a factor(s), cell or cells which are not associated with one or more factors, cells or one or more cellular components that are associated with the factor(s), cell or cells in vivo.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

The terms "cell," "cell line," and "cell culture" as used herein may be used interchangeably. All of these terms also include their progeny, which are any and all subsequent generations. It is understood that all progeny may not be identical due to deliberate or inadvertent mutations.

"Cells" include cells from, or the "subject" is, a vertebrate, such as a mammal, including a human. Mammals include, but are not limited to, humans, farm animals, sport animals and companion animals. Included in the term "animal" is dog, cat, fish, gerbil, guinea pig, hamster, horse, rabbit, swine, mouse, monkey (e.g., ape, gorilla, chimpanzee, or orangutan), rat, sheep, goat, cow and bird.

In one embodiment, the stem, progenitor or precursor cells are embryonic stem cells, adult stem cells, induced pluripotent stem cells, and/or multipotent stem cells (such as multipotent mesodermal precursors). In one embodiment, the stem, progenitor or precursor cells are mammalian cells. In one embodiment, the stem cells include, but are not limited to, induced pluripotent stem cells, umbilical blood cord stem cells, mesenchymal stem cells, pluripotent stem cells. In one embodiment, the stem cells are of human origin. In another embodiment, the stem cells are of pig origin.

Totipotent (a.k.a. omnipotent) stem cells can differentiate into embryonic and extraembryonic cell types. Such cells can construct a complete, viable organism. These cells are produced from the fusion of an egg and sperm cell. Cells produced by the first few divisions of the fertilized egg are also totipotent. Pluripotent stem cells are the descendants of totipotent cells and can differentiate into nearly all cells, i.e. cells derived from any of the three germ layers. Multipotent stem cells can differentiate into a number of cell types, but only those of a closely related family of cells. Oligopotent stem cells can differentiate into only a few cell types, such as lymphoid or myeloid stem cells. Unipotent cells can produce only one cell type, their own,[4] but have the property of self-renewal, which distinguishes them from non-stem cells (e.g. progenitor cells, muscle stem cells).

"Expansion" refers to the propagation of cells without differentiation.

"Progenitor cells" are cells produced during differentiation of a stem cell that have some, but not all, of the characteristics of their terminally-differentiated progeny. Defined progenitor cells are committed to a lineage, but not to a specific or terminally-differentiated cell type. The phrase "endothelial cells" encompasses not only terminally-differentiated cells types, but also cells that are committed to an endothelial lineage, but are not terminally-differentiated.

"Differentiation factors" refer to cellular factors, preferably growth factors or angiogenic factors that induce lineage commitment.

The terms "pig," "swine" and "porcine" are used interchangeably and are generic terms referring to the same type of animal without regards to gender, size or breed. It is also noted that terms "pig," "swine" and "porcine", such as the null "pig," "swine" and "porcine" that is complemented with human or pig genes, the "pig," "swine" and "porcine" may be embryos, neonates or adults (including newborns and young pigs).

The terms "Hand2" and "HandII" are used interchangeably.

As used herein, the phrases "humanized skeletal muscle," "humanized cardiac muscle," or "humanized muscle" refer to cells or tissue in a pig or other non-human animal that express one more human genes and/or proteins. In one embodiment, the pig cells or tissue that express one more human genes/proteins do not express the corresponding functional pig gene and/or protein.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "control" cell is a cell having the same cell type as a test cell. The control cell may, for example, be examined at precisely or nearly the same time the test cell is examined. The control cell may also, for example, be examined at a time distant from the time at which the test cell is examined, and the results of the examination of the control cell may be recorded so that the recorded results may be compared with results obtained by examination of a test cell.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, a "functional" biological molecule is a biological molecule in a form in which it exhibits a property by which it is characterized. A functional enzyme, for example, is one which exhibits the characteristic catalytic activity by which the enzyme is characterized.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5 and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site having the universal resource locator using the BLAST tool at the NCBI website. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively. PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

As used herein, an "instructional material" includes a publication, a recording, a diagram, or any other medium of expression which can be used to communicate the usefulness of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified invention, or portion thereof, or be shipped together with a container which contains the invention or portion thereof. Alternatively, the instructional material may be shipped separately from the container with the intention that the instructional material and the compound be used cooperatively by the recipient.

As used herein, the term "nucleic acid" encompasses RNA as well as single and double stranded DNA and cDNA. Furthermore, the terms, "nucleic acid," "DNA," "RNA" and similar terms also include nucleic acid analogs, i.e. analogs having other than a phosphodiester backbone. For example, the so called "peptide nucleic acids," which are known in the art and have peptide bonds instead of phosphodiester bonds in the backbone, are considered within the scope of the present invention. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine, and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

The term "nucleic acid construct," as used herein, encompasses DNA and RNA sequences encoding the particular gene or gene fragment desired, whether obtained by genomic or synthetic methods.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "oligonucleotide" typically refers to short polynucleotides, generally, no greater than about 50 nucleotides. It will be understood that when a nucleotide sequence is represented by a DNA sequence (i.e., A. T. G, C), this also includes an RNA sequence (i.e., A, U, G, C) in which "U" replaces "T."

Transcription Activator-Like Effector Nucleases (TALENs) are artificial restriction enzymes generated by fusing the TAL effector DNA binding domain to a DNA cleavage domain. These reagents enable efficient, programmable, and specific DNA cleavage for genome editing in situ. Transcription activator-like effectors (TALEs) are proteins that bind DNA in a sequence specific way. By fusing such a TALE to a nuclease (e.g., FokI endonuclease) a highly specific DNA "scissor" is made (these molecules can be engineered to bind any DNA sequence). The term TALEN, as used herein, is broad and includes a monomeric TALEN that can cleave double stranded DNA without assistance from another TALEN. The term TALEN is also used to refer to one or both members of a pair of TALENs that are engineered to work together to cleave DNA at the same site. TALENs that work together may be referred to as a left-TALEN and a right-TALEN, which references the handedness of DNA.

Once the TALEN genes have been assembled they are inserted into plasmids; the plasmids are then used to transfect the target cell where the gene products are expressed and enter the nucleus to access the genome. TALENs can be used to edit genomes by inducing double-strand breaks (DSB) and optionally inserting a cargo/preselected gene, which cells respond to with repair mechanisms. In this manner, they can be used to correct mutations in the genome which, for example, cause disease.

Genetic engineering, including gene editing, can be carried out by any method available to an art worker, for example, by the use of targeted endonucleases, and homology directed repair (HDR), TALEN, CRISPR (e.g., CAS9/CRISPR), recombinase fusion molecules, synthetic porcine artificial chromosomes, meganucleases, zinc finger or rAAV based systems for gene editing (e.g., to knockout desired target genes). Further, a variety of nucleic acids can be introduced into cells, for knockout purposes, for inactivation of a gene (such as interfering RNAs (shRNA, siRNA, dsRNA, RISC, miRNA) or express a gene.

Somatic cell nuclear transfer (SCNT) is a laboratory technique for creating a viable embryo from a body cell and an egg cell. The process of somatic cell nuclear transplant involves two different cells. The first being a female gamete, known as the ovum (egg/oocyte). The second being a somatic cell, referring to the cells of the human body. Skin cells, fat cells, and liver cells are only a few examples. The nucleus of the donor egg cell is removed and discarded, leaving it 'deprogrammed.' The nucleus of the somatic cell is also removed but is kept, the enucleated somatic cell is discarded. What is left is a lone somatic nucleus and an enucleated egg cell. These are then fused by squirting the somatic nucleus into the 'empty' ovum. After being inserted into the egg, the somatic cell nucleus is reprogrammed by its host egg cell. The ovum, now containing the somatic cell's nucleus, is stimulated with a shock and will begin to divide. The egg is now viable and capable of producing an adult organism containing all the necessary genetic information from just one parent. Development will ensue normally and after many mitotic divisions, this single cell forms a blastocyst (an early stage embryo with about 100 cells) with an identical genome to the original organism (i.e. a clone). Stem cells can then be obtained by the destruction of this clone embryo for use in therapeutic cloning or in the case of reproductive cloning the clone embryo is implanted into a host mother (pseudopragnant/surrogate) for further development and brought to term.

"Chimera" refers to is a single organism composed of genetically distinct cells.

A nullizygous organism carries two mutant or missing alleles for the same gene. The mutant/missing alleles are both complete loss-of-function or 'null' alleles, so homozygous null and nullizygous are synonymous.

A gene knockout (abbreviation: KO) is a genetic technique in which both of an organism's alleles are made inoperative ("knocked out" of the organism). Also known as knockout organisms or simply knockouts. The term also refers to the process of creating such an organism, as in "knocking out" a gene. The technique is essentially the opposite of a gene knockin.

The term gene is broad and refers to chromosomal DNA that is expressed to make a functional product. Genes have alleles. Gene editing may be mon-allelic or bi-allelic.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene which is expressed in a recombinant host cell wherein the gene comprises a recombinant polynucleotide, produces a "recombinant polypeptide."

A "recombinant cell" is a cell that comprises a transgene. Such a cell may be a eukaryotic or a prokaryotic cell. Also, the transgenic cell encompasses, but is not limited to, an embryonic stem cell comprising the transgene, a cell obtained from a chimeric mammal derived from a transgenic embryonic stem cell where the cell comprises the transgene, a cell obtained from a transgenic mammal, or fetal or placental tissue thereof, and a prokaryotic cell comprising the transgene.

The term "regulate" refers to either stimulating or inhibiting a function or activity of interest.

As used herein, a 'subject in need thereof' is a patient, animal, mammal, or human, who will benefit from the invention.

As used herein, a "substantially homologous amino acid sequences" includes those amino acid sequences which have at least about 95% homology, preferably at least about 96% homology, more preferably at least about 97% homology, even more preferably at least about 98% homology, and most preferably at least about 99% or more homology to an amino acid sequence of a reference antibody chain. Amino acid sequence similarity or identity can be computed by using the BLASTP and TBLASTN programs which employ the BLAST (basic local alignment search tool) 2.0.14 algorithm. The default settings used for these programs are suitable for identifying substantially similar amino acid sequences for purposes of the present invention.

"Substantially homologous nucleic acid sequence" means a nucleic acid sequence corresponding to a reference nucleic acid sequence wherein the corresponding sequence encodes a peptide having substantially the same structure and function as the peptide encoded by the reference nucleic acid sequence; e.g., where only changes in amino acids not significantly affecting the peptide function occur. Preferably, the substantially identical nucleic acid sequence encodes the peptide encoded by the reference nucleic acid sequence. The percentage of identity between the substantially similar nucleic acid sequence and the reference nucleic acid sequence is at least about 50%, 65%, 75%, 85%, 95%, 99% or more. Substantial identity of nucleic acid sequences can be determined by comparing the sequence identity of two sequences, for example by physical/chemical methods (i.e., hybridization) or by sequence alignment via computer algorithm. Suitable nucleic acid hybridization conditions to determine if a nucleotide sequence is substantially similar to a reference nucleotide sequence are: 7% sodium dodecyl sulfate SDS, 0.5 M NaPO4, 1 mM EDTA at 50° C. with washing in 2× standard saline citrate (SSC), 0.1% SDS at 50° C.; preferably in 7% (SDS), 0.5 M NaPO4, 1 mM EDTA at 50° C. with washing in IX SSC, 0.1% SDS at 50° C.; preferably 7% SDS, 0.5 M NaPO4, 1 mM EDTA at 50° C. with washing in 0.5×SSC, 0.1% SDS at 50° C.; and more preferably in 7% SDS, 0.5 M NaPO4, 1 mM EDTA at 50° C. with washing in 0.1×SSC, 0.1% SDS at 65° C. Suitable computer algorithms to determine substantial similarity between two nucleic acid sequences include, GCS program package (Devereux et al., 1984 Nucl. Acids Res. 12:387), and the BLASTN or FASTA programs (Altschul et al., 1990 Proc. Natl. Acad. Sci. USA. 1990 87:14:5509-13; Altschul et al., J. Mol. Biol. 1990 215:3:403-10; Altschul et al., 1997 Nucleic Acids Res. 25:3389-3402). The default settings provided with these programs are suitable for determining substantial similarity of nucleic acid sequences for purposes of the present invention.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer or delivery of nucleic acid to cells, such as, for example, polylysine compounds, liposomes, and the like. Examples of viral vectors include, but are not limited to, adenoviral vectors, adeno-associated virus vectors, retroviral vectors, recombinant viral vectors, and the like. Examples of non-viral vectors include, but are not limited to, liposomes, polyamine derivatives of DNA and the like.

Methods involving conventional molecular biology techniques are described herein. Such techniques are generally known in the art and are described in detail in methodology treatises, such as Molecular Cloning: A Laboratory Manual, 2nd ed., vol. 1-3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, New York, 1992 (with periodic updates). Methods for chemical synthesis of nucleic acids are discussed, for example, in Beaucage and Carruthers, Tetra. Letts. 22: 1859-1862, 1981, and Matteucci et al., J. Am. Chem. Soc. 103:3185, 1981.

The terms "comprises," "comprising." and the like can have the meaning ascribed to them in U.S. Patent Law and can mean "includes," "including" and the like. As used herein, "including" or "includes" or the like means including, without limitation.

Exogenic Organ/Tissue Production

The humanized large animal model is a resource for regenerative medicine and will serve as a platform for personalized humanized porcine models. This strategy will transform the current clinical practice paradigms for chronic musculoskeletal diseases and transplantation. Ablation of porcine cardiac muscle is unique, because it not only aims to develop humanized cardiac muscle in a large animal model, but because it is a novel approach to circumvent immune rejection, and can be broadly applicable for exogenic organ development strategies.

Figure 6:
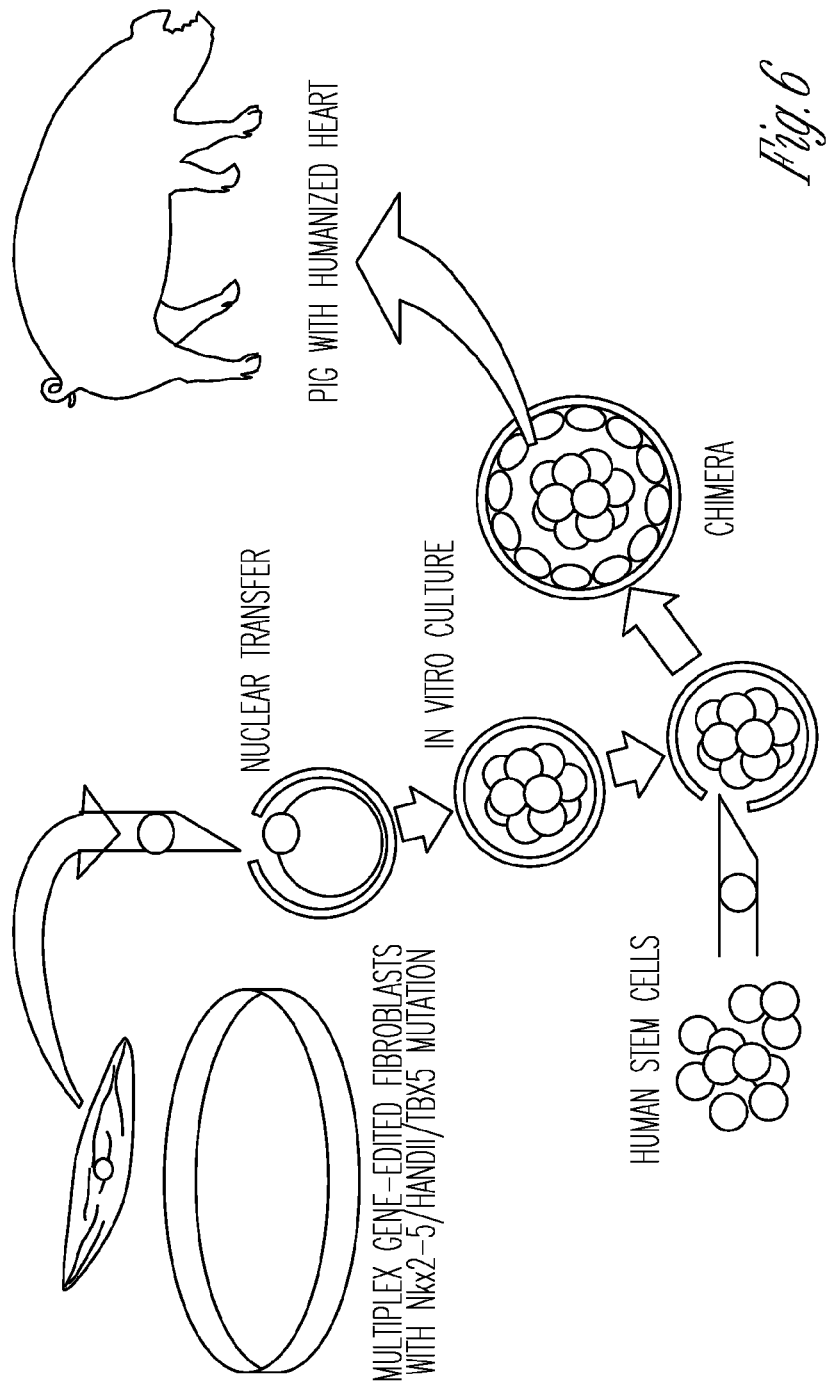
FIG. 6 depicts the overall strategy to produce a humanized heart in a pig model. Multiplex gene editing will be utilized to produce NKX2-5/HANDII/TBX5 mutant pig fibroblasts, as well as SCNT and human stem cell delivery to engineer a pig with a humanized heart.

Currently, the only definitive therapy for advanced end-stage organ failure is transplantation. Millions of patients could benefit from such therapy, but are not eligible for transplantation due to limited donor organ availability. Therefore, there is a significant shortage of cadaveric or living-related donor organs. Furthermore, transplantation of organs requires lifelong immunosuppression, which also has deleterious, life-limiting side effects. Described herein are humanized tissues generated in pigs that will serve as an unlimited source of organs for transplantation and provide a paradigm-shifting platform for the treatment of cardiovascular diseases (FIG. 6).

Intense interest has focused on exogenic transplantation and recent technological advances support the notion that these strategies can be successful. For example, a rat pancreas was produced in a mouse by the process of blastocyst complementation (38). In these studies, blastocysts mutant for Pdx1, the master regulatory gene for pancreatic development, were injected with pluripotent stem cells from wild-type rats (rPSCs) (38). Transfer of the rPSC-injected blastocysts into surrogate mouse dams gave rise to mouse chimeras with functional pancreata composed of rat cells. These mutant hosts provide a developmental "niche," for healthy donor stem cells to populate and generate a donor-derived organ. The blastocyst complementation strategy has also produced organs such as the kidney and liver in rodents, and recently the pancreas in pigs (39-41). This latter report using the porcine model supports the development of human patient-specific organs in pigs that can be subsequently used for transplantation or advanced therapies (FIG. 6).

The humanized large animal model is a resource for regenerative medicine and will serve as a platform for personalized humanized porcine models. This strategy will transform the current clinical practice paradigms for chronic musculoskeletal diseases and transplantation. Ablation of porcine heart tissue is unique, because it not only aims to develop humanized heart tissue in a large animal model, but because it is a novel approach to circumvent immune rejection, and can be broadly applicable for exogenic organ development strategies.

Using a gene-editing platform, various developmental genes can be mutated to generate organ and/or tissue deficient pigs, upon which blastocyst complementation can be deployed for the generation of exogenic organs and/or tissue. The efficiency of this system allows many genes to be tested empirically. The simultaneous modification of multiple regulatory genes permits the modulation of complex tissue ontogeny.

Muscle Diseases/Disorders

Cardiac tissue and cells include cardiac muscle cells or cardiomyocytes (also known as myocardiocytes or cardiac myocytes) are the muscle cells (myocytes) that make up the cardiac muscle. Cardiovascular disease or cardiac disease includes diseases of heart and blood vessels, many of which are related to atherosclerosis. Diseases/disorders include, but are not limited to, heart attack, stroke, heart failure, arrhythmia, and heart valve problems.

Generation of Precision Knockout (KO) Pigs to Generated Human-Pig Chimeras for Organ Production With the use of site-specific nucleases, efficiencies of introducing precise genetic alterations in large animal genomes have improved more than 100,000-fold. Highly efficient heterozygous and bi-allelic knockouts (KOs) in livestock at rates of 50% and 20%, respectively, was demonstrated using a TALEN based platform to inactivate genes by non-homologous end-joining (NHEJ) of double-stranded breaks cleaved by site-specific nucleases (27). Using the gene-editing platform, various developmental genes can be mutated to generate organ-deficient pigs, upon which blastocyst complementation can be deployed for the generation of exogenic organs. The efficiency of this system allows many genes to be tested empirically.

ETV2 Knockout Pig Embryos Lack the Endothelial Lineage

Figure 7A:
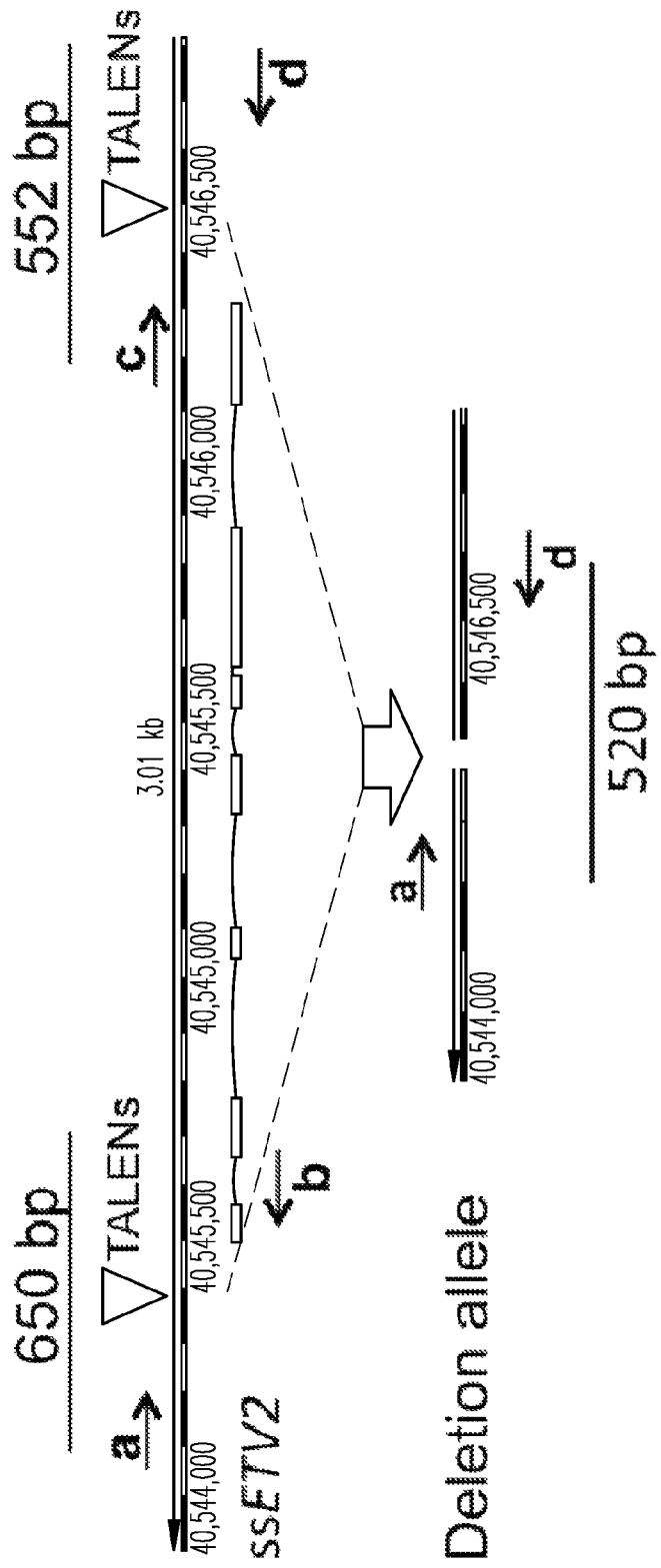
FIGS. 7A-B depict TALEN-mediated knockout of ETV2. (A) Three-tiered PCR assay utilized to detect gene editing. Amplification from primers a-d indicated a deletion allele was present. To distinguish between heterozygous and homozygous clones, primers a-b and c-d were used to amplify the wild type allele. Only when the a-d product is present and both a-b, c-d products are absent is the clone considered homozygous for the deletion allele. (B) Clones fitting these criteria are enclosed by green boxes.
Figure 7B:
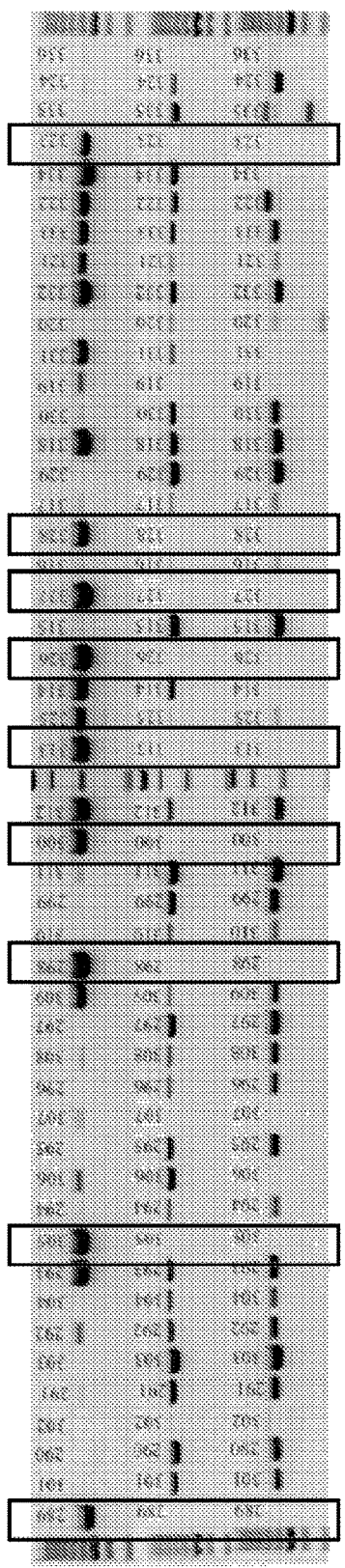
Figure 8C:
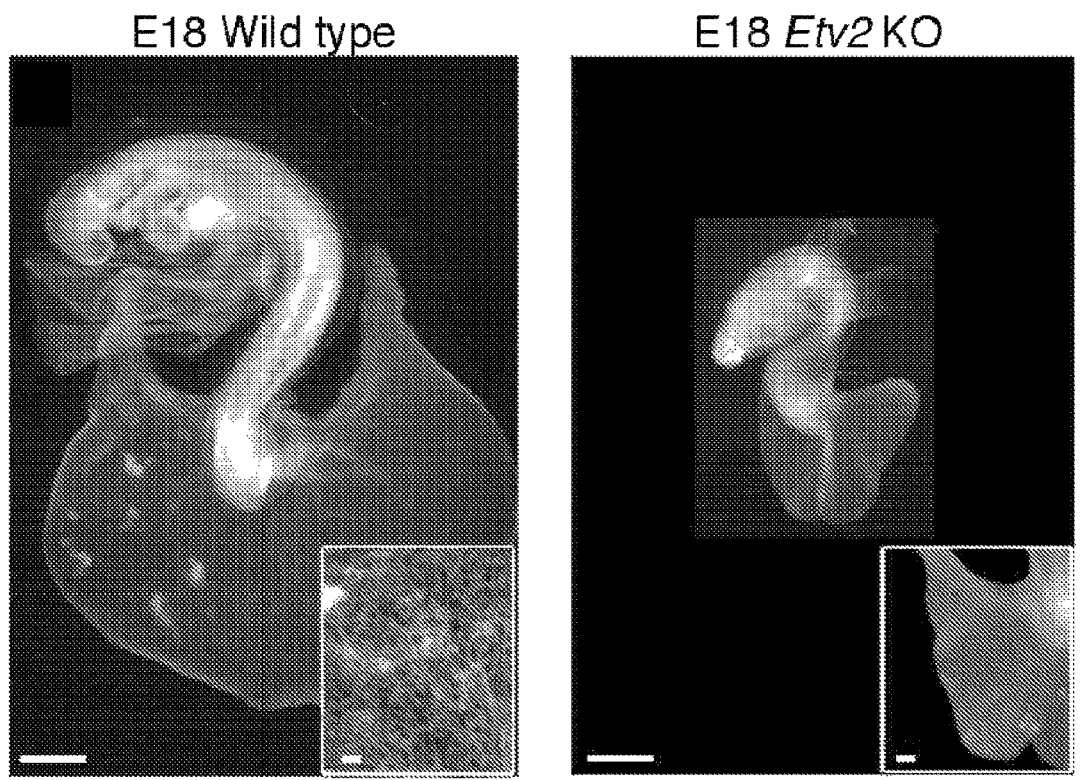
Figure 8C:
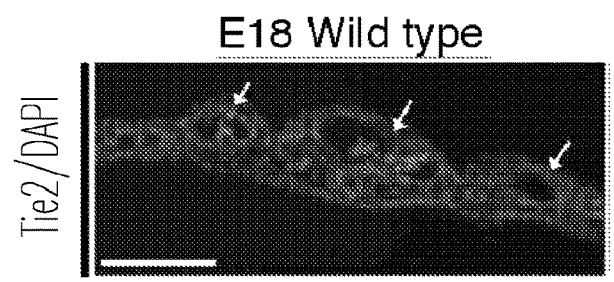
Figure 8D:
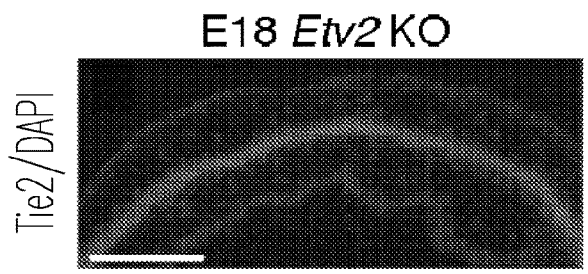
Figure 8E:
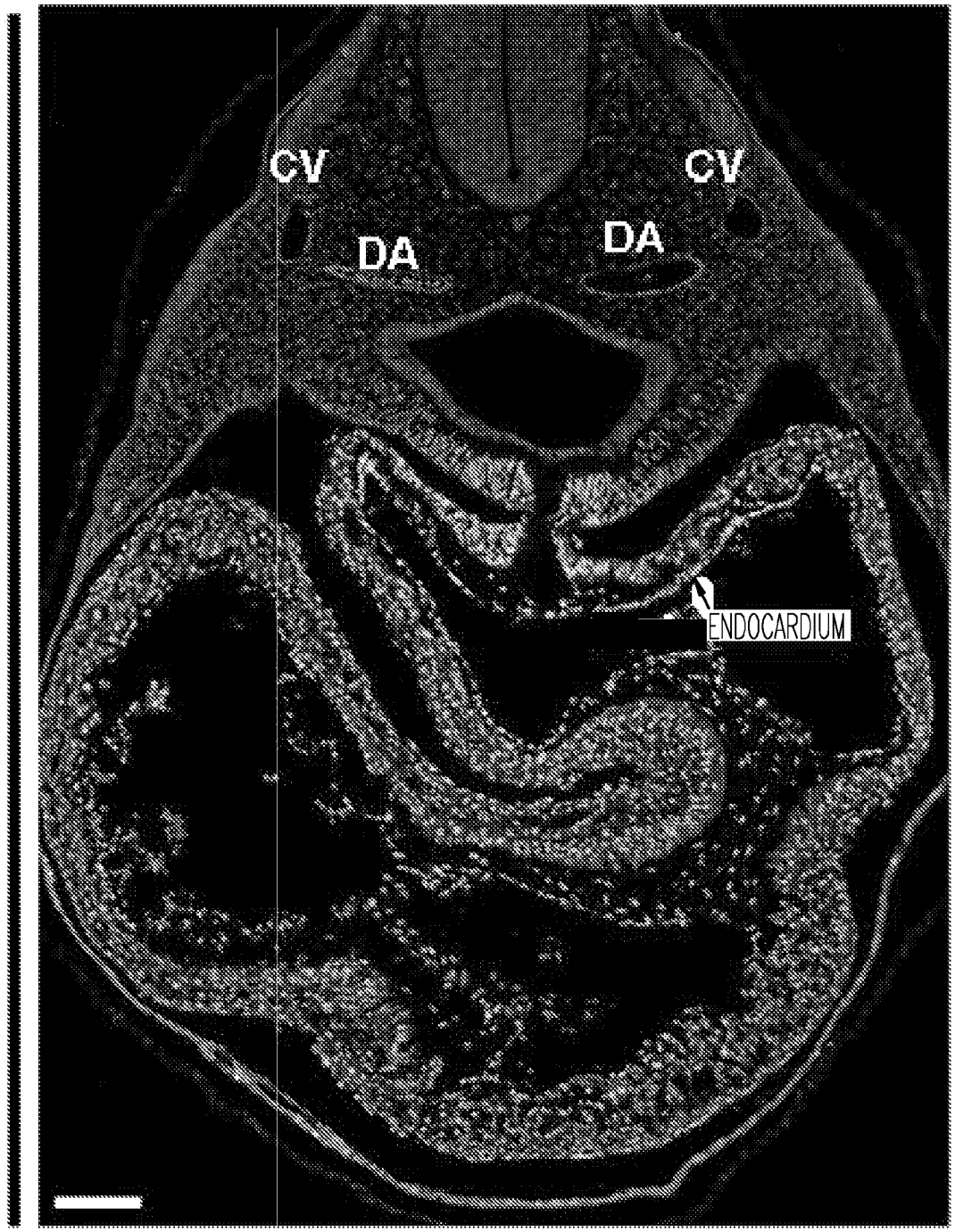
Figure 8F:
Figure 8G:
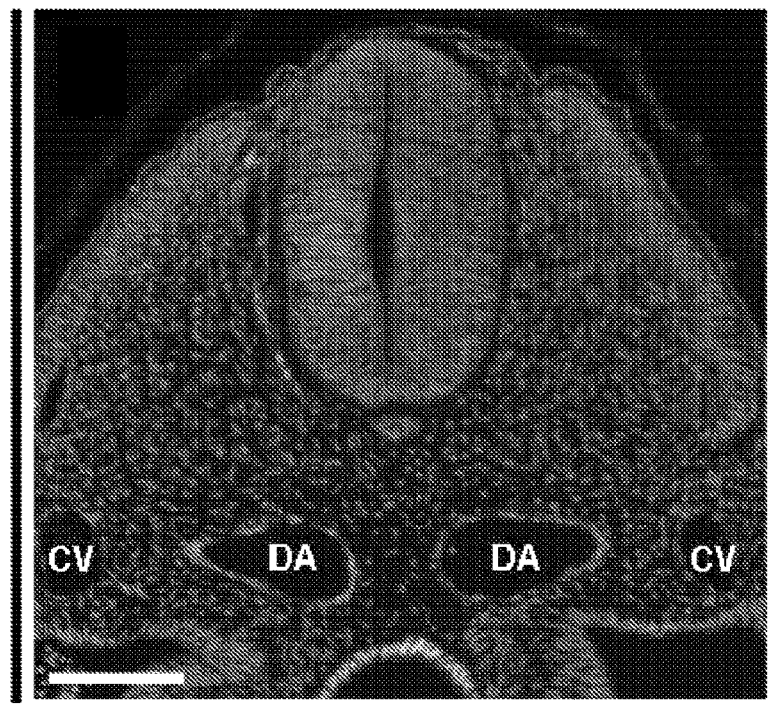
Figure 8H:
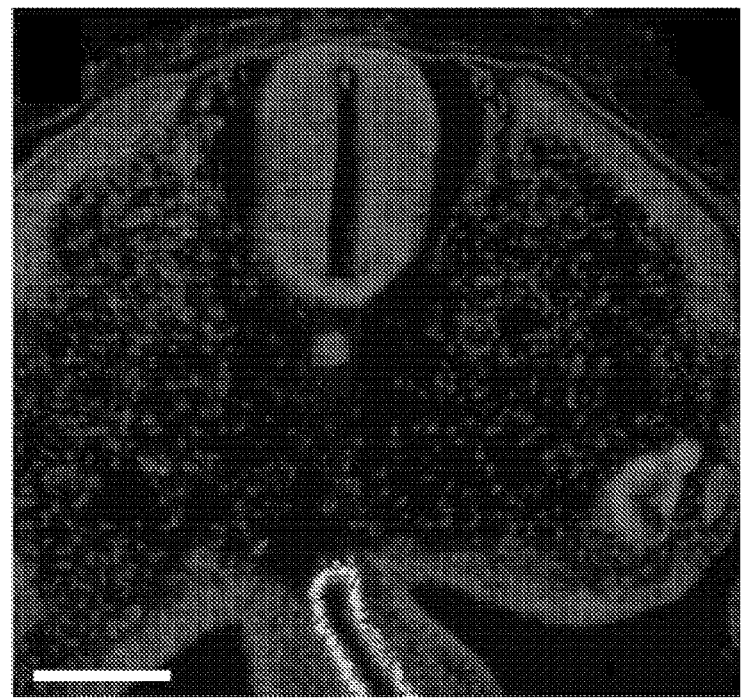

Previous studies have demonstrated that Nkx2-5 is an upstream regulator of the Etv2 gene and that Etv2 is a master regulator of the endothelial lineage in the mouse, as embryos lacking Etv2 are lethal at approximately E9.5 with an absence of vasculature (8, 10, 12, 13). To examine the role of ETV2 in the pig, the entire ETV2 coding sequence was removed using two TALEN pairs flanking the gene in porcine fibroblasts (FIG. 7A). The process was 15% efficient at homozygous gene removal; 79/528 of the genotyped clones were homozygous for the deletion of the ETV2 gene (FIG. 7B). ETV2 homozygous knockout fibroblast clones were used for nuclear cloning (Somatic Cell Nuclear Transfer; SCNT) to generate ETV2 null embryos, which were transferred to surrogate sows. The cloning efficiency was 29%, which was higher than the average success rate of 20%. Embryos were harvested and analyzed at E18.0 (FIG. 8). At this stage, Wt embryos were vascularized with a well-developed vascular plexus in the allantois (FIG. 8A, C). In contrast, growth was significantly retarded in ETV2 KOs, (FIG. 7B), and these embryos lacked the endocardial/endothelial lineages (FIG. 8D, F, H). ETV2 KO embryos lacked cardinal veins, dorsal aortae, and the endocardium, that are clearly developed in the Wt embryos (FIG. 8E-H). The results reflect similarities in mouse and pig phenotypes and suggest that the function of ETV2 is conserved between these species. Further, these data demonstrate that one can direct multiple mutations into the porcine genome to support growth of chimeric organs that will be humanized in more than one cell type.

Nkx2-5, HandII and Tbx5

Nkx2-5, HandII and Tbx5 were mutated to generate heart muscle lineage deficient pig embryos (Nkx2-5/HandII/Tbx5 null porcine embryos). Performing multiplex gene edits for Nkx2-5/HandII/Tbx5 created a permissive niche that is repopulated with cardiac cells using human cells with pluripotent capacity, to yield humanized heart/cardiac tissue and/or cardiac muscle. See details in Example 2.

The humanized large animal model will be an important resource for regenerative medicine and will serve as a platform for making personalized organs. This strategy can transform the current clinical practice paradigms for muscle diseases and transplantation. To date, exogenic transplantation of organs has been performed between mouse and rat (27, 29); and pig and pig (31), and no successful development of humanized organs in large animal models have been reported. Incorporated herein by reference is U.S. Provisional Application Ser. Nos. 62/247,092; 62/247,096; and 62/247,122.

The following example is intended to further illustrate certain particularly preferred embodiments of the invention and is not intended to limit the scope of the invention in any way.

EXAMPLES

Example 1: Nkx2-5, HandII and Tbx5 as Regulators of Cardiogenesis

Figure 5E:
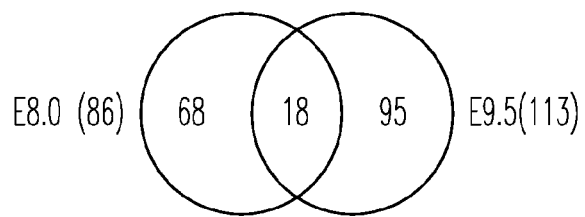
Figure 5F:
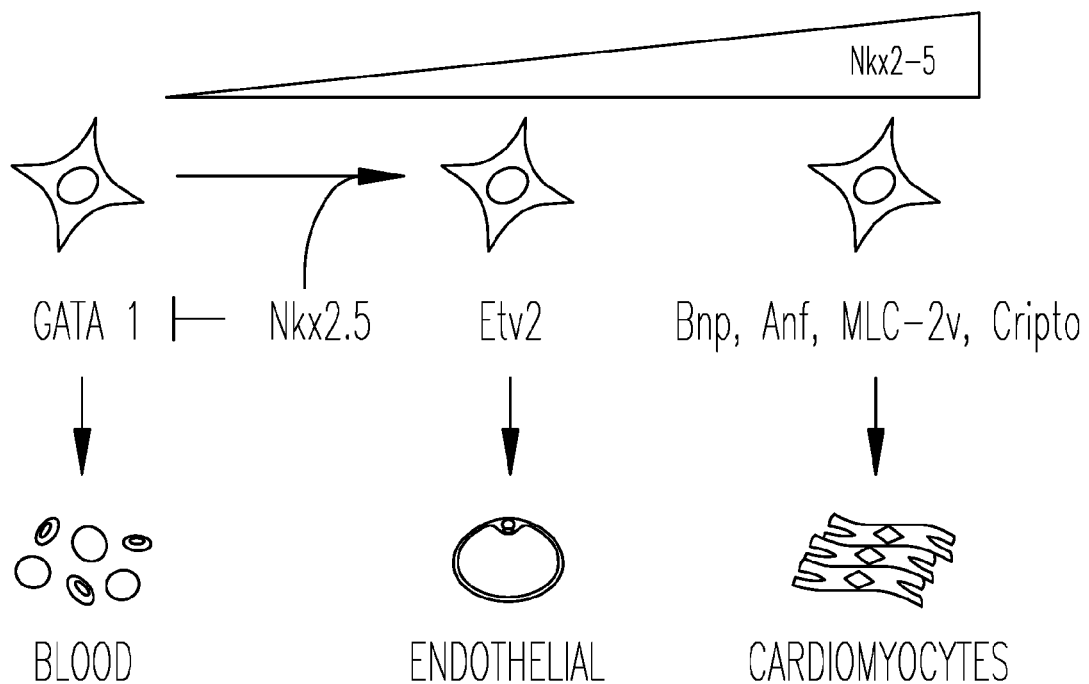

Cardiac development is a complex highly-orchestrated event that includes the specification, proliferation, migration and differentiation of cardiac progenitors that become electrically coupled and ultimately form a functional syncytium (FIG. 1). These stages of cardiogenesis are governed by transcriptional networks, which have been shown, using gene disruption technology, to be required for heart formation and viability (6, 8, 9, 22-26) (Table1).

works that direct the specification of the cardiac lineage from stem cell populations (8, 9, 37). To define Nkx2-5 mediated networks during cardiogenesis, the molecular signature of the CPC population in the developing Nkx2-5 null hearts (9) was examined. The 6 kb Nkx2-5 enhancer-EYFP transgenic mouse model was combinatorialy mated into the Nkx2-5 null background to direct EYFP expression in Nkx2-5 null CPCs. Using FACS, Wt and Nkx2-5 null CPCs from stage (age) matched individual embryos were isolated, RNA was isolated and amplified and the respective molecular programs using whole genome analysis were interrogated. This strategy defined downstream Nkx2-5 target genes and uncovered roles for Nkx2-5 in cardiogenesis, endothelial/endocardial lineage specification (induction of Etv2) and the repression of blood formation (FIG. 5F). The studies also identified a molecular signature for the early CPC population that included Nkx2-5, HandII and Tbx5 (37).

Multiplex Homology-Dependent Recombination (HDR) in Pigs

As previously described (see above), methodologies to introduce bi-allelic knockouts (KOs) into porcine fibroblasts using the TALEN-specified HDR technique (28) were devel-

TABLE 1

Phenotypes of cardiac gene mutation

| Genes mutated | Lethal stage | Morphological features of the heart | Down-regulated transcription factors |
|---|---|---|---|
| Nkx2-5 | E9.5 | Heart tube forms, but does not loop. No demarcation of atria and ventricles. | Hand 1, Mef2C |
| Tbx5 | E10.5 | Hypoplasia of the left ventricle and sinoatrial structures (primitive atria and inflow tract). Heart does not loop. | Nkx2-5, Gata4 |
| Hand2 | E10.5 | Hypoplasia of the right ventricle and aortic arch defects. | Gata4 |
| Nkx2-5 + Hand2 | E8.5-9.5 | Single cardiac: chamber with complete ventricular dysgenesis. | Hand1 |

Figure 2:
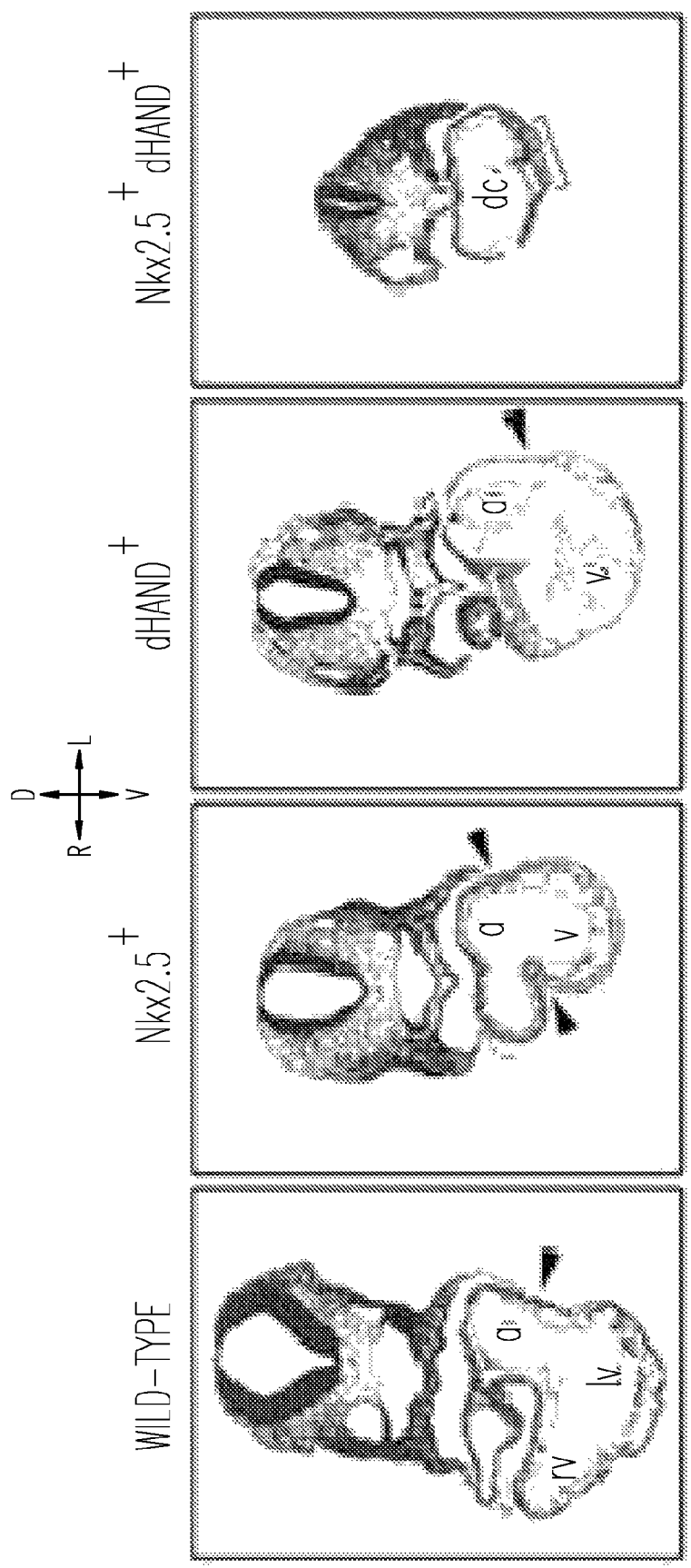
FIG. 2 demonstrates Nkx2-5 and HandII (also known as dHand) double knockouts lack both ventricles (rv and lv) and have a single, small primitive atrium (dc) (Yamagishi 2001).

Nkx2-5 is the vertebrate homolog of the *Drosophila* homeodomain protein, Tinman (Csx). The Tinman mutation results in the absence of heart formation in the fly (35). Nkx2-5 is one of the earliest transcription factors expressed in the cardiac lineage. Targeted disruption of Nkx2-5 results in perturbed heart morphogenesis, severe growth retardation and embryonic lethality at approximately E9.5 (22, 24). One of the Nkx2-5 interacting factors is the T-box transcription factor, Tbx5, which together form a complex and transactivates cardiac gene expression (36). Global deletion of Tbx5 in the mouse results in perturbed cardiac morphogenesis (severe atrial and ventricular hypoplasia) and embryonic lethality by E10.5 (25). Even haploinsufficient mice (Tbx5+/−) display severe congenital heart and forelimb malformations and have been shown to cause the defects in patients with Holt-Oram Syndrome (25). HandII (dHand) is a bHLH transcription factor that has also been shown to be need for cardiac morphogenesis. HandII mutant embryos are lethal during early embryogenesis and have severe right ventricular hypoplasia and aortic arch defects (23). Moreover, mice lacking both Nkx2-5 and HandII demonstrate ventricular agenesis and have only a single atrial chamber (FIG. 2) (26).

Multiplex Knockout of Porcine NKX2-5, HANDII and TBX5 Genes

To define the Nkx2-5 transcriptional regulatory cascade in cardiac progenitor cells, engineered knockout and transgenic mouse models were utilized to define the molecular netoped. These emerging technologies were further utilized to perform multiplex gene KOs (i.e. to engineer an ETV2 knockout along with NKX2-5/HANDII/TBX5 mutations and other organ-specific factors). To verify this technology for multiple bi-allelic gene editing, pairs of TALENs were used that each resulted in more than 20% HDR/site, and simultaneously co-transfected these pairs in three combinations, with each combination targeting five separate genes in the pig genome (28).

Figure 3A:
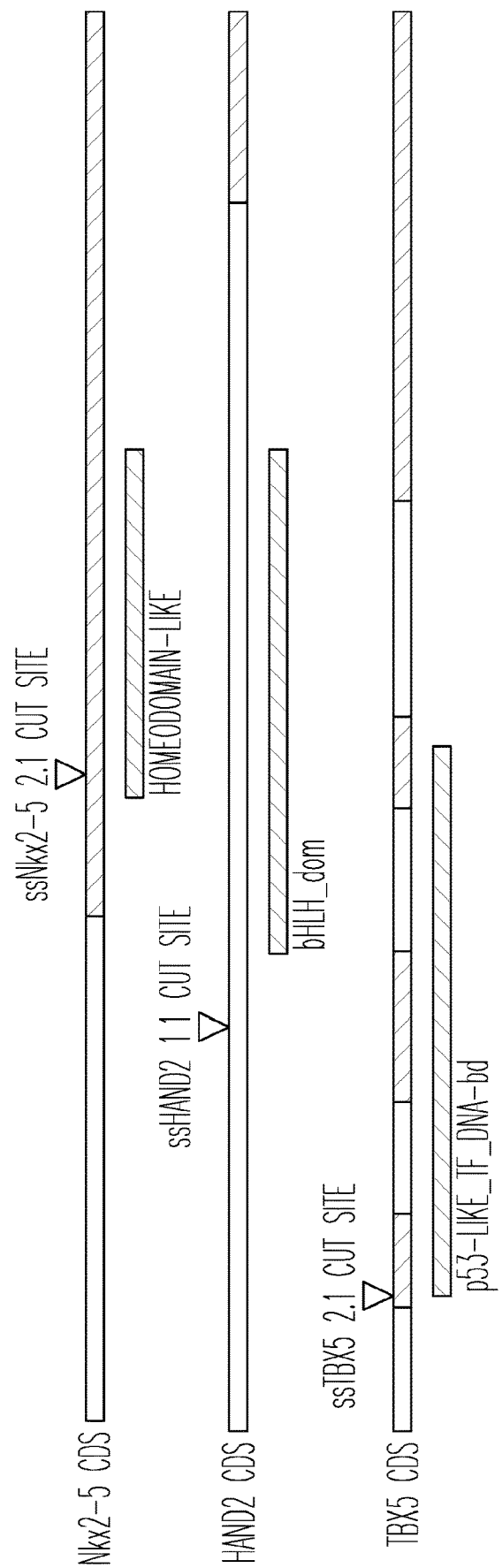
FIGS. 3A-C depict triple knockout of NKX2-5, HANDII and TBX5 in swine fibroblasts. A) Schematics of the coding sequence for each gene are shown; one region (below) indicates the DNA binding domain of each transcription factor, and the triangles indicate the location TALENs binding sites. B) RFLT analysis of fibroblast colonies for bialleic KO of TBX5 and NKX2-5. The asterisk marks double biallelic KO colonies. C) Results of colony screening (n=480). HANDII mutation rate was analyzed by sequencing in only TBX5 and NKX2-5 double positive clones.
Figures 3B, 3C:
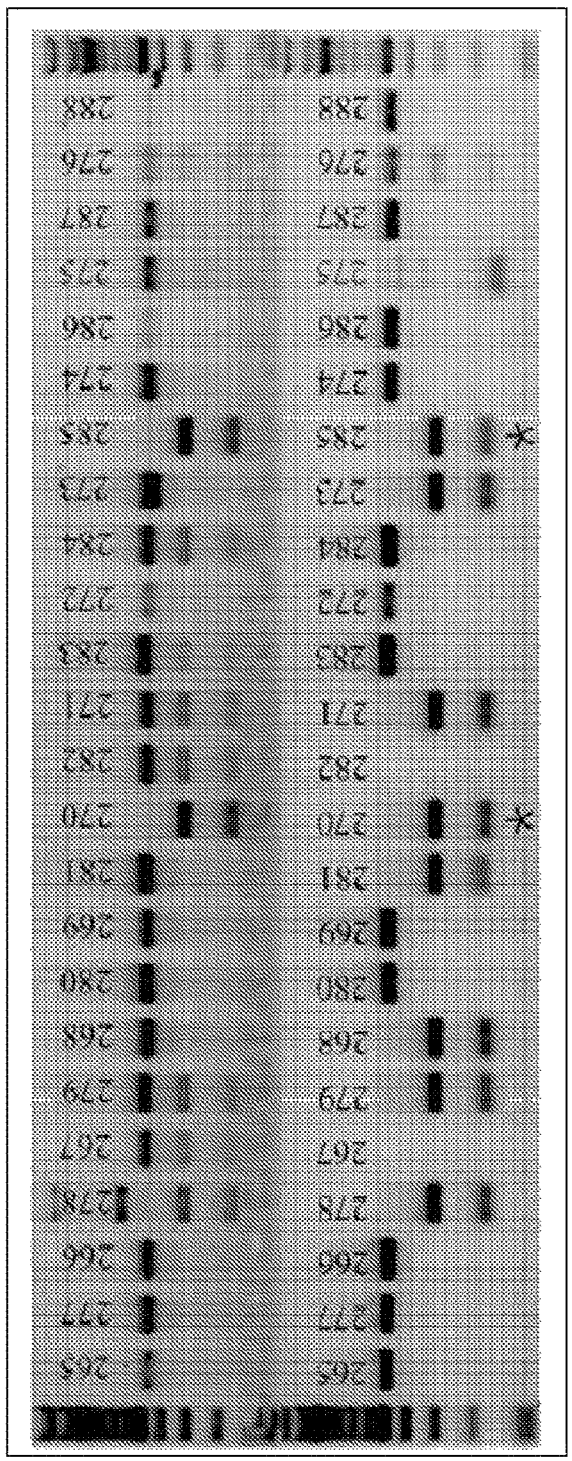
Figure 4:
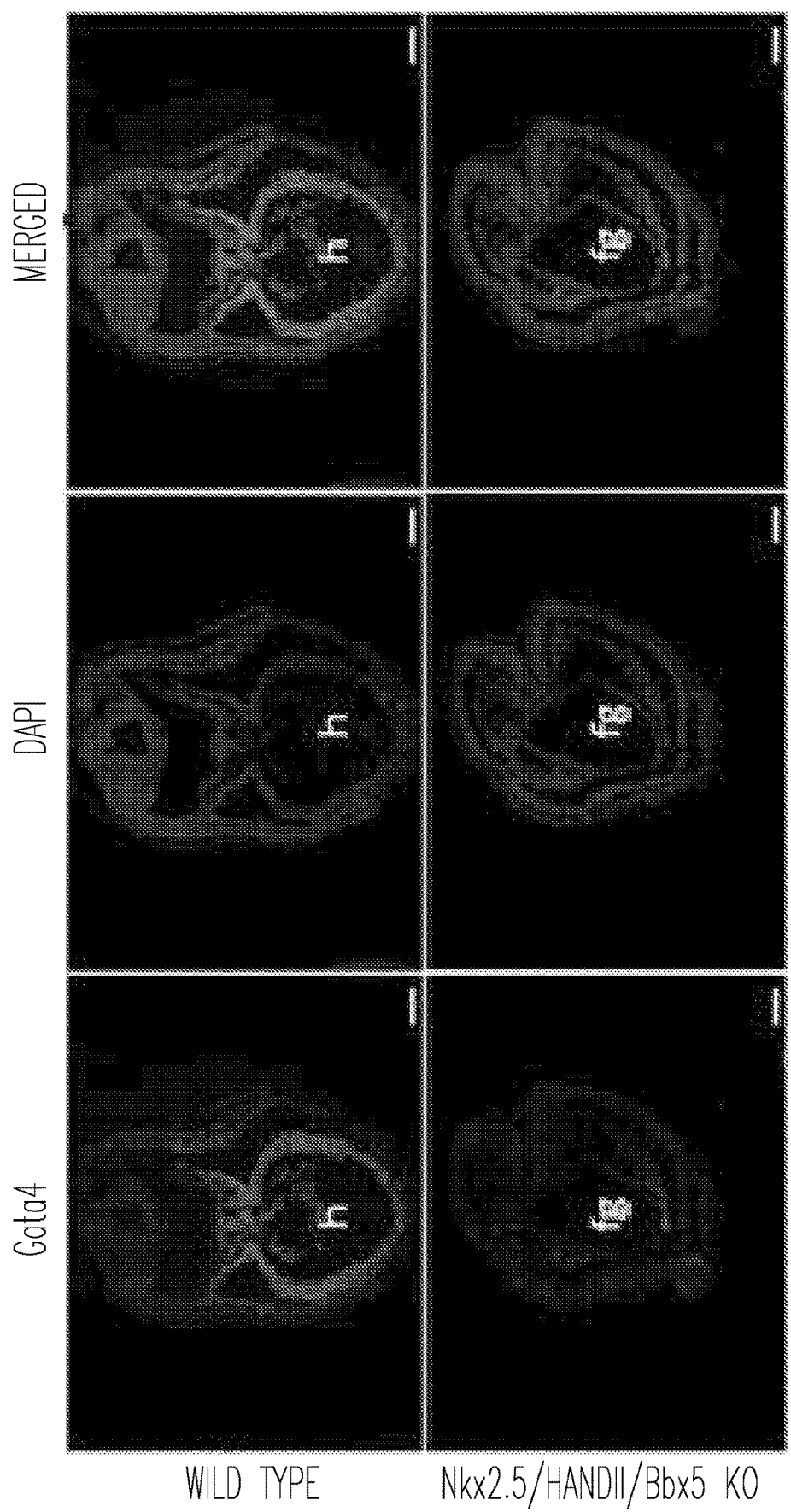
FIG. 4 depicts Nkx2-5/HANDII/TBX5 triple knockout porcine embryos have acardia. Triple knockout porcine embryos lack a heart with essentially no Gata4 immunohistochemically positive cells (marking the heart) at E18.0 (h, heart and fg, foregut).

A combination of TALEN stimulated HDR and mutation by NHEJ (discussed herein) was used to generate NKX2-5/HANDII/TBX5 mutant porcine embryonic fibroblasts. Each gene was targeted either within or immediately prior to their conserved transcription factor/DNA binding domains (FIG. 3A). This strategy is favored over targeting the gene near the transcription start site to reduce the chance of producing a functional peptide by initiation at a downstream AUG. For TBX5 and NKX2-5, a homology template was provided to generate a novel in-frame stop codon, restriction site for RFLP screening, and an additional five base insertion after the stop codon to prevent a functional read-though protein. The HANDII TALENs were about 10% efficient, and therefore the experiments were carried out without a homology template to avoid interference with TBX5 and NKX2-5 HDR, a phenomenon observed using multiplex HDR in pig fibroblasts (unpublished data). Triple mutants were identified using a three-tiered approach. First, colonies were screened for double knockout of TBX5 and NKX2-5 by RFLP assay (FIG. 3B). In the first round of 480) colonies, thirty-three (7%) were found to be double knockouts. Among the double knockouts, four were identified (1% overall) that also were mutant for in HANDII (FIG. 3C). The ability to reliably produce triple null pig fibroblast cell lines in a single shot is unique and a transformative technology. Absence of a Heart in Triple Knockout Pig Embryos The experiments have targeted a number of transcription factors (i.e. MESP1, GATA4, NKX2-5, HANDII, TBX5, etc.) that result in perturbed cardiogenesis and provides new models for the study and treatment of congenital heart disease. Demonstrated herein, as proof-of-concept, successful targeting and generation of clones homozygous for the deletion of NKX2-5/HANDII/TBX5 genes. Triple knockout fibroblast clones were used for nuclear cloning (SCNT) to generate NKX2-5/HANDII/TBX5 null porcine embryos, which were transferred to surrogate sows. Embryos were harvested and analyzed at E18, which is equivalent to E11 of the mouse. At E18, the triple knockout porcine embryos have vasculature, skeletal muscle and blood, but lack a heart (minimal GATA4 immunhistochemically positive cardiomyocytes) (see FIG. 4) compared to the wildtype control porcine embryo.

Example 2—Human Stem Cells Integrate into the Inner Cell Mass (ICM) of Porcine Parthenotes (Embryos Electrically Activated to Develop without Fertilization)

Human stem cell/progenitor cell populations can contribute and participate in porcine parthenote chimeras. The capacity of human inducible pluripotent stem cells (hiPSCs), human mesenchymal stem cells (hMSCs), human pluripotent stem cells and human cardiac progenitors (hCPCs) to contribute to porcine parthenote development will be compared. Data using porcine parthenogenetic blastocysts (30) support the belief that hiPSCs are integrated into the inner cell mass of the parthenotes. The experiments will examine hiPSC lines, hMSC lines, human pluripotent stem cells and hCPCs and their capacity to successfully produce human-porcine chimeras in vitro and in vivo using porcine parthenogenetic embryos. These studies will examine the proliferative capacity of the human stem cell populations, apoptosis and developmental progression for the in vitro analysis. The in vivo analysis will utilize immunohistochemistry with human specific antisera and in situ hybridization of post-implantation parthenotes.

Figure 9A:
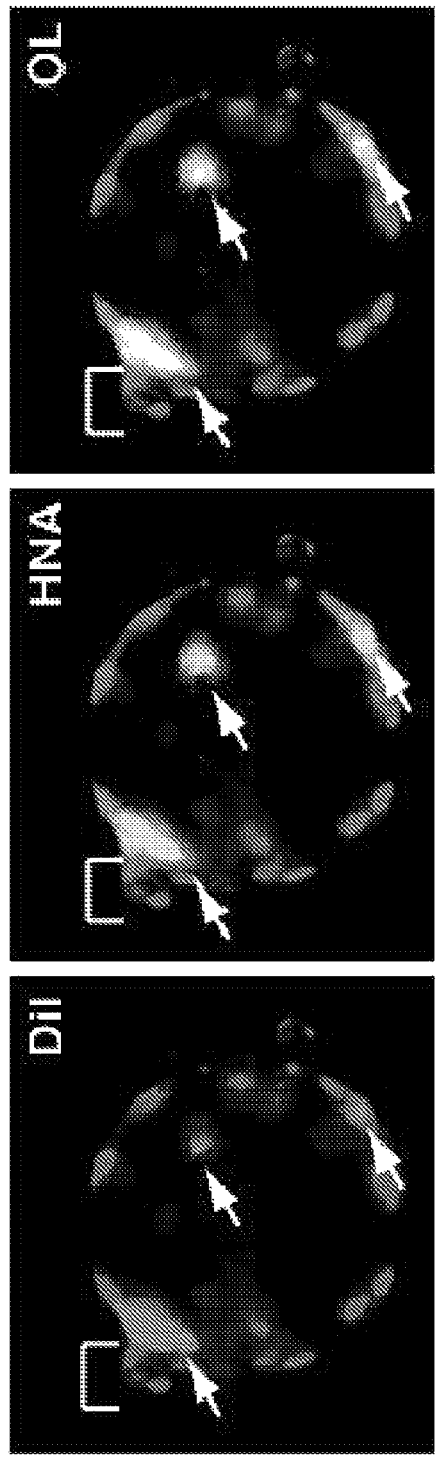
FIGS. 9A-B depict (A) Blastocyst with DiI-labeled hiPSC in the ICM. Arrows indicate cells positive for DiI and HNA. (B) Blastocyst with EdU-labeled hiPSCs in the ICM. hiPSC were labeled with 40 μM EdU for 24 hours and injected. Blastocysts were pulsed with 10 μM BrdU for an hour to label dividing cells. Double positive cells are indicated by arrows. BrdU+/EdU- cells are dividing host cells. Note that the blastocysts are beginning to hatch (brackets), which signifies developmental progression. HNA: human nuclear antigen; OL: overlay.
Figure 9B:

The capacity of hiPSC to integrate into the porcine blastocysts and participate in embryonic development was evaluated. Porcine parthenogenetic blastocysts were generated using electrical stimulation of oocytes (42). Six days following activation 9-12 DiI- or EdU (24 hr)-labeled hiPSC were injected into the blastocoel cavity. Blastocysts were allowed to recover two days in culture and then imaged. Labeled hiPSCs were observed in the ICM of 90% of the porcine blastocysts (FIG. 9A. B, representative images are shown). Comparison of DiI distribution with immunohistochemistry using human nuclear antigen-specific antibody (HNA) reveals that HNA antibody detects injected human stem cells (FIG. 9A, arrows). Blastocysts injected with EdU labeled hiPSC were further pulsed with BrdU for 1 hour before harvest to detect proliferating cells. Double labeling with EdU reveals that injected human stem cells continued to proliferate after 48 hrs of injection (FIG. 9B, arrows). These results demonstrate the incorporation of human stem cells into the ICM of porcine blastocysts, and the developmental progression of the chimeric blastocysts to the hatching stage in preparation for implantation into the uterus.

These results support the rationale and feasibility of the proposed strategy and provide a rapid assay to examine whether human stem cell populations are compatible and/or contribute to the ICM development. Furthermore, implantation of parthenogenetic blastocysts provides a high-throughput method to examine integration and differentiation of human stem cells into developing embryos. A significant advantage of this strategy is that porcine oocytes are abundantly available as a bi-product of food production, and parthenogenetic embryos can be generated in large quantities on a regular basis. It should be noted that parthenogenetic embryos do not survive past 8 weeks, and therefore negates the concern of inadvertently giving birth to undesired human-porcine chimeras.

Human stem cell populations proliferate and contribute to the formation of human-porcine parthenote chimeras. Human mesenchymal stem cells (hMSCs) (46) and cardiac progenitor cells (hCPCs) (47) will be more restricted in their capacity to contribute to embryonic lineages in the developing pig. Furthermore, the hiPSCs and porcine stem cell populations may equally contribute to embryonic lineages.

Human stem/progenitor cell populations will rescue the NKX2-5/HANDII/TBX5 mutant porcine embryo. hiPSCs will be progenitors to every cardiac cell in the NKX2-5/HANDII/TBX5 mutant pre-term embryo.

Utilizing TALEN-mediated techniques (27, 28), an ETV2 mutant pig embryo was generated that is nonviable and lacks an endothelial lineage. Using TALEN-mediated techniques to generate NKX2-5/HANDII/TBX5 mutant fibroblasts and the data demonstrates that these mutant pig embryos lack a heart. The data further support the notion that human stem cells (human cord blood stem cells and human iPSCs) can integrate into the ICM of porcine parthenotes. In human-porcine complementation studies, the engraftment of human stem cells in E17 human stem cell-porcine chimeras will be examined.

Example 3

Materials and Methods
TALEN Design and Production

Candidate TALEN target DNA sequences and RVD sequences were identified using the online tool "TAL EFFECTOR NUCLEOTIDE TARGETER 2.0". Plasmids for TALEN DNA transfection or in vitro TALEN mRNA transcription were then constructed by following the Golden Gate Assembly protocol using RCIscript-GOLDYTALEN (Addgene ID 38143) as final destination vector (Carlson 2012). Assembled RCIscript vectors prepared using the QIAPREP SPIN MINIPREP kit (Qiagen) were linearized by SacI to be used as templates for in vitro TALEN mRNA transcription using the mMESSAGE mMACHINE® T3 Kit (Ambion) as indicated previously (Carlson, 2009). Resulting mRNA was DNAse treated prior to purification using the MEGACLEAR REACTION CLEANUP kit (Applied Biosciences) or RNeasy kit, (Qiagen).

Tissue Culture and Transfection

Pig fibroblasts were maintained at 37 or 30 degrees Celsius (as indicated) at 5% CO2 in DMEM supplemented with 10% fetal bovine serum, 100 I.U./mL penicillin and streptomycin, 2 mM L-Glutamine and 10 mM Hepes. The Neon Transfection system (Life Technologies) was used to deliver TALENs and HDR oligos. Low passage Ossabaw or Landrace pig fibroblasts at 70-100% confluency were spilt 1:2 and harvested the next day at 70-80% confluency. Approximately 600,000 cells were resuspended in "R" Buffer (Life Technologies) with mRNA TALENs and HDR oligos and electroportated in 100 uL tips using the following parameters: input voltage: 1800V; pulse width: 20 ms; pulse number: 1. 0.1-4 ug of TALEN mRNA and 0.1-0.4 nmol of HDR oligos for the specific gene(s) of interest were included for each transfection. Transfected cells were cultured for 2 or 3 days at 30 degrees Celsius, and then analyzed for gene editing efficiency and plated for colonies.

Dilution Cloning

Two or three days post transfection, 50 to 250 cells were seeded onto 10 cm dishes and cultured until individual colonies reached circa 5 mm in diameter. 8 mL of a 1:4 (vol/vol) mixture of TrypLE and DMEM media (Life Technologies) was added and colonies were aspirated, transferred into wells of a 48-well dish and a replica 96 well dish and cultured under the same conditions. Colonies reaching confluence were collected and for cryopreservation and sample preparation for genotyping.

Sample Preparation

Transfected cell populations at day 3 and 10 were collected from a well of a 6-well dish and 10-30% were resuspended in 50 μl of 1×PCR compatible lysis buffer: 10 mM Tris-Cl pH 8.0, 2 mM EDTA, 0.45% Tryton X-100(vol/vol), 0.45% Tween-20(vol/vol) freshly supplemented with 200 μg/ml Proteinase K. The lysates were processed in a thermal cycler using the following program: 55° C. for 60 minutes, 95° C. for 15 minutes.

Analysis of Gene-Edits

PCR flanking the intended sites was conducted using AccuStart™ Taq DNA Polymerase HiFi (Quanta Biosciences) with 1 μl of the cell lysate according to the manufacturer's recommendations. The frequency of mutation in a population was analysed with the SURVEYOR MUTATION DETECTION Kit (Transgenomic) according to the manufacturer's recommendations using 10 ul of the PCR product as described above. SURVEYOR reactions were resolved on a 10% TBE polyacrylamide gels and visualized by ethidium bromide staining. Densitometry measurements of the bands were performed using ImageJ; and mutation rate of SURVEYOR reactions was calculated as described in (Guschin t al. 2010). Individual colonies were screened for the presence of an HDR allele using primers. PCR products underwent restriction fragment length polymorphism analysis (RFLP) by digesting the resulting PCR amplicons with HindIII to determine whether one, both, or none of the alleles were cut and therefor contained the HDR allele. Products were resolved on agarose gels.

PIG Sequences

Nkx2-5: ENSSSCG00000016984
Tbx5: ENSSSCG00000009867
Hand2:ENSSSCG00000009703
Pig Gene: NKX2-5 Gene ID: ENSSSCG00000016984
Description: NK2 homeobox 5 [Source:HGNC Symbol; Acc:HGNC:2488]
Synonyms: CSX, CSX1, NKX2.5, NKX2E, NKX4-1
Location: Chromosome 16: 55,400,561-55,403,626 forward strand.
INSDC coordinates: chromosome:Sscrofa10.2: CM000827.4:55400561:55403626:1
About this gene: This gene has 1 transcript (splice variant), 37 orthologues, 15 paralogues and is a member of 1 Ensembl protein family
Pig NKX2-5 Genomic sequence ID: CU928102

(SEQ ID NO: 1)
..........gtcccctcctccggcctggtcccgcctctcctgccct tgcgcccgcaTTACCTGCCGCCTGGCCACATCCCGAGCTGGAAGGCGG

GTGCGCGGGCGCGCAGCGGGCACCATGCAGGGAGGCTGCCAGGGACCGT

GGGCAGCGCCGCTCTCTGCCGCCCACCTGGCGCTGTGAGACGCGCGCTG

CCACCATGTTCCCCAGCCCCGCGCTCACGCCCACGCCGTTCTCGGTCAA

AGACATCTTGAACCTGGAGCAACAGCAGCGCAGCCTGGCCGCCGGGGAG

-continued

CTCTCCGCGCGCTTGGAGGCCACCCTGGCGCCCGCCTCCTGCATGCTGG

CCGCCTTCAAGCCCGAGGCCTACGCGGGGCCGGAGGCCGCAGCGCCCGG

CCTCTCCGAGCTGCGCGCCGAGCTGGGCCCCGCGCCCTCACCAGCCAAG

TGCGCGCCCTCCTTCTCAGCCGCCCCCGCCTTCTACCCGCGTGCCTATG

GCGACCCCGACCCCGCCAAGGACCCTCGAGCCGATAAGAAAGgtgagga ggaaacacaagcttcttc.........tctgcctctctgttccccccc gcagAGCTGTGCGCGCTGCAGAAGGCGGTGGAGCTGGAGAAGCCAGAGG

CGGACAGCGCCGAGAGACCTCGGGCGCGACGACGAAGGAAGCCGCGCGT

GCTCTTTTCGCAGGCACAGGTCTACGAGCTGGAGCGACGCTTCAAGCAG

CAGCGGTACCTGTCGGCTCCCGAGCGTGACCAGTTGGCCAGCGTGCTGA

AGCTCACGTCCACGCAGGTCAAGATCTGGTTCCAGAACCGGCGCTACAA

GTGCAAGCGGCAACGGCAGGACCAGACTCTGGAGCTAGTGGGGCTGCCC

CCGCCCCCGCCGCCGCCGGCCCGCAGGATCGCGGTGCCAGTGCTGGTGC

GCGATGGCAAGCCTTGCCTCGGGGACTCCGCGCCCTACGCGCCAGCCTA

CGGCGTGGGCCTCAACGCCTACGGCTATAACGCCTACCCCGCCTACCCG

GGTTACGGTGGCGCGGCCTGCAGCCCTGGCTACAGCTGCACCGCTGCGT

ACCCAGCCGGGCCGCCCCCGGCGCAGTCGGCTACGGCCGCCGCCAATAA

CAACTTCGTGAACTTCGGCGTCGGGGACTTAAACGCGGTGCAGAGCCCG

GGGATTCCGCAGGGCAACTCGGGAGTGTCCACGCTGCACGGTATCCGAG

CCTGGTAGGGAAGGGGCCTGTCTGGGGCACCTCTAAAGAGGGGCACTAA

CTATCGGGGAGAGGGAGGGCTCCCGATACGATCCTGAGTCCCTCAGATG

TCACATTGACTCCCACGGAGGCCTCGGAGCTTTTTCCGTCCGGTGCGCC

TTTATCCCCACGCGCGGGAGAGTTCGTGGCAGAGGTTACGCAGCTTGGG

GTGAGTGATCCCGCAGCCCGGTGCCTTAGCCGTCGCCCCGGGAGTGCCC

TCCAAGCGCCCACGGGCATCCCCAATCGGCTGACACCGGCCAGTTGGGA

CCGGGAGCCCGAGCCCAGGCGTGCCAGGCTTAAGATGGGGCCGCCTTTC

CCCGATCCTGGGCCCGGTGCCCGGGGCCCTTGCTGCCTTGCCGCTGCCC

TCCCCACACCCGTATTTATGTTTTTACTTGTTTCTGTAAGAAATGAGAA

TCTCCTTCCCATTAAAGAGAGTGCGCTGAtccgcctgtgtgcttctttc agcttgctgtgcttcagaaactgaaatttt..........

Code:
Exons/Introns

<u>Translated sequence</u>

Flanking sequence

Intron sequence

UTR

Pig NKX2-5 mRNA sequence: ID ENSSSCT00000018494

(SEQ ID NO: 2)
ATGTTCCCCAGCCCCGCGCTCACGCCCACGCCGTTCTCGGTCAAAGACA

TCTTGAACCTGGAGCAACAGCAGCGCAGCCTGGCCGCCGGGGAGCTCTC

CGCGCGCTTGGAGGCCACCCTGGCGCCCGCCTCCTGCATGCTGGCCGCC

TTCAAGCCCGAGGCCTACGCGGGGCCGGAGGCCGCAGCGCCCGGCCTCT

-continued

CCGAGCTGCGCGCCGAGCTGGGCCCCGCGCCCTCACCAGCCAAGTGCGC

GCCCTCCTTCTCAGCCGCCCCCGCCTTCTACCCGCGTGCCTATGGCGAC

CCCGACCCCGCCAAGGACCCTCGAGCCGATAAGAAAGAGCTGTGCGCGC

TGCAGAAGGCGGTGGAGCTGGAGAAGCCAGAGGCGGACAGCGCCGAGAG

ACCTCGGGCGCGACGACGAAGGAAGCCGCGCGTGCTCTTTTCGCAGGCA

CAGGTCTACGAGCTGGAGCGACGCTTCAAGCAGCAGCGGTACCTGTCGG

CTCCCGAGCGTGACCAGTTGGCCAGCGTGCTGAAGCTCACGTCCACGCA

GGTCAAGATCTGGTTCCAGAACCGGCGCTACAAGTGCAAGCGGCAACGG

CAGGACCAGACTCTGGAGCTAGTGGGGCTGCCCCCGCCCCCGCCGCCGC

CGGCCCCGCAGGATCGCGGTGCCAGTGCTGGTGCGCGATGGCAAGCCTTG

CCTCGGGGACTCCGCGCCCTACGCGCCAGCCTACGGCGTGGGCCTCAAC

GCCTACGGCTATAACGCCTACCCCGCCTACCCGGGTTACGGTGGCGCGG

CCTGCAGCCCTGGCTACAGCTGCACCGCTGCGTACCCAGCCGGGCCGCC

CCCGGCGCAGTCGGCTACGGCCGCCGCCAATAACAACTTCGTGAACTTC

GGCGTCGGGGACTTAAACGCGGTGCAGAGCCCGGGGATTCCGCAGGGCA

ACTCGGGAGTGTCCACGCTGCACGGTATCCGAGCCTGGTAG

Pig NKX2-5 Protein sequence: F1SJY9-1

(SEQ ID NO: 3)

```
         10         20         30         40
MFPSPALTPT PFSVKDILNL EQQQRSLAAG ELSARLEATL
         50         60         70         80
APASCMLAAF KPEAYAGPEA AAPGLSELRA ELGPAPSPAK
         90        100        110        120
CAPSFSAAPA FYPRAYGDPD PAKDPRADKK ELCALQKAVE
        130        140        150        160
LEKPEADSAE RPRARRRKP RVLFSQAQVY ELERRFKQQR
        170        180        190        200
YLSAPERDQL ASVLKLTSTQ VKIWFQNRRY KCKRQRQDQT
        210        220        230        240
LELVGLPPPP PPPARRIAVP VLVRDGKPCL GDSAPYAPAY
        250        260        270        280
GVGLNAYGYN AYPAYPGYGG AACSPGYSCT AAYPAGPPPA
        290        300        310        320
QSATAAANNN FVNFGVGDLN AVQSPGIPQG NSGVSTLGHI
RAW
```

Pig Gene: HAND2 ENSSSCG00000009703 (Ensenble)

Description; heart and neural crest derivatives expressed 2 [Source:HGNC Symbol;Acc: HGNC:4808]

Synonyms; bHLHa26, dHand, Hed, Thing2

Location; Chromosome 14: 17,528,447-17,531,529 reverse strand.

INSDC coordinates;

chromosome:Sscrofa10.2:CM000825.4:17528447: 17531529:1

About this gene: This gene has 1 transcript (splice variant), 54 orthologues, 9 paralogues and is a member of 1 Ensembl protein family.

Pig HAND2 genomic sequence. ID: CU468996

Pig HAND2-201 mRNA ID: ENSSSCT00000010638 (Ensemble) XM_005670479

(NCBI, predicted)

298 . . . 767          /gene = "LOC100153751"

/standard_name = "Hand2"          /db_xref = "UniSTS: 238134"

ORIGIN (SEQ ID NO: 4)
```
   1 atggagatct tgctgggaaa atccgcttgc tcccctcacg gcgtccagtc ccggagaaca
  61 gccgccgccg ccgtcaccca ggagccccca cggccgctgc gcaacagccc tccaagcccc
 121 agccgccgcc ttcgcggagc acgagaggag agcggaacac gttactcgct gctaaagtca
 181 cattccagga ccaaaacaac aacaaccaaa aatttcatta aaacaataag cgcccaagaa
 241 cccagatcag gctggttggg ggaagagatc ggccaccccg agatgtcgcc cccgactac
 301 agcatggccc tgtcctacag tccggagtac gccagcggtg ccgccagcct ggaccactcc
 361 cattacgggg gggtgccgcc gggcgccggg ccccgggcc tggggggcc gcgcccggtg
 421 aagcgccggg gcacagccaa ccgcaaggag cggcgcagga ctcagagcat caacagcgcc
 481 ttcgccgagc tgcgcgagtg tatccccaat gtgcccgccg acaccaaact ctccaagatc
 541 aagacgctgc gcctggccac cagctacatc gcctacctca tggacctgct ggccaaggac
 601 gaccagaacg gcgaggcgga ggcctttaag gcggaaatca agaagacaga tgtgaaagaa
 661 gagaaaagga agaaggagct gaatgaaatc ttgaaaagca cagtgagcag caacgacaag
```

-continued

```
 721 aaaaccaaag gccggacggg ctggccgcag catgtctggg ccctggagct caagcagtga 781 ggtggagaaa gaggaggtgg aggtggtgga agaggaggag gagagcgcga gccaggccct 841 ggagccggat gcagacccag gactccgggg cgagctctgc gcactccgct ctgaggactt 901 cctgcatttg gatcatccgg tttatttatg tgcaatgtgc ctccctctct ttgccccct 961 ttgaggcatc cgctccccac cacccctcc aaaaagtgg atatttgaag aaaagcattc 1021 catattttaa tatgaagagg acactcccgc gtggtaaggg atcccgtcgt cgtcttgtag 1081 attctctgtt tgtgaatgtt tcctcttggc tgtgtagaca ccagcgttgc tccctcccca 1141 cctatccagc cccttacaga taaagacagc tgataatagt gtatttgtga agtgtatctt 1201 taatacctgg cctttggata taaatattcc tggggattat aaagttttat ttcaaagcag 1261 aaaacggggc cgctaacatt tccgttgggg tcggtatcta gtgctgccgt ttcatctgtg 1321 tggttcccta tttgaagatg tttccaacag ctccttgttt tgtgcacttc cgtcctctaa 1381 aactaagtgg aatttaatta atattgaagg tgtaaacgtt gtaagtaatc aataaaccac 1441 tgtgtgtttt tttttttt
```

Pig HAND2 protein (predicted) XP_005670536.1
1 . . . 780 /gene = "LOC100153751"

/codon_start = 1 /product = "heart-and neural crest
derivatives-expressed protein 2-like"

/protein_id = "XP_005670536.1"

/db_xref = "GI: 545868321"

/db_xref = "GeneID: 100153751"

(SEQ ID NO: 5)
/translation = "MEILLGKSACSPHGVQSRRTAAAAVTQEPPRPLRNSPPSPSRRLRGAREESGTR

YSLLKSHSRTKTTTTKNFIKTISAQEPRSGWLGEEIGHPEMSPPDYSMALSYSPEYASGAASLDHSHYGG

VPPGAGPPGLGGPRPVKRRGTANRKERRRTQSINSAFAELRECIPNVPADTKLSKIKTLRLATSYIAYLM

DLLAKDDQNGEAEAFKAEIKKTDVKEEKRKKELNEILKSTVSSNDKKTKGRTGWPQHVWALELKQ"

Uniprot ID: F1RJ02-1
(SEQ ID NO: 6)
```
        10         20         30         40         50
GWLGEEIGHP EMSPPDYSMA LSYSPEYASG AASLDHSHYG GVPPGAGPPG 60         70         80         90        100
LGGPRPVKRR GTANRKERRR TQSINSAFAE LRECIPNVPA DTKLSKIKTL 110        120        130        140        150
RLATSYIAYL MDLLAKDDQN GEAEAFKAEI KKTDVKEEKE KKELNEILKS 160        170
TVSSNDKKTK GRTGWPQHVW ALELKQ
```

Pig Gene: TBX5 Gene ID: ENSSSCG00000009867
Pig TBX5 genomic sequence ID: CU468413
Description: T-box 5 [Source:HGNC Symbol;Acc:HGNC: 11604]
Synonyms: HOS
Location: Chromosome 14: 40,211,210-40,259,321 forward strand.

INSDC coordinates: chromosome:Sscrofa110.2: CM000825.4:40211210:40259321:1
About this gene: This gene has 1 transcript (splice variant), 61 orthologues, 8 paralogues and is a member of 1 Ensembl protein family.
Pig Tbx5 gene ID:ENSSSCG00000009867
Pig TBX5 mRNA predicted sequence 487..609 /gene="TBX5" /standard_name="MARC_15663-15664:1016570340:1" /db_xref="UniSTS:267858"

(SEQ ID NO: 7)

```
1    actagagttt tcactcgcag ctccaggcgg ggtggcctcc tccatcctcc accccctcaa
61   cccctgcacc gggtacagag ctctcttctg gcaagtttct ccccgagaga gaagaggaag
121  ggagagcagg acccagagcg gtcacagggc cctgggctca ccatggccga cggagacgag
181  ggctttggcc tggctcacac acccctggaa ccagattcaa aggatctacc ctgtgactca
241  aaacccgaga gtgggctagg ggcccccagc aagtccccgt cgtccccgca ggccgccttc
301  acccagcagg gcatggaagg gatcaaggtg tttctccatg aaagagaact gtggctgaaa
361  tttcacgaag tgggcacaga aatgatcata accaaggctg gcaggcggat gtttcccagt
421  tacaaagtga aggtgactgg ccttaatccc aaaaccaagt acattctcct tatggacatc
481  gttcctgccg atgaccacag atacaagttc gccgataata aatggtctgt gacaggcaaa
541  gcggagcctg ccatgccggg ccgcctctac gtgcacccgg actcgccggc cactggagcg
601  cattggatgc ggcagctcgt ctccttccag aaactcaagc tcaccaacaa ccacctggac
661  ccgtttgggc acattattct aaattccatg cacaaatacc agcccagatt acacatcgtg
721  aaagcggacg aaaataatgg atttggctca aaaaatactg cattctgtac ccacgtcttt
781  cctgagacag cgtttattgc agtgacttcc taccagaacc acaagatcac ccaattaaag
841  atcgagaata atccctttgc caaggattc cggggcagcg atgcatggaa actgcacagg
901  atgtcaagga tgcaaagtaa agaatatccc gtggttccca ggagcacagt gagacagaaa
961  gtggcctcca accacagtcc cttcagcagt gagcctcgtg ctctctccac ctcatccaac
1201 ttggggtccc agtatcagtg tgagaatggt gtgtccggcc cctcccagga cctcctgccc
1081 ccacctaacc cgtacccact tccccaggag cacagccaaa tttaccattg caccaagagg
1141 aaagatgaag aatgttccac cacagagcat ccctataaga agccctacat ggagacgtca
1201 cccagtgaag aggaccccctt ctaccgagcc ggctaccccc agcagcaggg tctgggtgcc
1261 tcctaccgga cagagtcagc ccagcggcag gcctgcatgt acgccagctc cgcaccgccc
1321 agtgagccgg tgcccagcct ggaggacatt agctgcaaca cgtggcccag catgccttcc
1381 tacagcagct gcacagtcac caccgtgcag cccatggaca ggctacccta ccagcacttc
1441 tctgctcact tcacctcggg gccctggtc ccccggctgg ctggcatggc caaccacggc
1501 tccccgcagt tggggaggg aatgttccag caccagacct ccgtggccca ccagcctgtg
1561 gtcaggcagt gtgggcctca gactggcctc cagtccccgg gcagccttca agcgtccgag
1621 ttcctgtact tcatggcgt gccaaggacc ctgtccccgc atcagtacca ctctgctgtg
1681 cacggggtcg gcatggttcc agagtggagt gacaacagct aaagcgaggc ctgctccttc
1741 actgacgttt ccagagggag gggagagagg gagagagaca gtcgcagaga gaaccccaag
1801 aacgagatgt cgcatttcac tccatgttca cgtctgcact tgagaagccc acctggaca
1861 ctgatgtaat cagtagcttg aaaccacaat tcaaaaaatg tgactttgtt ttgtctcaaa
1921 acttaaaaaa tcgacaagag gcgatgagtc ccaacccccc ctaccccgcc
```

```
cccaccatcc     1981 accaccacca cagtcatcaa ctggccacat tcacacgacc tccagatgcc ctccgggatt      2041
ccttcttttg gtctccagaa agtcttgcct catggagtgt tttatcccaa aacatagatg     2101
gagtcattcc ctgtcttggt gttactgttg acattgtta
```

Pig TBX5 protein ID: F1RKD2 (Ensembl, predicted)

>tr|F1RKD2|F1RKD2_PIG Uncharacterized protein OS = Sus scrofa
GN = TBX5 PE = 4 SV = 2

(SEQ ID NO: 8)
```
MADGDEGFGLAHTPLEPDSKDLPCDSKPESGLGAPSKSPSSPQAAFTQQGMEGIKVFLHERELWL

KFHEVGTEMIITKAGRRMFPSYKVKVTGLNPKTKYILLMDIVPADDHRYKFADNKWSVTGKAEPA

MPGRLYVHPDSPATGAHWMRQLVSFQKLKLTNNHLDPFGHIILNSMHKYQPRLHIVKADENNGFG

SKNTAFCTHVFPETAFIAVTSYQNHKITQLKIENNPFAKGFRGSDDMELHRMSRMQSKEYPVVPR

STVRQKVASNHSPFSSEPRALSTSSNLGSQYQCENGVSGPSQDLLPPPNPYPLPQEHSQIYHCTK

RKADEECSTTEHPYKKPYMETSPSEEDPFYRAGYPQQQGLGASYRTESAQRQACMYASSAPPSEP

VPSLEDISCNTWPSMPSYSSCTVTTVQPMDRLPYQHFSAHFTSGPLVPRLAGMANHGSPQLGEGM

FQHQTSVAHQPVVRQCGPQTGLQSPGSLQASEFLYSHGVPRTLSPHQYHSAVHGVGMVPEWSDNS
```

/db_xref = "GeneID: 100522280" (NCBI entry, predicted)

(SEQ ID NO: 9)
```
/translation = "MADGDEGFGLAHTPLEPDSKDLPCDSKPESGLGAPSKSPSSPQAAFTQQ

GMEGIKVFLHERELWLKFHEVGTEMIITKAGRRMFPSYKVKVTGLNPKTKYILLMDIVPADDHRY

KFADNKWSVTGKAEPAMPGRLYVHPDSPATGAHWMRQLVSFQKLKLTNNHLDPFGHIILNSMHKY

QPRLHIVKADENNGFGSKNTAFCTHVFPETAFIAVTSYQNHKITQLKIENNPFAKGFRGSDDMEL

HRMSRMQSKEYPVVPRSTVRQKVASNHSPFSSEPRALSTSSNLGSQYQCENGVSGPSQDLLPPPN

PYPLPQEHSQIYHCTKRKDEECSTTEHPYKKPYMETSPSEEDPFYRAGYPQQQGLGASYRTESAQ

RQACMYASSAPPSEPVPSLEDISCNTWPSMPSYSSCTVTTVQPMDRLPYQHFSAHFTSGPLVPRL

AGMANHGSPQLGEGMFQHQTSVAHQPVVRQCGPQTGLQSPGSLQASEFLYSHGVPRTLSPHQYHS

AVHG VGMVPEWSDNS"
```

*Homo sapiens* NK2 transcription factor related, locus 5 (*Drosophila*), mRNA (cDNA clone MGC:34495 IMAGE:5225103), complete cds
Human NKX2-5 Gene information: GenBank: BC025711.1

---

LOCUS     BC025711         1632 bp     mRNA     linear    PRI 15-JUL-2006 DEFINITION Homo sapiens NK2 transcription factor related, locus 5 (Drosophila), mRNA (cDNA clone MGC:34495 IMAGE:5225103), complete cds. ACCESSION    BC025711    VERSION BC025711.1    GI:19343930

---

Protein Sequence Information

---

108..1082      /gene="NKX2-5"      /gene_synonym="CSX1"

/gene_synonym="NKX2.5"      /codon_start=1      /product=NK2 transcription factor related, locus 5      (Drosophila)"

/protein_id="AAH25711.1"      /db_xref="GI:19343931"

/db_xref="GeneID:1482"      /db_xref="HGNC:HGNC:2488"

/db_xref="MIM:600584"

---

Human NKX2-5 Protein Sequence (SEQ ID NO: 10)
"MFPSPALTPTPFSVKDILNLEQQQRSLAAAGELSARLEATLAPSSCMLAAFKPEAYAGPEAAAPG
LPELRAELGRAPSPAKCASAFPAAPAFYPRAYSDPDPAKDPRAEKKELCALQKAVELEKTEADNAE
RPRARRRKPRVLFSQAQVYELERRKFQQRYLSAPERDQLASVLKLTSTQVKIWFQNRRYKCKRQR
QDQTLELVGLPPPPPPPARRIAVPVLVRDGKPCLGDSAPYAPAYGVGLNPYGYNAYPAYPGYGGAA
CSPGYSCTAAYPAGPSPAQPATAAANNNFVNFGVGDLNAVQSPGIPQSNSGVSTLHGIRAW"

Human NKX2-5 mRNA sequence (SEQ ID NO: 11)
1 gacgggtgcg cgggcgggcg gcggcaccat gcagggaagc tgccaggggc cgtgggcagc
61 gccgctttct gccgcccacc tggcgctgtg agactggcgc tgccaccatg ttccccagcc
121 ctgctctcac gcccacgccc ttctcagtca aagacatcct aaacctggaa cagcagcagc
181 gcagcctggc tgccgccgga gagctctctg cccgcctgga ggcgaccctg gcgccctcct
241 cctgcatgct ggccgccttc aagccagagg cctacgctgg gcccgaggcg gctgcgccgg
301 gcctcccaga gctgcgcgca gagctgggcc gcgcgccttc accggccaag tgtgcgtctg
361 cctttcccgc cgcccccgcc ttctatccac gtgcctacag cgaccccgac ccagccaagg
421 acccagagc gaaaagaaa gagctgtgcg cgctgcagaa ggcggtggag ctggagaaga
481 cagaggcgga caacgcggag cggccccggg cgcgacggcg gaggaagccg cgcgtgctct
541 tctcgcaggc gcaggtctat gagctggagc ggcgcttcaa gcagcagcgg tacctgtcgg
601 cccccgaacg cgaccagctg gccagcgtgc tgaaactcac gtccacgcag gtcaagatct
661 ggttccagaa ccggcgctac aagtgcaagc ggcagcggca ggaccagact ctggagctgg
721 tggggctgcc ccgccgccg ccgccgcctg cccgcaggat cgcggtgcca gtgctggtgc
781 gcgatggcaa gccatgccta ggggactcgg cgccctacgc gcctgcctac ggcgtgggcc
841 tcaatcccta cggttataac gcctaccccg cctatccggg ttacggcggc gcggcctgca
901 gcctggcta cagctgcact gccgcttacc ccgccgggcc ttccccagcg cagccggcca
961 ctgccgccgc caacaacaac ttcgtgaact tcggcgtcgg ggacttgaat gcggttcaga
1021 gccccgggat tccgcagagc aactcgggag tgtccacgct gcatggtatc cgagcctggt
1081 agggaaggga cccgcgtggc gcgaccctga ccgatcccac ctcaacagct ccctgactct
1141 cgggggggaga aggggctccc aacatgaccc tgagtcccct ggattttgca ttcactcctg
1201 cggagaccta ggaactttt ctgtcccacg cgcgtttgtt cttgcgcacg ggagagtttg
1261 tggcggcgat tatgcagcgt gcaatgagtg atcctgcagc ctggtgtctt agctgtcccc
1321 ccaggagtgc cctccgagag tccatgggca ccccggttg gaactgggac tgagctcggg
1381 cacgcagggc ctgagatctg gccgcccatt ccgcgagcca gggccgggcg cccgggcctt
1441 tgctatctcg ccgtcgcccg cccacgcacc caccccgtatt tatgttttta cctattgctg
1501 taagaaatga cgatccccct cccattaaag agagtgcgtt gaaaaaaaaa -continued

```
aaaaaaaaaa      1561 aaaaaaaaaa aaaaaaaaaa aaaaaaaaaa aaaaaaaaaa
aaaaaaaaaa aaaaaaaaaa      1621
aaaaaaaaaa aa //
```

5

*Homo sapiens* heart and neural crest derivatives expressed 2 (HAND2) mRNA, complete cds
GenBank: FJ226608.1
Human HAND2 gene information
LOCUS FJ226608 2351 bp mRNA linear PRI 15 Apr. 2009
DEFINITION *Homo sapiens* heart and neural crest derivatives expressed 2 (HAND2) mRNA, complete cds. ACCESSION FJ226608 VERSION FJ226608.1 GI:209170693
Human HAND2 mRNA information

2234 . . . 2239

/regulatory_class = "polyA_signal_sequence"

/gene = "HAND2" ORIGIN (SEQ ID NO: 12)
```
   1 agctgtacat ggagatcttg ctgggaaaat ccgcttgctc ccctcacgtc gtccagccca
  61 ggagaaccac cgccgtcacc ccggagcttc ctcggccacc gcgcagagcc ctccgagagc
 121 ccgagccgcg gtcttcgagc tccaaggctc attcagggcc ccagatcctt gccccgaaag
 181 gagaggatct gagaaaatgg atgcactgag acctctctga aaaccctccg agagagcgcg
 241 agaggagcga ggacacgtta ctcgcagcta aaatcacatt taaggaccaa aacaacaaca
 301 accaaaaatt tcattaaaac aataagcgcc caagaaccca gatcgggctg gtgggggag
 361 gggaagaggc gggaagggga gggtcgcacg gaggtagctt tgcagtgagc agtcgacccc
 421 gccgcccccc ggcacagctg gaccggctcc tccagccgcg gctcagactc gccctggat
 481 tccgggttag cttcggtgcc aggaccgcgg cccgggcttg gattcccgag actccgcgta
 541 ccagcctcgc gggagccccg gcacctttgt atgagcacga gaggattctg cctccgcgca
 601 gcagcccggg aagcaggagc cgaagcgcgg gccgtggagc aaggcgggaa ccggaggcgg
 661 cggcggcggc ggccaggggc gcacggtgcc aggaccagct cgccgcgccc catggggagc
 721 cggcggccgc agcgctgctg aggcgggccc ggctggccag gcgggggac ggggcccggg
 781 ctgcagcagc ccctctgcg gctgccgggc gggcccgggc gcccggggc tgggggtgg
 841 ggggtggggg aggacgccga gcgctgaggc aggggccgg gccgagggcg cggcggggct
 901 gcgcgcacgc tggggcgcgt ggaggggcgc ggagggcgaa atgagtctgg taggtggttt
 961 tccccaccac ccggtggtgc accacgaggg ctaccgtttt gccgccgccg ccgccgcagc
1021 tgccgccgcc gccgccagcc gctgcagcca tgaggagaac ccctacttcc atggctggct
1081 catcggccac cccgagatgt cgccccccga ctacagcatg gccctgtcct acagccccga
1141 gtatgccagc ggcgccgccg gcctggacca ctcccattac ggggggggtgc cgccgggcgc
1201 cggcccccg ggcctggggg ggccgcgccc ggtgaaggcg cgaggcaccg ccaaccgcaa
1261 ggagcggcgc aggactcaga gcatcaacag cgccttcgcc gaactgcgcg agtgcatccc
1321 caacgtaccc gccgacacca aactctccaa
```

```
aatcaagacc ctgcgcctgg ccaccagcta    1381
catcgcctac ctcatggacc tgctggccaa ggacgaccag aatggcgagg cggaggcctt    1441
caaggcagag atcaagaaga ccgacgtgaa agaggagaag aggaagaagg agctgaacga    1501
aatcttgaaa agcacagtga gcagcaacga caagaaaacc aaaggccgga cgggctggcc 1561 gcagcacgtc tgggccctgg agctcaagca gtgaggagga ggagaaggag gaggaggaga    1621
gcgcgagtga gcaggggcca aggcgccaga tgcagaccca ggactccgga aaagccgtcc    1681
gcgctccgct ctgaggactc cttgcatttg gaatcatccg gtttatttat gtgcaatttc    1741
cttcccctct ctttgacccc ctttgaggca tctgctcccc gtctccccct ccaaaaaaaa    1801
agtggatatt tgaagaaaag cattccatat tttaatacga agaggacact cccgtgtggt    1861
aagggatccc gtcgtctcat agattctgtg tgcgtgaatg ttccctcttg gctgtgtaga 1921 caccagcgtt gccccccgcc aacctactca acccctttcca gataaagaca gtgggcacta    1981
gtgcgtttgt gaagtgtatc tttaatactt ggcctttgga tataaatatt cctgggtatt    2041
ataaagtttt atttcaaagc agaaaacagg gccgctaaca tttccgttgg ggtcggtatc    2101
tagtgctatc cattcatctg tggtcgttcc ctctttgaag atgtttccaa cagccacttg    2161
ttttgtgcac ttccgtcctc taaaactaaa tggaatttaa ttaatattga aggtgtaaac    2221
gttgtaagta ttcaataaac cactgtgttt tttttttaca aaaaccttaa tcttttaatg 2281 gctgatacct caaaagagtt ttgaaaacaa agctgttata cttgttttcg taatatttaa    2341
aatattcaga a //
```

Human HAND2 protein information

/product = "heart and neural crest derivatives expressed 2"

/protein_id = "ACI42790.1"   /db_xref = "GI: 209170694"

(SEQ ID NO: 13)
/translation = "MSLVGGFPHHPVVHHEGYPFAAAAAAAAAAAASRCSHHENPYFHGWLIG

HPEMSPPDYSMALSYSPEYASGAAGLDHSHYGGVPPGAGPPGLGGPRPVKRRGTANRKERRRTQS

INSAFAELRECIPNVPADTKLSKIKTLRLATSYIAYLMDLLAKDDQNGEAEAFKAEIKKTDVKEE

KRKKELNEILKSTVSSNDKKTKGRTGWPQHVWALELKQ"

*Homo sapiens* T-box 5, miRNA (cDNA clone MGC:35581 IMAGE:5204163), complete cds
GenBank: BC027942.1
Human TBX5 gene information:

---
LOCUS    BC027942    3748 bp    mRNA
linear    PRI 15-JUL-2006 DEFINITION Homo sapiens T-box 5,
mRNA (cDNA clone MGC: 35581 IMAGE:5204163),
complete cds. ACCESSION BC027942 VERSION    BC027942.1
GI:20379838

---

Human TBX5 mRNA information:

ORIGIN (SEQ ID NO: 14)
```
  1 ttcagagaga gagagagagg gagagagagt gagagagact gactcttacc tcgaatccgg       61 gaactttaat cctgaaagct gcgctcagaa aggacttcga ccattcactg ggcttccaac
```

-continued

```
121 tttccctccc tgggggtgta aaggaggagc ggggcactga gattatatgg
ttgccggtgc        181 tcttggaggc tattttgtgt tctttggcgc ttgccaactg
ggaagtattt agggagagca        241
agcgcacagc agaggaggtg tgtgttggag
gtgggcagtc gccgcggagg ctccagcggt        301
aggtgcgccc tagtaggcag
cagtagccgc tattctgggt aagcagtaaa ccccgcataa        361 accccggagc
caccatgcct gctccccgc ctcaccgccg gcttccctgc taggagcagc        421
agaggatgtg gtgaatgcac cggcttcacc gaacgagagc agaaccttgc gcgggcacag
481 ggccctgggc gcaccatggc cgacgcagac gagggctttg gcctggcgca
cacgcctctg        541 gagcctgacg caaaagacct gccctgcgat tcgaaacccg
agagcgcgct cggggccccc        601
agcaagtccc cgtcgtcccc gcaggccgcc
ttcacccagc agggcatgga gggaatcaaa        661
gtgtttctcc atgaaagaga
actgtggcta aaattccacg aagtgggcac ggaaatgatc        721 ataaccaagg
ctggaaggcg gatgtttccc agttacaaag tgaaggtgac gggccttaat        781
cccaaaacga agtacattct tctcatggac attgtacctg ccgacgatca cagatacaaa
841 ttcgcagata ataaatggtc tgtgacgggc aaagctgagc ccgccatgcc
tggccgcctg        901 tacgtgcacc cagactcccc cgccaccggg gcgcattgga
tgaggcagct cgtctccttc        961
cagaaactca agctcaccaa caaccacctg
gacccatttg gcatattat tctaaattcc        1021 atgcacaaat accagcctag
attacacatc gtgaaagcgg atgaaaataa tggatttggc        1081 tcaaaaaata
cagcgttctg cactcacgtc tttcctgaga ctgcgtttat agcagtgact        1141
tcctaccaga accacaagat cacgcaatta aagattgaga ataatccctt tgccaaagga
1201 tttcggggca gtgatgacat ggagctgcac agaatgtcaa gaatgcaaag
taaagaatat        1261 cccgtggtcc ccaggagcac cgtgaggcaa aaagtggcct
ccaaccacag tcctttcagc        1321
agcgagtctc gagctctctc cacctcatcc
aatttggggt cccaatacca gtgtgagaat        1381
ggtgtttccg gcccctccca
ggacctcctg cctccaccca acccatacc actgccccag        1441 gagcatagcc
aaatttacca ttgtaccaag aggaaagagg aagaatgttc caccacagac        1501
catccctata agaagcccta catggagaca tcacccagtg aagaagattc cttctaccgc
1561 tctagctatc cacagcagca gggcctgggt gcctcctaca ggacagagtc
ggcacagcgg        1621 caagcttgca tgtatgccag ctctgcgccc cccagcgagc
ctgtgcccag cctagaggac        1681
atcagctgca acacgtggcc aagcatgcct
tcctacagca gctgcaccgt caccaccgtg        1741
cagcccatgg acaggctacc
ctaccagcac ttctccgctc acttcacctc ggggcccctg        1801 gtccctcggc
tggctggcat ggccaaccat ggctccccac agctgggaga gggaatgttc        1861
cagcaccaga cctccgtggc ccaccagcct gtggtcaggc agtgtgggcc tcagactggc
1921 ctgcagtccc ctggcaccct tcagcccccct gagttcctct actctcatgg
cgtgccaagg        1981 actctatccc ctcatcagta ccactctgtg cacggagttg
gcatggtgcc agagtggagc        2041
gacaatagct aaagtgaggc ctgcttcaca
acagacattt cctagagaaa gagagagaga        2101
gaggagaaag agagagaagg
agagagacag tagccaagag aaccccacag acaagatttt        2161 tcatttcacc
caatgttcac atctgcactc aaggtcgctg gatgctgatc taatcagtag        2221
```

```
         cttgaaacca caattttaaa aatgtgactt tcttgttttg tctcaaaact taaaaaaaca
    2281 aacacaaaaa gatgagtccc acccccact accaccacac ccatcaacca
         gccacattca       2341 cgctactccc cagatctctt ccccccattcc ttcttttggg
         ctctagaaag tcttgcctca       2401
ttgagtgttt tccctagtg cgtagttgga
         gtctgtccct gtcttggtgt taatgttgac       2461
attgttatat aataaatgat
         aatatatttt tttctttcaa ttttcttaat gggacccagt       2521 cccttatttg
         ggggaggtc tgaggcaagt atatttcaaa atatgtactt gcgggattcc       2581
         cttcaagtaa accatccctg aaacctaaat tcacgtttcc ccttgactaa gaaaagcacc
    2641 tacctctgcc atgtgatgtt tctgaaaagc ctctgtatgt ccccatttgc
         tttggttttg       2701 tcctgccttc tccaatatca cgtgctcagt tttgcctcta
         cttacccatg gagtcaggat       2761
aacactgacg ctccctggca tcctatctta
         ctcagcccta ccatcttgcc agctctgtct       2821
ttccagctgt ctgtcgctaa
         aacgtggcct atagcttccc ttccggaaag cttgctttga       2881 aaaacttaaa
         aagccccgt ttacatgtag gcaggactgt gataacagtg caagctctgt       2941
         gttgacaaga gttgtggaca aaaagccaaa ataaatattc ttcctgatta aaaaattttt
    3001 ttttgaaaaa acaaggcca gccccaacct tccaaacctc catcaccaac
         aacccaaact       3061 ggatgtcaag caaatgcac aattcctaca gaagaggcaa
         gacacagtca ccaatgatat       3121
ctcgccaaag aaaccacgcc cacaccaatg
         ccgcacacaaa actgtgttta ctgaaagccg       3181
aaaacagtat taaaaaaagt
         gtgtaagtaa agtgttatgg tagggttctt cagatgtaat       3241 attttactgg
         tactattat ttataaatag gaattctaat taagtaataa catgaaatga       3301
         aacccagcat aggagctggc caagagcttt taattttatt gatactcaaa accaagtttg
    3361 tgttttttg ttttttttg ttttttcct ctttcgaatg tgctttgctt
         tttttgatta       3421 aaaagaattt tttttccttt ttttataaac agaccctaat
         aaagagaaca gggtaagatg       3481
tgaggctgag tgtgtttaag tacgtgagag
         agtgtgagtg tgtttgtaag tgagtgtccc       3541
tatgcgatta tgtctcttta
         cgttgctaag gggggagggt gaggattaag tactcgtgcc       3601 ttatatttgt
         gtgccaatta atgcctaata ataccatgt gcttaaacaa gtaaaaaaaa       3661
         aaaaaaaaaa aaaaaaaaaa aaaaaaaaaa aaaaaaaaaa aaaaaaaaaa aaaaaaaaaa
    3721 aaaaaaaaaa aaaaaaaaa aaaaaaaa
Human TBX5 protein information
/codon_start = 1   /product= "T-box 5"   /protein_id = "AAH27942.1"
/db_xref = "GI: 20379839"      /db_xref = "GeneID: 6910"
/db_xref = "HGNC: HGNC: 11604"      /db_xref = "MIM: 601620"
                                                            (SEQ ID NO: 15)
/translation = "MADADEGFGLAHTPLEPDAKDLPCDSKPESALGAPSKSPSSPQAAFTQQG
MEGIKVFLHERERLWLKFHEVGTEMIITKAGRRMFPSYKVKVTGLNPKTKYILLMDIVPADDHRYK
FADNKWSVTGKAEPAMPGRLYVHPDSPATGAHWMRQLVSFQKLKLTNNHLDPFGHIILNSMHKYQP
RLHIVKADENNGFGSKNTAFCTHVFPETAFIAVTSYQNHKITQLKIENNPFAKGFRGSDDMELHRM
SRMQSKEYPVVRSTVRQKVASNHSPFSSESRALSTSSNLGSQYQCENGVSGPSQDLLPPNPYPL
PQEHSQIYHCTKRKEEECSTTDHPYKKPYMETSPSEEDSFYRSSYPQQQGLGASYRTESAQRQACM
```

-continued

```
YASSAPPSEPVPSLEDISCNTWPSMPSYSSCTVTTVQPMDRLPYQHFSAHFTSGPLVPRLAGMANH

GSPQLGEGMFQHQTSVAHQPVVRQCGPQTGLQSPGTLQPPEFLYSHGVPRTLSPHQYHSVHGVGMV

PEWSDNS"
```

BIBLIOGRAPHY

1. Garry, D J, Martin, C M. Circ Res. 2004; 95(9):852-4.
2. Hoffman, J I. Pediatr Cardiol. 1995; 16(3):103-13.
3. Kang, H K, et al. American journal of industrial medicine. 2000; 38(4):447-54.
4. Kramarow, E A, Pastor, P N. NCHS data brief. 2012(101): 1-8.
5. Rasmussen, T L, et al. Circulation. 2011; 123(16):1771-9.
6. Garry, D J. Olson, E N. Cell. 2006; 127(6):1101-4.
7. Latif, S, et al. Trends Cardiovasc Med. 2006; 16(7):234-40.
8. Ferdous, A, et al. Proc Natl Acad Sci USA. 2009; 106(3):814-9. PMCID: 2630085.
9. Caprioli, A, et al. Circulation. 2011:123(15):1633-41. PMCID: 3110259.
10. Rasmussen, T L. et al. Development. 2011:138(21): 4801-12. PMCID: 3190388.
11. Borges, L, et al. Blood. 2012; 119(23):5417-28.
12. Koyano-Nakagawa, N, et al. Stem Cells. 2012; 30(8): 1611-23. PMCID: 3651838.
13. Rasmussen, T L, et al. PLoS One. 2012; 7(11):e50103. PMCID: 3501484.
14. Behrens, et al. Stem Cells and Development. 2013; 22(15):2211-20. PMCID: 3715789.
15. Behrens, A N, et al. Etv2 transactivates Sox7 and regulates endothelial development. Submitted to Developmental Biology. 2013.
16. Borges, L, et al. Levels of endoglin distinctively control TGFb/BMP signaling at different stages of yolk sac hematopoiesis. Submitted to Stem Cells Revised manuscript under review. 2013.
17. Borges, L, et al. Stem Cells. 2013; 31(9): 1893-901. PMCID: 3795927.
18. Chan, S S, et al. Cell Stem Cell. 2013; 12(5):587-601. PMCID: 3646300.
19. Rasmussen, T L, et al. Genesis. 2013; 51(7):471-80.
20. Behrens, A N, et al. Stem Cells Dev. 2014; 23(17):2004-13. PMCID: 4142794.
21. Shi, X, et al. Dev Biol. 2014; 389(2):208-18. PMCID: 4099474.
22. Lyons, I, et al. Genes Dev. 1995; 9(13):1654-66.
23. Srivastava, D, et al. Nat Genet. 1997; 16(2):154-60.
24. Tanaka, M, et al. Development. 1999; 126(6):1269-80.
25. Bruneau, B G, et al. Cell. 2001:106(6):709-21.
26. Yamagishi, H, et al. Dev Biol. 2001; 239(2): 190-203.
27. Carlson, D F, et al. Proc Natl Acad Sci USA. 2012; 109(43): 17382-7. PMCID: 3491456.
28. Tan, W, et al. Proc Natl Acad Sci USA. 2013.
29. Xin. J, et al. PLoS One. 2013; 8(12):e84250. PMCID: 3866186.
30. Kure-bayashi, S, et al. Theriogenology. 2000; 53(5): 1105-19.
31. Naseem, R H, et al. Physiol Genomics. 2007; 30(1):44-52.
32. Martin, C M, et al. Circ Res. 2008; 102(9):1075-81.
33. Sadek, H, et al. Proc Natl Acad Sci USA. 2008; 105(16):6063-8. PMCID: 2329693.
34. Roger, V L, et al. Circulation. 2012; 125(1):188-97.
35. Bodmer, R. Development. 1993; 118(3):719-29.
36. Hiroi, Y, et al. Nat Genet. 2001:28(3):276-80.
37. Masino, A M, et al. Circ Res. 2004; 95(4):389-97.
38. Kobayashi, T, et al. Cell. 2010:142(5):787-99.
39. Usui, J, et al. Am J Pathol. 2012; 180(6):2417-26.
40. Bort, R, et al. Dev Biol. 2006; 290(1):44-56.
41. Matsunari, H, et al. Proc Natl Acad Sci USA. 2013:110 (12):4557-62. PMCID: 3607052.
42. Kure-Bayashi, S, et al. Theriogenology. 1996; 46(6): 1027-36.
43. Adamo, L, Garcia-Cardena, G. Dev Biol. 2012; 362(1): 1-10.
44. Rhee, J M, Iannaccone, P M. Dev Biol. 2012; 365(1): 1-13. PMCID: 3322272.
45. Heinz, M. et al. Exp Hematol. 2002:30(7):809-15.
46. Crisan, M, et al. Cell Stem Cell. 2008; 3(3):301-13.
47. Makkar, R R, et al. Lancet. 2012; 379(9819):895-904.
48. Nakano, K, et al. PLoS One. 2013; 8(4):e61900. PMCID: 3633951.
49. King, T J, et al. Reproduction. 2002; 123(4):507-15.
50. Zhu, J, et al. Cloning Stem Cells. 2003; 5(4):355-65.
51. Brustle, O, et al. Nat Biotechnol. 1998; 16(11):1040-4.
52. Messina, E, et al. Circ Res. 2004; 95(9):911-21.

Bodmer, R. (1993 Development 118(3): 719-729.
Bruneau, B. G., et al. Cell 106(6): 709-721.
Caprioli, A., et al. Circulation 123(15): 1633-1641.
Ferdous, A., et al. Proc Natl Acad Sci USA 106(3): 814-819.
Garry, D. J. and E. N. Olson (2006). Cell 127(6): 1101-1104.
Lyons, I., et al. Genes Dev 9(13): 1654-1666.
Srivastava, D., et al. Nat Genet 16(2): 154-160.
Tanaka. M., et al. Development 126(6): 1269-1280.
Yamagishi, H., et al. Dev Biol 239(2): 190-203.

All publications, patents, and patent applications, Genbank sequences, websites and other published materials referred to throughout the disclosure herein are herein incorporated by reference to the same extent as if each individual publication, patent, or patent application, Genbank sequences, websites and other published materials was specifically and individually indicated to be incorporated by reference. In the event that the definition of a term incorporated by reference conflicts with a term defined herein, this specification shall control.

What is claimed is:

1. A chimeric pig embryo comprising: (i) homozygous disruptions of endogenous NKX2-5, HANDII, and TBX5 genes in it genome, wherein said disruptions result in no expression of the endogenous NKX2-5, HANDII, and TBX5 proteins; and (ii) human cardiac cells expressing human NKX2-5, HANDII, and TBX5 proteins, wherein the human cardiac cells are differentiated from human pluripotent stem cells introduced into a pig embryo at an earlier stage of development than said chimeric pig embryo and wherein the introduced human pluripotent cells integrated into the inner cell mass of the pig embryo at the blastocyst stage.

2. A chimeric pig blastocyst comprising: (i) homozygous disruptions of endogenous NKX2-5, HANDII, and TBX5 genes in its genome, wherein said disruptions result in no expression of the endogenous NKX2-5, HANDII, and TBX5 proteins; and (ii) human pluripotent cells having intact NKX2-5, HANDII, and TBX5 genes, wherein the human pluripotent cells integrate into the inner cell mass of the blastocyst.

* * * * *

UNITED STATES PATENT AND TRADEMARK OFFICE
CERTIFICATE OF CORRECTION

PATENT NO. : 10,897,880 B2
APPLICATION NO. : 15/739066
DATED : January 26, 2021
INVENTOR(S) : Garry et al.

It is certified that error appears in the above-identified patent and that said Letters Patent is hereby corrected as shown below:

In the Specification

In Column 1, Line 23, delete "end stage" and insert --endstage-- therefor

In Column 1, Line 51, delete "gene." and insert --gene,-- therefor

In Column 1, Line 54, delete "protein." and insert --protein,-- therefor

In Column 1, Line 62, delete "HANDII." and insert --HANDII,-- therefor

In Column 2, Line 7, delete "HANDII." and insert --HANDII,-- therefor

In Column 2, Line 13, delete "NKX2-5." and insert --NKX2-5,-- therefor

In Column 2, Line 33, delete "gene." and insert --gene,-- therefor

In Column 2, Line 35, delete "protein." and insert --protein,-- therefor

In Column 2, Line 56, delete "protein." and insert --protein,-- therefor

In Column 3, Line 20, delete "HANDII." and insert --HANDII,-- therefor

In Column 3, Line 27, delete "HANDII." and insert --HANDII,-- therefor

In Column 4, Line 36, delete "RFLT" and insert --RFLP-- therefor

In Column 10, Line 67, delete "Alternatively." and insert --Alternatively,-- therefor In Column 12, Line 7, delete "A. T." and insert --A, T,-- therefor Signed and Sealed this
Eleventh Day of May, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,897,880 B2

In Column 13, Line 6, delete "(pseudopragnant/surrogate)" and insert --(pseudopregnant/surrogate)-- therefor In Column 15, Line 3, delete ""comprising."" and insert --"comprising,"-- therefor In Column 19, Line 1, delete "480)" and insert --480-- therefor In Column 21, Line 33, delete "t" and insert --et-- therefor